(12) United States Patent
Nelson et al.

(10) Patent No.: US 7,820,641 B2
(45) Date of Patent: *Oct. 26, 2010

(54) SUBSTITUTED TETRACYCLINE COMPOUNDS

(75) Inventors: Mark L. Nelson, Norfolk, MA (US); Peter Viski, Asharoken, NY (US); Jackson Chen, Brookline, MA (US); Tadeusz Warchol, Northborough, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 1122 days.

This patent is subject to a terminal disclaimer.

(21) Appl. No.: 10/740,961

(22) Filed: Dec. 18, 2003

(65) Prior Publication Data

US 2005/0038002 A1 Feb. 17, 2005

Related U.S. Application Data

(63) Continuation of application No. 10/391,903, filed on Mar. 18, 2003, now abandoned.

(60) Provisional application No. 60/440,305, filed on Jan. 14, 2003, provisional application No. 60/395,468, filed on Jul. 12, 2002, provisional application No. 60/367,045, filed on Mar. 21, 2002, provisional application No. 60/366,915, filed on Mar. 21, 2002, provisional application No. 60/367,048, filed on Mar. 21, 2002.

(51) Int. Cl.
*A61K 31/65* (2006.01)
*C07C 237/26* (2006.01)

(52) U.S. Cl. ..................... 514/152; 552/203
(58) Field of Classification Search ............... 514/152; 552/203
See application file for complete search history.

(56) References Cited

U.S. PATENT DOCUMENTS

| | | | |
|---|---|---|---|
| 3,043,875 A | 7/1962 | Beereboom | |
| 3,165,531 A | 1/1965 | Blackwood et al. | |
| 3,200,149 A | 8/1965 | Blackwood et al. | |
| 3,219,671 A | 11/1965 | Hlavka | |
| 3,226,436 A | 12/1965 | Petisi et al. | |
| RE26,253 E | 8/1967 | Petisi et al. | |
| 3,338,963 A | 8/1967 | Patisi et al. | |
| RE26,271 E | 9/1967 | Boothe et al. | |
| 3,341,585 A | 9/1967 | Bitha et al. | |
| 3,345,379 A | 10/1967 | Martell et al. | |
| 3,345,410 A | 10/1967 | Winterbottom et al. | |
| 3,360,561 A | 12/1967 | Zambrano | |
| 3,373,196 A | 3/1968 | Bitha et al. | |
| 3,397,230 A | 8/1968 | Winterbottom et al. | |
| 3,403,179 A | 9/1968 | Zambrano | |
| 3,454,697 A | 7/1969 | Joyner et al. | |
| 3,483,251 A | 12/1969 | Zambrano | |
| 3,518,306 A | 6/1970 | Martell, Jr. et al. | |
| 3,579,579 A | 5/1971 | Hlavka et al. | |
| 3,609,188 A | 9/1971 | Esse et al. | |
| 3,795,707 A | 3/1974 | Luciano | |
| 3,849,493 A | 11/1974 | Conover | |
| 3,862,225 A | 1/1975 | Conover | |
| 3,901,942 A | 8/1975 | Luigi et al. | |
| 3,993,694 A | 11/1976 | Martin et al. | |
| 4,018,889 A | 4/1977 | Armstrong | |
| 4,024,272 A | 5/1977 | Rogalski et al. | |
| 4,126,680 A | 11/1978 | Armstrong | |
| 5,248,797 A | 9/1993 | Sum | |
| 5,281,628 A | 1/1994 | Hlavka et al. | |
| 5,284,963 A | 2/1994 | Sum et al. | |
| 5,326,759 A | 7/1994 | Hlavka et al. | |
| 5,328,902 A | 7/1994 | Sum et al. | |
| 5,371,076 A | 12/1994 | Lee et al. | |
| 5,380,888 A | 1/1995 | Sum et al. | |
| 5,386,041 A | 1/1995 | Sum et al. | |
| 5,401,729 A | 3/1995 | Sum et al. | |
| 5,401,863 A | 3/1995 | Hlavka et al. | |
| 5,420,272 A | 5/1995 | Sum et al. | |
| 5,430,162 A | 7/1995 | Sum et al. | |
| 5,442,059 A | 8/1995 | Sum et al. | |
| 5,457,096 A | 10/1995 | Sum et al. | |
| 5,466,684 A | 11/1995 | Sum et al. | |

(Continued)

FOREIGN PATENT DOCUMENTS

EP 0736302 A2 10/1996

(Continued)

OTHER PUBLICATIONS

Barden, Timothy C. et al, "'Glycylcyclines'. 3. 9-Aminodoxycyclinecarboxamides," *J. Med. Chem.*, vol. 37:3205-3211 (1994).

(Continued)

*Primary Examiner*—Barbara P Badio
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The present invention pertains, at least in part, to novel substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

14 Claims, No Drawings

U.S. PATENT DOCUMENTS

| | | | |
|---|---|---|---|
| 5,494,903 A | 2/1996 | Hlavka et al. |
| 5,495,018 A | 2/1996 | Sum et al. |
| 5,495,030 A | 2/1996 | Sum et al. |
| 5,495,031 A | 2/1996 | Sum et al. |
| 5,512,553 A | 4/1996 | Sum et al. |
| 5,529,990 A | 6/1996 | Hlavka et al. |
| 5,530,117 A | 6/1996 | Hlavka et al. |
| 5,567,692 A | 10/1996 | Sum et al. |
| 5,567,693 A | 10/1996 | Backer et al. |
| 5,639,742 A | 6/1997 | Lee et al. |
| 5,675,030 A | 10/1997 | Krishnam et al. |
| 5,834,450 A | 11/1998 | Su |
| 5,843,925 A | 12/1998 | Backer et al. |
| 5,856,315 A | 1/1999 | Backer et al. |
| 5,886,175 A | 3/1999 | Sum et al. |
| 5,998,390 A | 12/1999 | Ramamurthy et al. |
| 6,319,910 B1 | 11/2001 | Amin et al. |
| 6,500,812 B2 | 12/2002 | Nelson et al. |
| 6,506,740 B1 | 1/2003 | Ashley et al. |
| 6,613,756 B2 | 9/2003 | Duncan et al. |
| 6,617,318 B1 | 9/2003 | Nelson et al. |
| 6,624,168 B2 | 9/2003 | Nelson et al. |
| 6,642,270 B2 | 11/2003 | Nelson et al. |
| 6,683,068 B2 * | 1/2004 | Nelson et al. | 514/152 |
| 6,710,033 B1 | 3/2004 | Stratton et al. |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 * | 1/2005 | Draper et al. | 514/152 |
| 6,846,939 B2 | 1/2005 | Nelson et al. |
| 6,849,615 B2 | 2/2005 | Nelson et al. |
| 7,001,918 B2 | 2/2006 | Huss et al. |
| 7,045,507 B2 | 5/2006 | Draper et al. |
| 7,056,902 B2 * | 6/2006 | Nelson et al. | 514/152 |
| 7,067,681 B2 | 6/2006 | Nelson et al. |
| 2002/0123637 A1 | 9/2002 | Levy et al. |
| 2002/0128237 A1 | 9/2002 | Nelson et al. |
| 2002/0128238 A1 | 9/2002 | Nelson et al. |
| 2002/0132798 A1 | 9/2002 | Nelson et al. |
| 2004/0048835 A1 | 3/2004 | Nelson et al. |
| 2004/0063674 A1 | 4/2004 | Levy et al. |
| 2004/0092490 A1 | 5/2004 | Draper et al. |
| 2004/0138183 A1 | 7/2004 | Nelson et al. |
| 2004/0152674 A1 | 8/2004 | Levy et al. |
| 2004/0176334 A1 | 9/2004 | Nelson et al. |
| 2004/0214800 A1 | 10/2004 | Levy et al. |
| 2004/0214801 A1 | 10/2004 | Nelson et al. |
| 2004/0242548 A1 | 12/2004 | Draper et al. |
| 2004/0266740 A1 | 12/2004 | Huss et al. |
| 2005/0020545 A1 | 1/2005 | Draper et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0137174 A1 | 6/2005 | Ohemeng et al. |
| 2005/0143352 A1 | 6/2005 | Nelson et al. |
| 2005/0143353 A1 | 6/2005 | Nelson et al. |
| 2005/0148551 A1 | 7/2005 | Nelson et al. |
| 2005/0187198 A1 | 8/2005 | Nelson et al. |
| 2005/0215532 A1 | 9/2005 | Levy et al. |
| 2005/0250744 A1 | 11/2005 | Levy et al. |
| 2005/0288262 A1 | 12/2005 | Bandarage et al. |
| 2006/0003971 A1 | 1/2006 | Nelson |
| 2006/0084634 A1 | 4/2006 | Huss et al. |
| 2006/0089336 A1 | 4/2006 | Nelson et al. |
| 2006/0148765 A1 | 7/2006 | Nelson |

FOREIGN PATENT DOCUMENTS

| | | |
|---|---|---|
| EP | 1241160 A1 | 9/2002 |
| GB | 921252 | 3/1963 |
| GB | 1469384 | 4/1977 |
| WO | WO-96/34852 A1 | 11/1996 |
| WO | WO-96/40982 A1 | 12/1996 |
| WO | WO-00/28983 A1 | 5/2000 |
| WO | WO-01/19784 A1 | 3/2001 |
| WO | WO-01/74761 A1 | 10/2001 |
| WO | WO-01/87824 A2 | 11/2001 |
| WO | WO-01/98236 A2 | 12/2001 |
| WO | WO-01/98259 A1 | 12/2001 |
| WO | WO 02/04406 * | 1/2002 |
| WO | WO-02/04406 A2 | 1/2002 |
| WO | WO-02/04407 A2 | 1/2002 |
| WO | WO-02/085303 A2 | 10/2002 |
| WO | WO-03/005971 A2 | 1/2003 |
| WO | WO-03/057169 A2 | 7/2003 |
| WO | WO-03/075857 A2 | 9/2003 |

OTHER PUBLICATIONS

Boothe, James H. et al, "6-Deoxytetracyclines. I. Chemical Modification by Electrophilic Substitution," *J. Am. Chem. Soc.*, vol. 82:1253-1254 (1960).

CAplus Accession No. 1994:217052, Sum, P.-E. et al, "Glycylcyclines. 1. A new generation of potent antibacterial agents through modification of 9-aminotetracyclines," *Journal of Medicinal Chemistry*, vol. 37(1):184-188 (1994).

Koza, Darrell J., "Synthesis of 7-Substituted Tetracycline Derivatives," *Organic Letters*, vol. 2(6):815-817 (2000).

Koza, Darrell J. et al, "Palladium Catalyzed C-N Bond Formation in the Synthesis of 7-Amino-Substituted Tetracyclines," *J. Org. Chem.*, vol. 67:5025-5027 (2002).

Koza, Darrell J. et al, "Synthesis and Biological Evaluation of 9-Substituted Tetracycline Derivatives," *Bioorganic & Medicinal Chemistry Letters*, vol. 12:2163-2165 (2002).

Martell, Jr., Michael J. et al, "The 6-Deoxytetracyclines. VII. Alkylated Aminotetracyclines Possessing Unique Antibacterial Activity," *J. Med. Chem.*, vol. 10(1):44-46 (1967).

Petersen, P.J. et al, "In Vitro and In Vivo Antibacterial Activities of a Novel Glycylcycline, the 9-*t*-Butylglycylamido Derivative of Minocycline (GAR-936)," *Antimicrobial Agents and Chemotherapy*, vol. 43(4):738-744 (1999).

Spencer, John L. et al, "6-Deoxytetracyclines. V. 7,9-Disubstituted Products," *J. Med. Chem.*, vol. 122:405-407 (1963).

Sum, Phaik-Eng et al, "Synthesis and antibacterial activity of 9-substituted minocycline derivatives," *Bioorganic & Medicinal Chemistry Letters*, vol. 16:400-403 (2006).

Sum, Phaik-Eng et al, "Synthesis and Structure-Activity Relationship of Novel Glycylcycline Derivatives Leading to the Discovery of GAR-936," *Bioorganic & Medicinal Chemistry Letters*, vol. 9:1459-1462 (1999).

Sum, Phaik-Eng et al, "Glycylcyclines. 1. A New Generation of Potent Antibacterial Agents through Modification of 9-Aminotetracyclines," *J. Med. Chem.*, vol. 37:184-188 (1994).

International Search Report for Application No. PCT/US03/08324, dated Aug. 3, 2004.

Paemen, Liesbet et al., "The Gelatinase Inhibitory Activity of Tetracyclines and Chemically Modified Tetracycline Analogues as Measured by a Novel Microtiter Assay for Inhibitors," *Biochemical Pharmacology*, vol. 52:105-111 (1996).

Supplementary Partial European Search Report for Application No. 03714236.1-1521, dated Apr. 23, 2007.

* cited by examiner

SUBSTITUTED TETRACYCLINE COMPOUNDS

RELATED APPLICATIONS

This application is a continuation application of U.S. Ser. No. 10/391,903 entitled "Substituted Tetracycline Compounds", filed Mar. 18, 2003, now abandoned, which claims priority to U.S. Provisional Patent Application Ser. No. 60/440,305, entitled "Substituted Tetracycline Compounds," filed Jan. 14, 2003; U.S. Provisional Patent Application Ser. No. 60/395,468, entitled "Substituted Tetracycline Compounds," filed Jul. 12, 2002; U.S. Provisional Patent Application Ser. No. 60/367,045, entitled "7-Substituted Tetracycline Compounds," filed Mar. 21, 2002; U.S. Provisional Patent Application Ser. No. 60/366,915, entitled "7,9-Substituted Tetracycline Compounds," filed Mar. 21, 2002; and U.S. Provisional Patent Application Ser. No. 60/367,048, entitled "9-Substituted Minocycline Compounds," filed Mar. 21, 2002. The entire contents of each of the aforementioned patent applications are hereby incorporated herein by reference in their entirety.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline analogue compositions as antibiotics of choice.

SUMMARY OF THE INVENTION

In one embodiment, the invention pertains, at least in part, to substituted tetracycline compounds of Formula I:

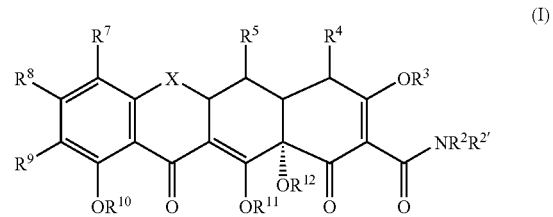

wherein:

X is $CHC(R^{13}Y'Y)$, $CR^{6'}R^6$, $C=CR^{6'}R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is boronic acid moiety, isoxazolyl, sulfonic acid heterocyclic, carbonyl, alkylsulfinyl, alkylsulfonyl, arylalkenyl, arylalkynyl, or $-(CH_2)_{0-3}NR^{7c}C(=W')WR^{7a}$;

$R^9$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso (e.g., $-N=S$), or $-(CH_2)_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$, S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters, enantiomers, and prodrugs thereof.

In an embodiment, the invention pertains to 7,9-substituted tetracycline compounds of Formula II:

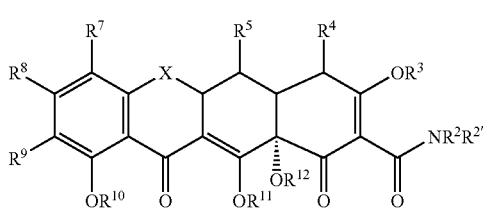

(II)

wherein:

X is CHC(R$^{13}$Y'Y), CR$^{6'}$R$^6$, S, NR$^6$, or O;

R$^2$, R$^{2'}$, R$^{4'}$, and R$^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^4$ is NR$^{4'}$R$^{4''}$, alkyl, alkenyl, alkynyl, hydroxyl, halogen, or hydrogen;

R$^{2'}$, R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is —CH$_2$NR$^{7a}$R$^{7b}$, halogen, —CH$_2$OR$^{7a}$, substituted alkenylfuranyl, pyrazinyl, pyridinyl, alkyl, acyl, alkyl, alkenyl, alkynyl, aryl, alkoxy, alkylthio, alkylsulfinyl, alkylsulfonyl, arylalkyl, amino, arylalkenyl, arylalkynyl, or —(CH$_2$)$_{0-3}$NR$^{7c}$C(=W')WR$^{7a}$;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^9$ is —CH$_2$SR$^{9a}$, —CH$_2$S(=O)R$^{9a}$, —CH$_2$S(=O)$_2$R$^{9a}$, —CH$_2$NR$^{9a}$R$^{9b}$, SO$_3$H, aminoalkyl, furanyl, substituted alkyl, —(CH$_2$)$_{0-3}$ (NR$^{9c}$)$_{0-3}$C(=Z')(Z)$_{0-1}$R$^{9a}$, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —(CH$_2$)$_{0-3}$ (NR$^{9c}$)$_{0-1}$C(=Z')(Z)$_{0-1}$R$^{9a}$;

Z is CR$^{9d}$R$^{9e}$, S, NR$^{9b}$ or O;

Z' is O, S, or NR$^{9f}$;

W is CR$^{7d}$R$^{7e}$, S, NR$^{7b}$ or O;

W' is O, NR$^{7f}$ S;

R$^{7a}$, R$^{7b}$, R$^{7c}$, R$^{7d}$, R$^{7e}$, R$^{9a}$, R$^{9b}$, R$^{9c}$, R$^{9d}$, and R$^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, enantiomers, prodrugs, and amides thereof, provided that R$^7$ and R$^9$ are not both unsubstituted phenyl.

The invention pertains, at least in part to minocycline compounds of formula III:

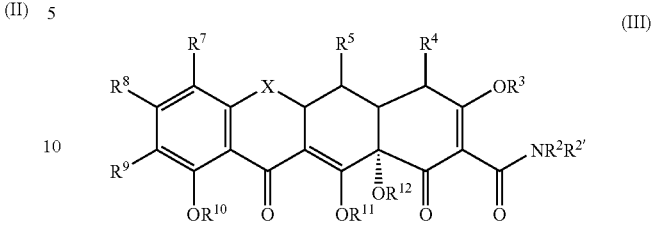

(III)

wherein:

X is CHC(R$^{13}$Y'Y), CR$^{6'}$R$^6$, S, NR$^6$, or O;

R$^2$, R$^{4'}$, R$^{4''}$, R$^{7'}$ and R$^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^4$ is NR$^{4'}$R$^{4''}$, alkyl, alkenyl, alkynyl, aryl, hydroxyl, halogen, or hydrogen;

R$^{2'}$, R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is NR$^{7'}$R$^{7''}$, alkyl, alkenyl, alkynyl, aryl, hydroxyl, halogen, or hydrogen;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^9$ is —C(=Z')R$^{9a}$, CH$_2$S(=O)R$^{9a}$, —CH$_2$OR$^{9a}$, alkylthio, alkylsulfinyl, alkylsulfonyl, arylalkyl, heterocyclic, arylalkenyl, arylalkynyl, thionitroso, substituted alkyl, or —(CH$_2$)$_{0-3}$ (NR$^{9c}$)$_{0-1}$C(=Z')(Z)$_{0-1}$R$^{9a}$;

Z is CR$^{9d}$R$^{9e}$, S, NR$^{9b}$ or O;

Z' is NR$^{9f}$, O or S;

R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, amides, enantiomers, esters and prodrugs thereof.

The invention also pertains to 8 substituted tetracycline compound of the formula IV:

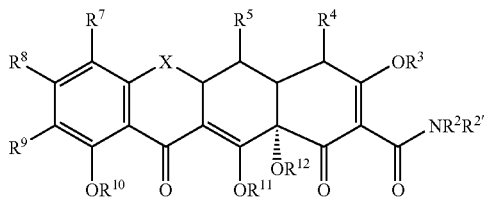
(IV)

wherein:

X is CHC(R$^{13}$Y'Y), CR$^6$R$^{6'}$, S, NR$^6$, or O;

R$^2$, R$^{4'}$, R$^{4''}$, R$^{7'}$ and R$^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^4$ is NR$^{4'}$R$^{4''}$, alkyl, alkenyl, alkynyl, aryl, hydroxyl, halogen, or hydrogen;

R$^{2'}$, R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH$_2$)$_{0-3}$(NR$^{7c}$)$_{0-1}$C(=W')WR$^{7a}$;

R$^8$ is hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —(CH$_2$)$_{0-3}$(NR$^{8c}$)$_{0-1}$C(=E')ER$^{8a}$;

R$^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH$_2$)$_{0-3}$NR$^{9c}$C(=Z')ZR$^{9a}$;

R$^{7a}$, R$^{7b}$, R$^{7c}$, R$^{7d}$, R$^{7e}$, R$^{7f}$, R$^{8a}$, R$^{8b}$, R$^{8c}$, R$^{8d}$, R$^{8e}$, R$^{8f}$, R$^{9a}$, R$^{9b}$, R$^{9c}$, R$^{9d}$, R$^{9e}$, and R$^{8f}$ are each independently absent, hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

E is CR$^{8d}$R$^{8e}$, S, NR$^{8b}$ or O;

E' is O, NR$^{8f}$, or S;

W is CR$^{7d}$R$^{7e}$, S, O or NR$^{7b}$;

W' is O, NR$^{7f}$, or S;

R$^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

In another further embodiment, the invention pertains, at least in part, to methods for treating subjects for tetracycline responsive states by administering to them an effective amount of a tetracycline compound of the invention, e.g., a compound of formula I, II, III, IV, or a tetracycline compound otherwise described herein.

DETAILED DESCRIPTION OF THE INVENTION

The present invention pertains, at least in part, to novel substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

The term "tetracycline compound" includes many compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

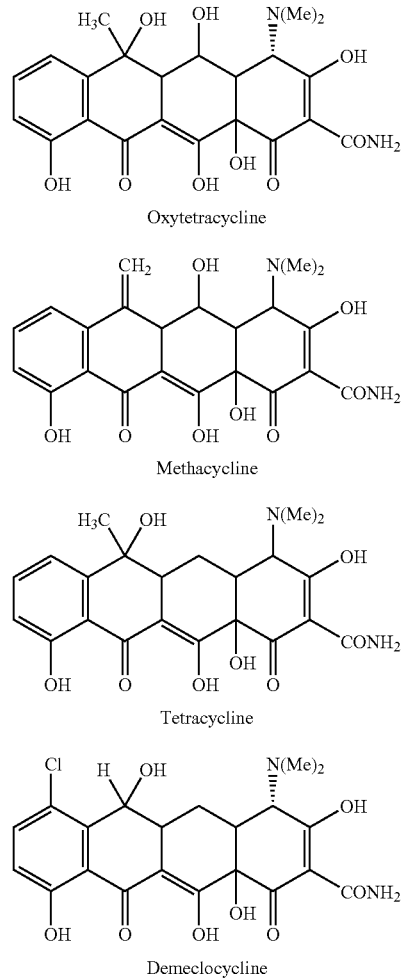

Oxytetracycline

Methacycline

Tetracycline

Demeclocycline

TABLE 1-continued

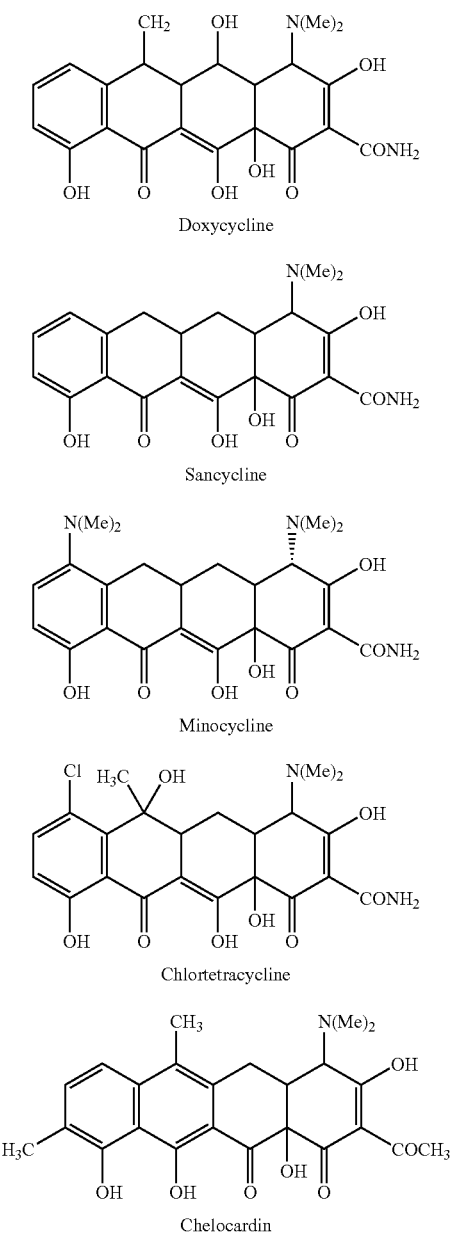

Doxycycline

Sancycline

Minocycline

Chlortetracycline

Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a Cl-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a, 6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a Cl-6, 12 hemiketal tetracyclines; 11a Cl-6-methylene tetracyclines; 6,13 diol tetracyclines; 6-benzylthiomethylene tetracyclines; 7,11a-dichloro-6-fluoro-methyl-6-deoxy tetracyclines; 6-fluoro(α)-6-demethyl-6-deoxy tetracyclines; 6-fluoro(β)-6-demethyl-6-deoxy tetracyclines; 6-αacetoxy-6-demethyl tetracyclines; 6-β acetoxy-6-demethyl tetracyclines; 7,13-epithiotetracyclines; oxytetracyclines; pyrazolotetracyclines; 11a halogens of tetracyclines; 12a formyl and other esters of tetracyclines; 5, 12a esters of tetracyclines; 10,12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

I. 7-Substituted Tetracycline Compounds

In one embodiment, the invention pertains to novel 7-substituted tetracycline compounds.

The term "7-substituted tetracycline compounds" includes tetracycline compounds with substitution at the 7 position. In one embodiment, the substitution at the 7-position enhances the ability of the tetracycline compound to perform its intended function, e.g., treat tetracycline responsive states. In an embodiment, the 7-substituted tetracycline compound is 7-substituted tetracycline (e.g., wherein $R^4$ is $NR^{4'}R^{4''}$, $R^{4'}$ and $R^{4''}$ are methyl, $R^5$ is hydrogen and X is $CR^6R^{6'}$, wherein $R^6$ is methyl and $R^{6'}$ is hydroxy); 7-substituted doxycycline (e.g., wherein $R^4$ is $NR^{4'}R^{4''}$, $R^{4'}$ and $R^{4''}$ are methyl, $R^5$ is hydroxyl and X is $CR^6R^{6'}$, wherein $R^6$ is methyl and $R^{6'}$ is hydrogen); 7-substituted tetracycline compound, wherein X is $CR^6R^{6'}$, $R^4$, $R^5$, $R^6$, and $R^6$ are hydrogen; or 7-substituted sancycline (wherein $R^4$ is $NR^{4'}R^{4''}$, $R^{4'}$ and $R^{4''}$ are methyl; $R^5$ is hydrogen and X is $CR^6R^{6'}$ wherein $R^6$ and $R^{6'}$ are hydrogen atoms.

The invention pertains, at least in part, to 7-substituted tetracycline compound of Formula I:

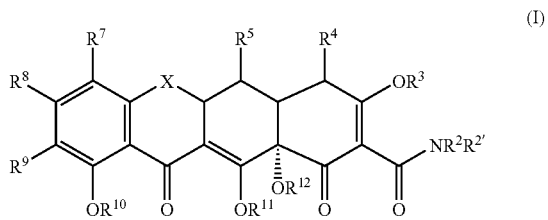

(I)

wherein:

X is $CHC(R^{13}Y'Y)$, $CR^6R^6$, $C=CR^6R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, hetero aromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is boronic acid moiety, isoxazolyl, sulfonic acid heterocyclic, carbonyl, alkylsulfinyl, alkylsulfonyl, arylalkenyl, arylalkynyl, or $-(CH_2)_{0-3}NR^{7c}C(=W')WR^{7a}$;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso (e.g., $-N=S$), or $-(CH_2)_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$ S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In certain embodiment, $R^7$ is not nitro or amino.

In an embodiment, X is $CR^6R^{6'}$; $R^2$, $R^{2'}$, $R^6$, $R^{6'}$, $R^8$, $R^9$, $R^{10}$, $R^{11}$, and $R^{12}$ are each hydrogen; $R^4$ is $NR^{4'}R^{4''}$; $R^{4'}$ and $R^{4''}$ are lower alkyl (e.g., methyl); and $R^5$ is hydroxy or hydrogen.

In a further embodiment, $R^{7f}$ is hydrogen or alkyl. In another embodiment, $R^{7g}$ is alkyl, heterocyclic, or aralkyl, e.g., benzyl.

In certain embodiments, $R^{7g}$ and $R^{7f}$ are linked to form a ring. $R^{7g}$ and $R^{7f}$ can be linked with a chain to form rings of 3-8 atoms, such as carbon (e.g., to form a piperidinyl ring), oxygen (e.g, morpholinyl, etc.), nitrogen (e.g., pyrazinyl, piperazinyl, etc.).

In another embodiment, $R^7$ is furanyl. In a further embodiment, the furan is substituted with a substituted or unsubstituted alkyl group, which itself may be substituted by one or more heterocyclic groups.

In another further embodiment, $R^7$ is a non-aromatic heterocycle. In a further embodiment, the heterocyclic $R^7$ group does not contain any double bonds, e.g. the heterocyclic $R^7$ group is saturated. Examples of saturated heterocyclic $R^7$ groups include but are not limited to, morpholine, piperazine, piperidine, etc.

In another further embodiment, $R^7$ comprises a carbonyl group. For example, in a further embodiment, $R^7$ is of the formula $-(C=O)-R^{7j}$, wherein $R^{7j}$ is alkcarbonyl, alkyl, alkenyl, alkynyl, aryl, heterocyclic or aralkyl. In a further embodiment, $R^{7j}$ is substituted or unsubstituted alkyl. In another embodiment, the alkyl $R^{7j}$ group is substituted with a heterocycle, such as, but not limited to morpholine, piperidine, or piperazine.

In embodiment, $R^7$ is aryl. Examples of aryl $R^7$ groups include substituted or unsubstituted phenyl. The phenyl $R^7$ group can be substituted with any substituent which allow the tetracycline compound to perform its intended function. Examples of substituents include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, $R^7$ is phenyl substituted with a sulfonyl amino or alkylcarbonylamino group.

In a further embodiment, the phenyl $R^7$ group is substituted with substituted or unsubstituted alkyl. Examples of substituents of the alkyl include heterocycles such as, morpholine, piperidine, and pyrrolidine. In another further embodiment, the phenyl $R^7$ group is substituted with an amino group. The amino group also may be further substituted e.g., with an alkyl, alkenyl, alkynyl, carbonyl, alkoxy or aryl (e.g., substituted or unsubstituted, heteroaryl, phenyl, etc.) group. The phenyl amino substituent may be substituted with any substituent or combination of substituents which allow it to perform its intended function. Examples of such substituents include halogens (e.g., fluorine, chlorine, bromine, iodine, etc.), amino (e.g., which can in turn be substituted with an alkyl, carbonyl, alkenyl, alkynyl, or aryl moiety), and arylamino (e.g., phenylamino).

The $R^7$ phenyl group may also be substituted with alkoxy groups. Examples of alkoxy groups include, but are not limited to, methoxy, ethoxy, propoxy, butoxy, perfluoromethoxy, perchloromethoxy, methylenedioxy, etc. The phenyl group may also be substituted with an amide group such as a carbamate moiety (e.g., an alkoxycarbonylamino group).

The aryl group $R^7$ group also may be substituted or unsubstituted biaryl, e.g., naphthyl, fluorenyl, etc. The biaryl $R^7$ group can be substituted with any substituent which allow it to perform its intended function. Examples of substituents include but are not limited to, alkyl, alkenyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In an embodiment, the substituent is amino or formyl.

The aryl $R^7$ group also may be heteroaryl. Examples of heteroaryl $R^7$ moieties include, but are not limited to, furanyl, imidazolyl, benzothiophenyl, benzofuranyl, quinolinyl, isoquinolinyl, pyridinyl, pyrazolyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, and deazapurinyl. In certain embodiments, the heteroaryl $R^7$ group is thiazolyl, thiophenyl, or furanyl.

$R^7$ also may be substituted or unsubstituted alkyl. The alkyl group can be a straight or branched chain, e.g., methyl, ethyl, i-propyl, n-propyl, n-butyl, i-butyl, t-butyl, pentyl, hexyl. etc. The alkyl group may also comprise a ring, e.g., a cycloalkyl (e.g., cyclopentyl, cyclohexyl, cyclopropyl, or cyclobutyl). The alkyl $R^7$ group may be substituted with any substituent or combination of substituents which allows the compound to perform its intended function. Examples of substituents include, but are not limited to, alkenyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In certain embodiments, the alkyl group is substituted with an amino, hydroxy, carboxy, carbonyl (e.g., substituted carbonyl, e.g., morpholinyl carbonyl), heterocyclic or aryl groups. Examples heterocyclic groups include, for example, furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyridinyl, pyrazolyl, pyrimidyl, pyrazinyl, purinyl, pyrazolyl, oxazolyl, isooxazolyl, naphthridinyl, thiazolyl, isothiazolyl, and deazapurinyl. In a further embodiment, the aryl group is pyridinyl.

In a further embodiment, the aralkyl $R^7$ group comprises substituted or unsubstituted phenyl. This phenyl group also may be substituted with any substituent which allows it to perform its intended function. Examples of substituents include, but are not limited to, sulfonamido, alkyl, and the other substituents listed supra for alkyl $R^7$ groups.

$R^7$ also may be substituted or unsubstituted alkenyl. Examples of substituents include those which allow the compound to perform its intended function. Examples of substituents include but are not limited to alkyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl moieties.

In a further embodiment, the alkenyl $R^7$ group is substituted with an aminocarbonyl (e.g., alkylaminocarbonyl, dialkylaminocarbonyl, dimethylaminocarbonyl) or alkoxycarbonyl. The alkenyl $R^7$ group also may be substituted with one or more halogens (e.g., fluorine, chlorine, bromine, iodine, etc.), hydroxy groups, heteroaryl groups (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyridinyl, pyrazolyl, pyrimidyl, pyrazinyl, purinyl, pyrazolyl, oxazolyl, isooxazolyl, naphthridinyl, thiazolyl, isothiazolyl, deazapurinyl, etc.). In an embodiment, the heteroaryl substituent s thiazolyl.

In a further embodiment, the alkenyl $R^7$ group is substituted with a substituted or unsubstituted phenyl. The phenyl can be substituted with any substituent which allows it to perform its intended function. Examples of substituents include those listed supra for other phenyl moieties. Other examples of substituents include, but are not limited to, halogens (e.g., fluorine, chlorine, bromine, iodine, etc.), alkoxy (e.g., methoxy, ethoxy, propoxy, perfluoromethyl, perchloromethyl, etc.), hydroxy, or alkyl (e.g., methyl, ethyl, propyl, butyl, pentyl, hexyl, etc.) groups.

Another example of $R^7$ include substituted and unsubstituted alkynyls. The alkynyl moieties can be substituted with any substituent or combination of substituents which allow the tetracycline compound of the invention to perform its intended function. Examples of the substituents include, but are not limited to alkyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl moieties.

In an embodiment, the alkynyl $R^7$ moiety is substituted with an aryl, e.g., substituted or unsubstituted heteroaryl, phenyl, etc. This aryl moiety may be substituted with any substituent or combinations of substituents listed supra for the alkynyl $R^7$ moiety. Examples of advantageous substituents include, but are not limited to, carbonylamino (e.g., alkylcarbonylamino, dialkylcarbonylamino, arylcarbonylamino, etc.) and sulphonamido groups.

In another embodiment, the alkynyl $R^7$ group is substituted with a tetracycline moiety. The term "tetracycline moiety" includes a four ring tetracycline ring system as described above. This may be connected to the alkynyl $R^7$ group through a linker of 1-20 atoms. The linker may be attached to the tetracycline moiety at any position on that ring system which is convenient or allows the compound to perform its intended function. In a certain embodiment, the tetracycline moiety is attached to the linker at its 7 position.

Other examples of $R^7$ moieties include substituted and unsubstituted alkylcarbonyl amino, sulfonamido, imino and carbonyl moieties. The carbonyl moieties may be substituted with a substituted or unsubstituted alkyl group. Examples of possible substituents of the alkyl group include, but are not limited to, aryl moieties such as phenyl and heteroaryls (e.g., pyridinyl, etc.). Examples of substituents of the imino group include, but are not limited to, hydroxy and alkoxy groups.

In another embodiment, $R^7$ is $NR^{7c}(C=W')WR^{7a}$. Examples of tetracycline compounds of the invention include compounds wherein $R^{7c}$ is hydrogen, W' is oxygen and W is oxygen. In certain embodiments, $R^{7a}$ is substituted or unsubstituted phenyl. Examples of substituents include, but are not limited to, alkyl, halogen, hydroxyl, alkoxy, alkylcarbonyloxy, alkyloxycarbonyl, carboxy, alkylcarbonylamino, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In a further embodiment, $R^{7a}$ is substituted or unsubstituted alkyl.

In a further embodiment, $R^4$ is $NR^{4'}R^{4''}$, X is $CR^6R^{6'}$; $R^2$, $R^{2'}$, $R^6$, $R^{6'}$, $R^8$, $R^9$, $R^{10}$, $R^{11}$, and $R^{12}$ are each hydrogen; $R^{4'}$ and $R^{4''}$ are lower alkyl; and $R^5$ is hydroxy or hydrogen. $R^{4'}$ and $R^{4''}$ may be methyl, for example, and $R^5$ may be hydrogen.

In a further embodiment, $R^7$ is a substituted pyrolle. The pyrolle may be substituted with a carbonyl moiety, such as, for example substituted or unsubstituted alkoxycarbonyl.

In another embodiment, $R^7$ is a substituted pyrazine. Examples of substitutents include substituted or unsubstituted alkoxycarbonylamino groups, an alkaminocarbonylamino groups, and alkylaminocarbonyl groups.

In another embodiment, $R^7$ is substituted pyridine. Examples of substituents include halogens. In another embodiment, $R^7$ is alkenyl and substituted with a halogen (e.g., fluorine), or a carbonyl group. In another embodiment $R^7$ is pyrazolyl.

In another embodiment, $R^7$ is $—C(=W')WR^{7a}$, and W' is $NR^{7f}$, W is $CR^{7d}R^{7e}$, and $R^{7a}$ is hydrogen. In a further embodiment, $R^{7f}$ is alkoxy.

In yet another embodiment, $R^7$ is $—NR^{7c}C(=W')WR^{7a}$, $R^{7c}$ is hydrogen, W' is NH, W is $NR^{7b}$, and $R^{7a}$ and $R^{7b}$ taken together are heterocyclic, e.g., pyrollidine.

In another embodiment, $R^7$ is a boronic acid. Examples of boronic acids include compounds wherein $R^7$ is $—B(OR^{b1})(OR^{b2})$ and $R^{b1}$ and $R^{b2}$ are each hydrogen or alkyl, and optionally linked to form a ring.

In another embodiment, $R^7$ is a sulfonic acid, or an ester or prodrug thereof. Examples of sulfonic acids include $—SO_3H$.

In yet another embodiment, $R^7$ is isoxazolyl. $R^7$ may be substituted or unsubstituted. In one embodiment, the isooxazole is substituted with, for example, alkyl groups.

Other examples of tetracycline compounds include the following:

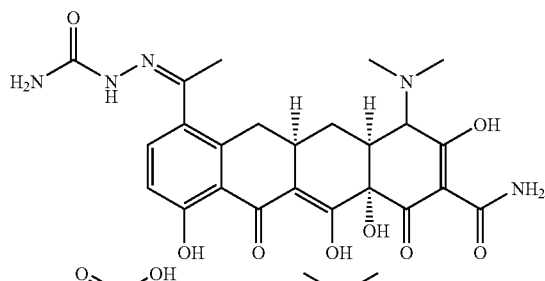

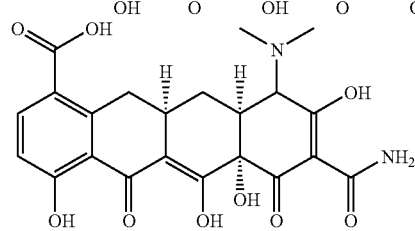

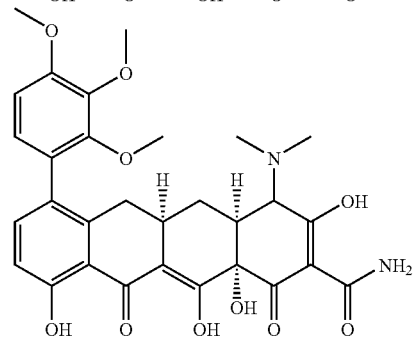

-continued

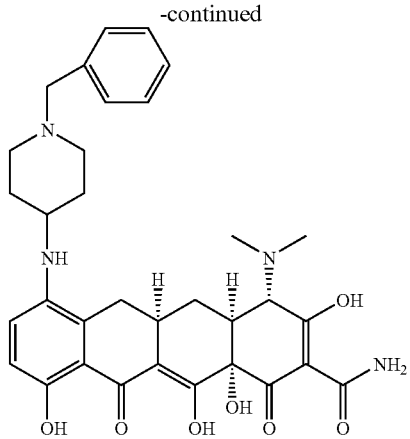

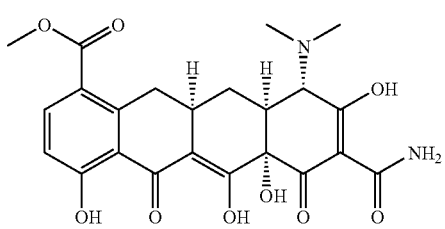

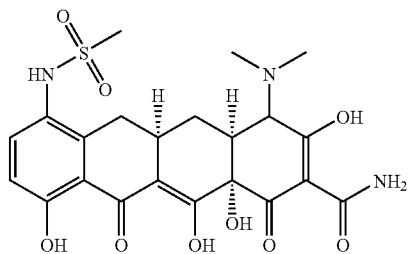

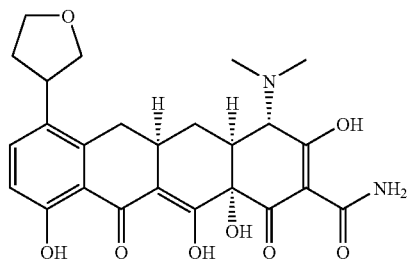

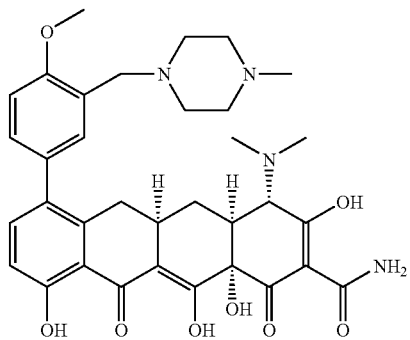

-continued
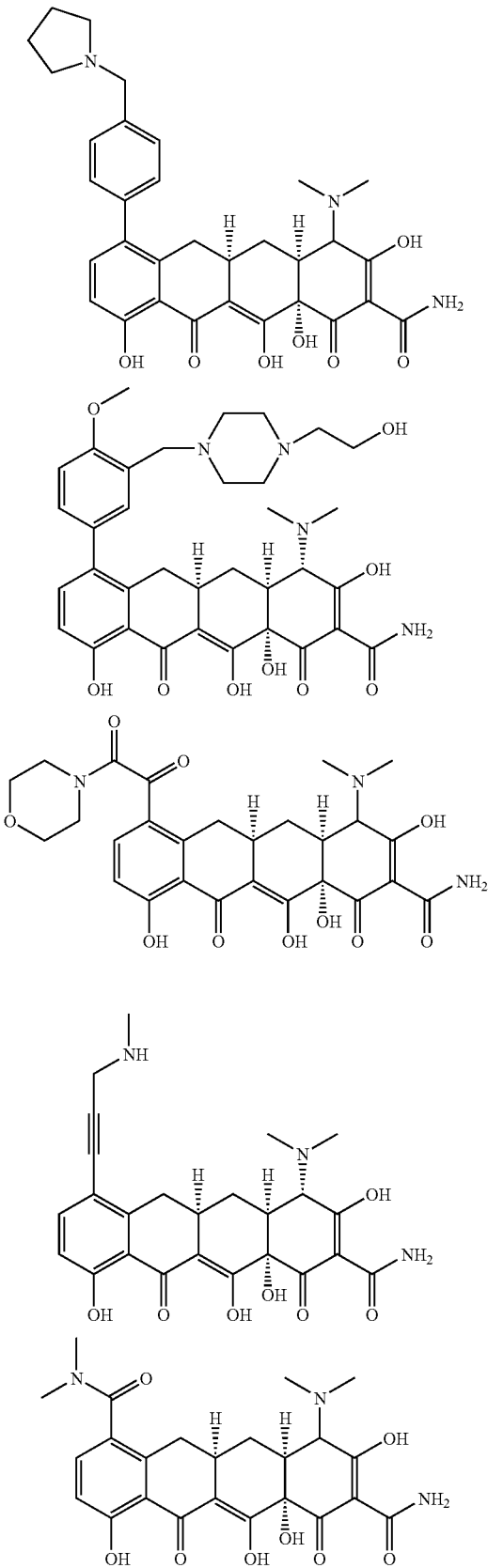
-continued
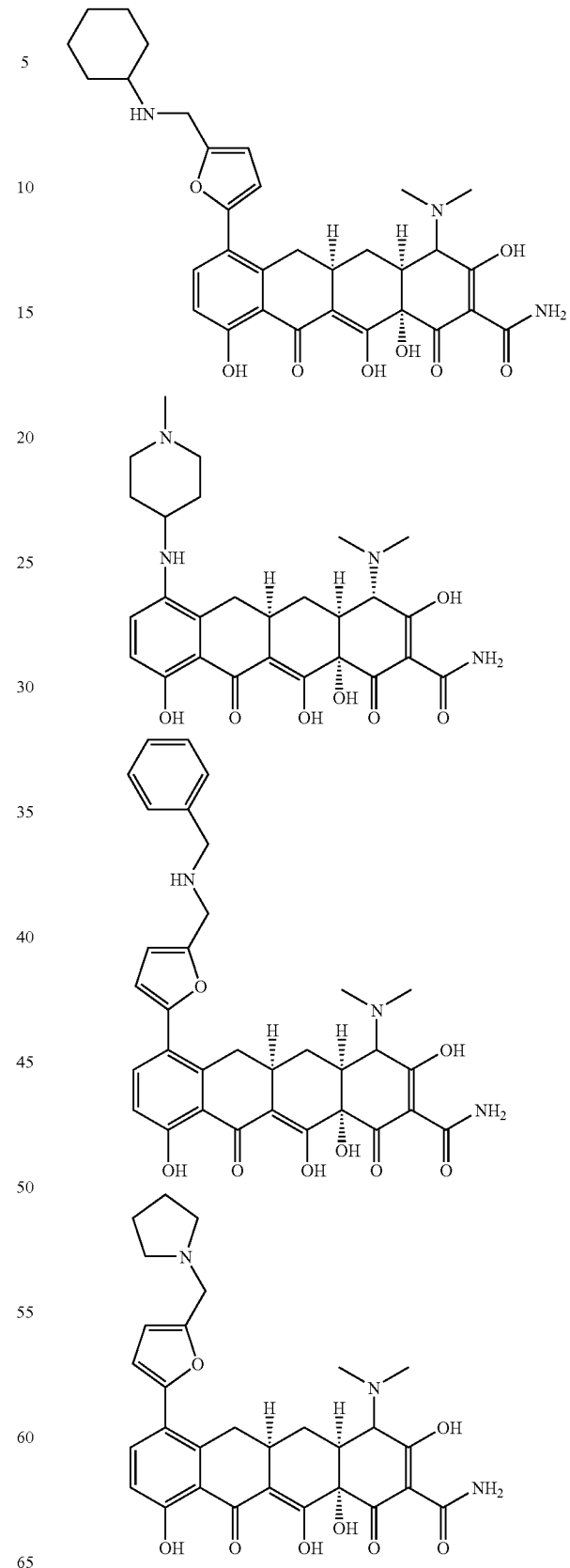

-continued
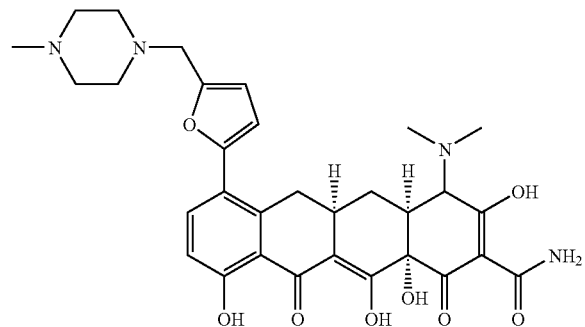
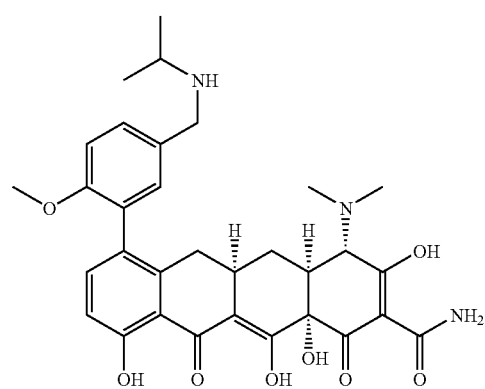
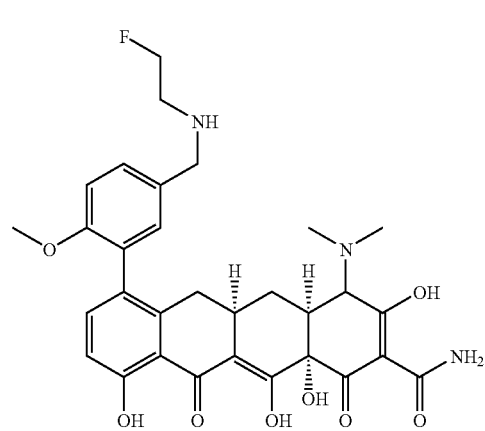
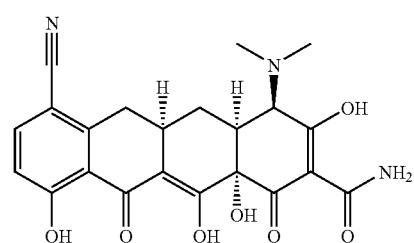
-continued
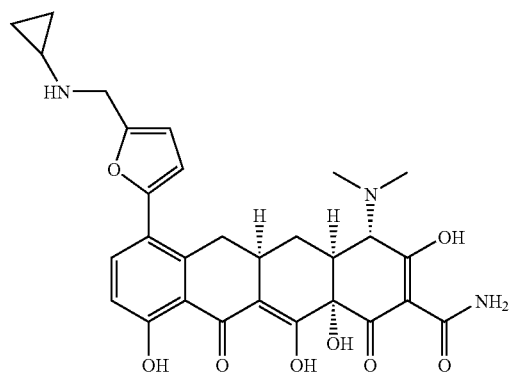
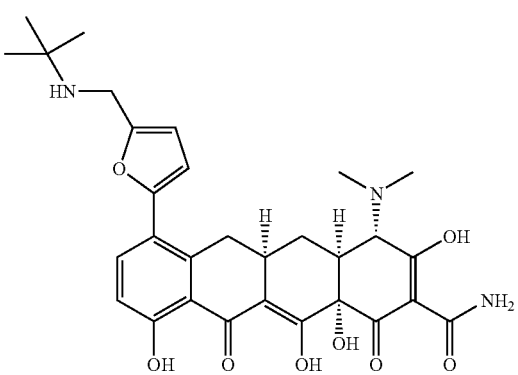
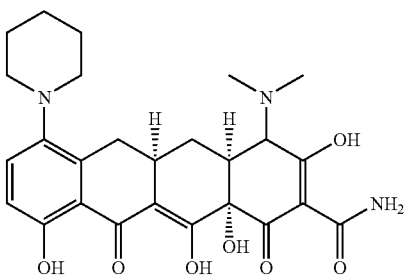
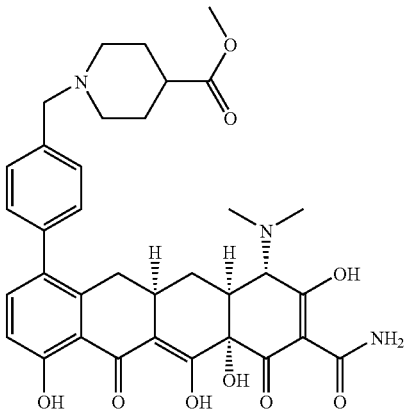

-continued
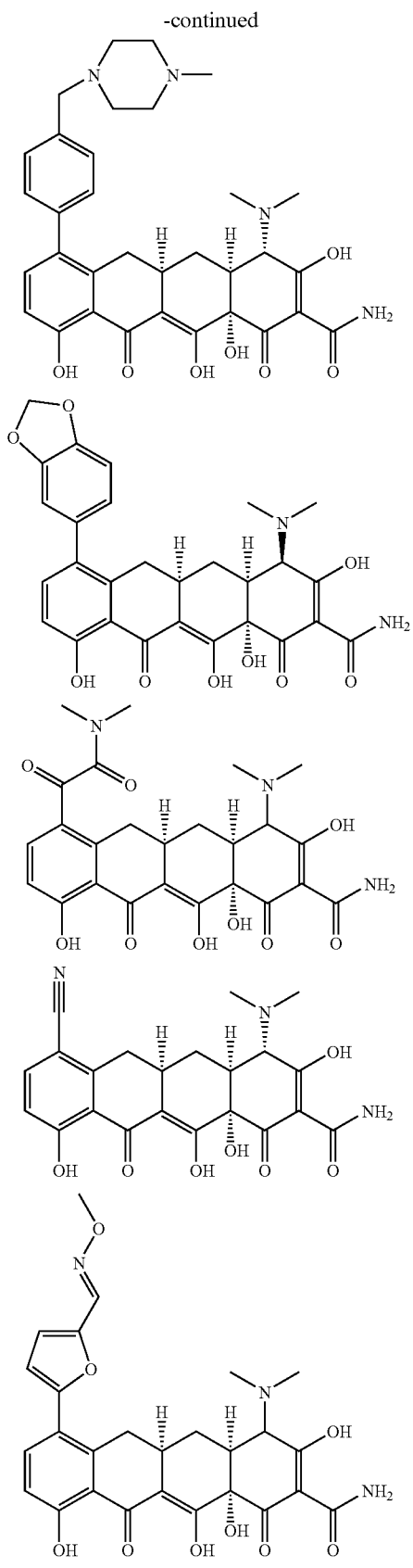
-continued
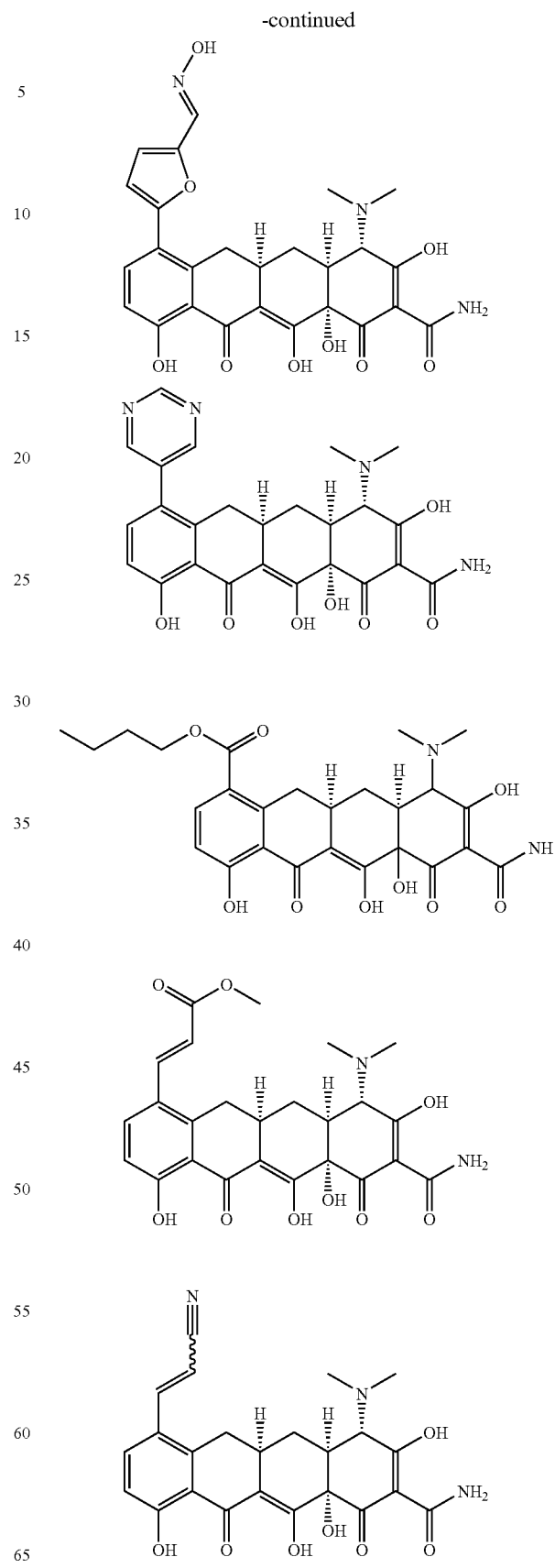

-continued
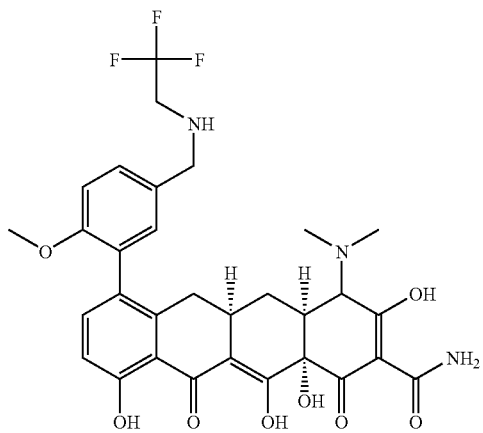
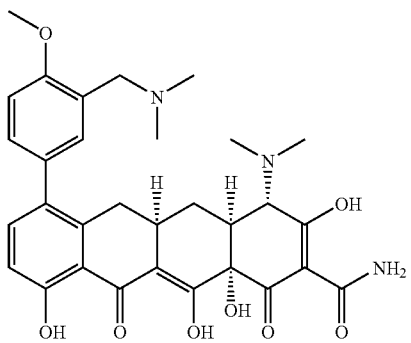
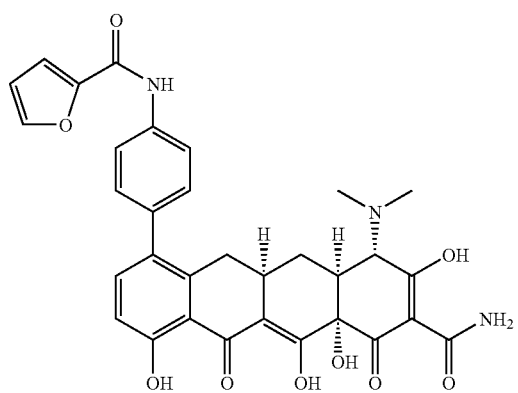
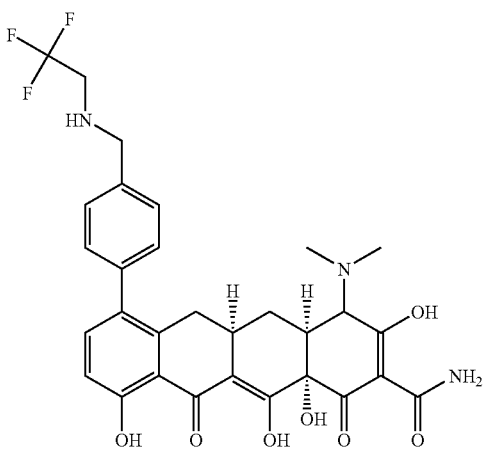
-continued
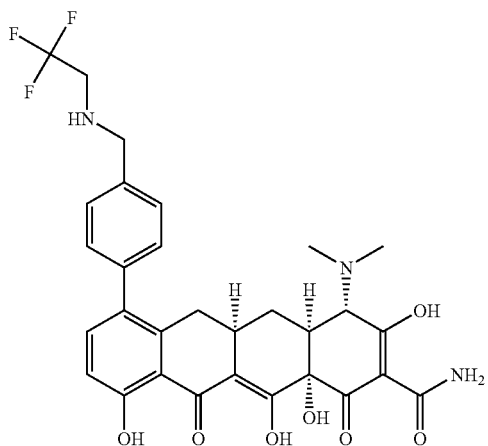
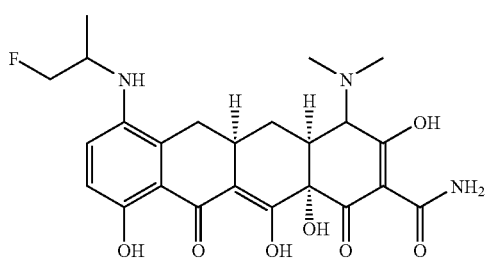
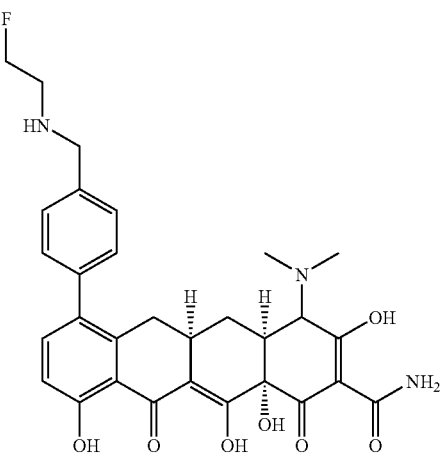
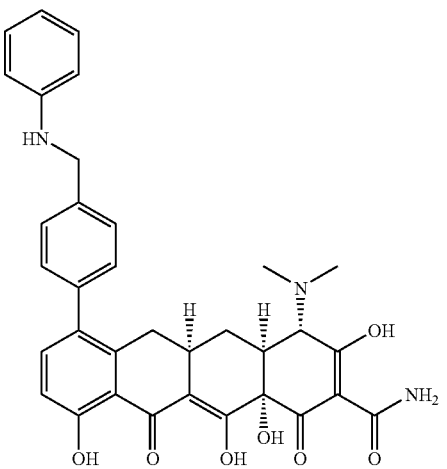

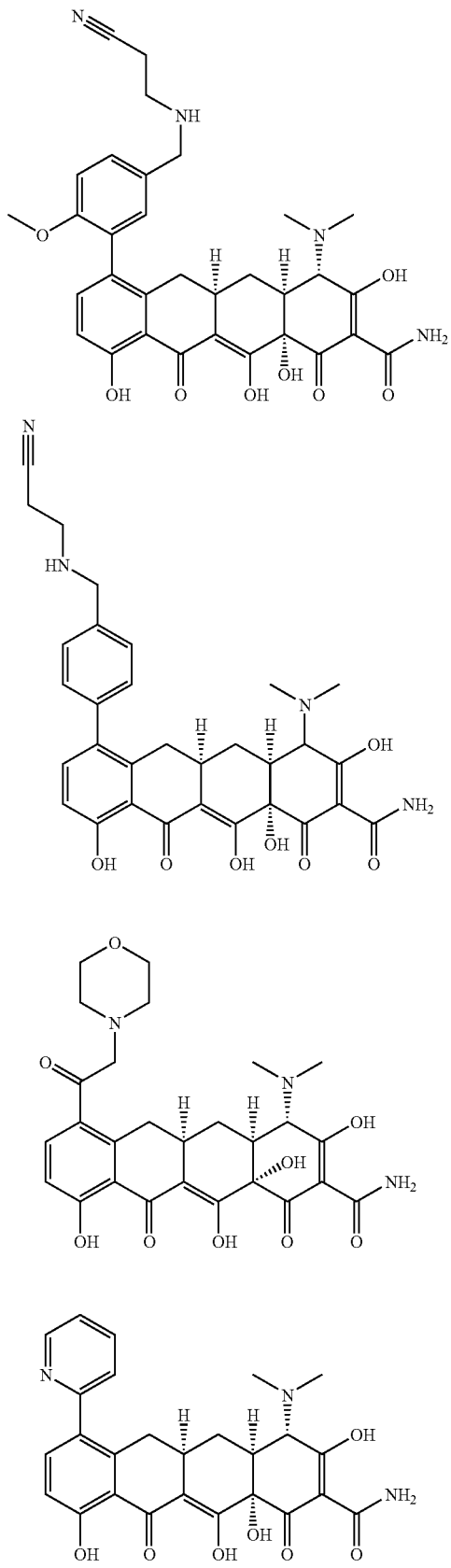
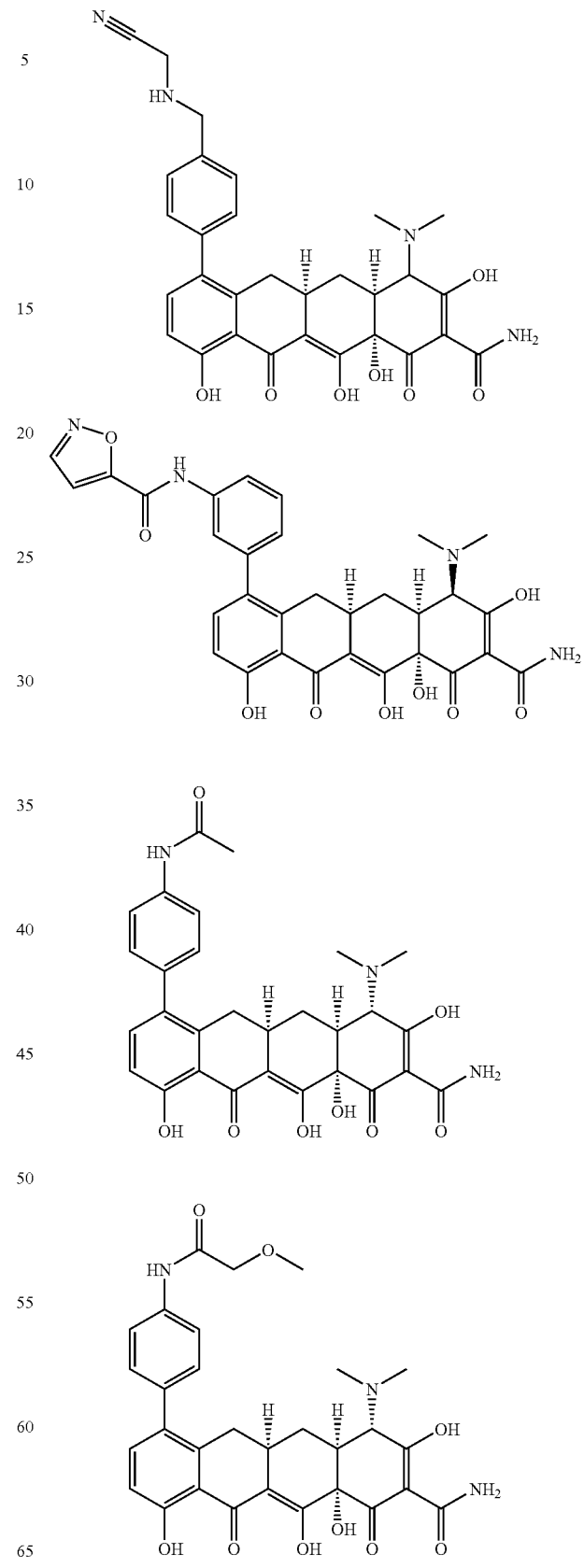

-continued
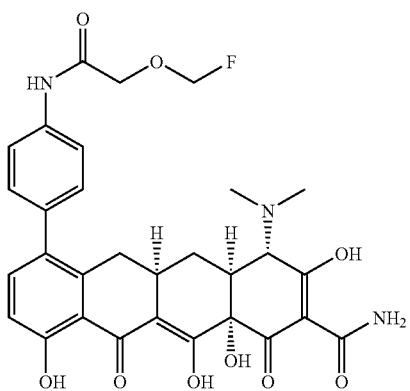
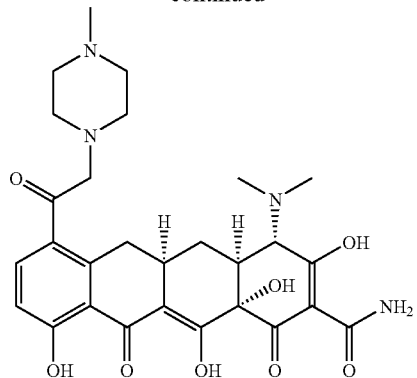
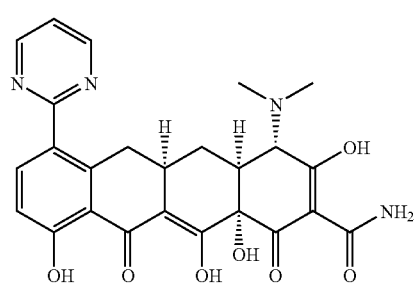
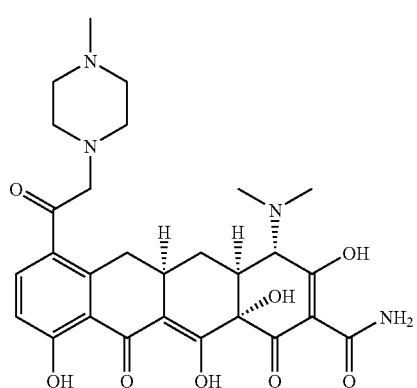
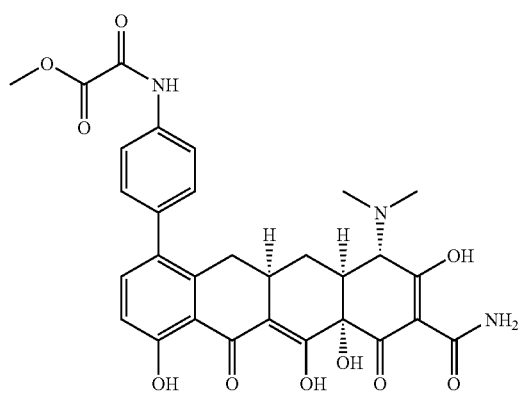
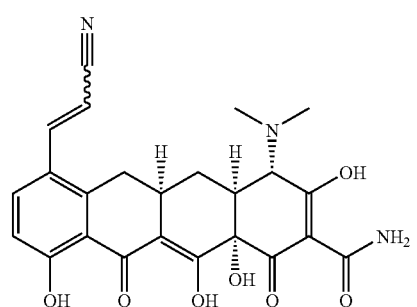
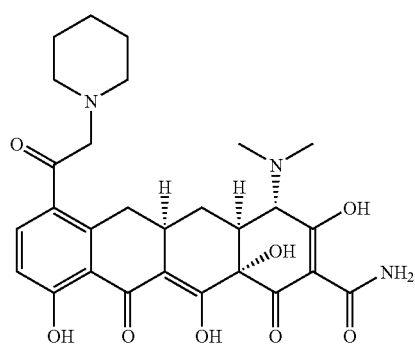
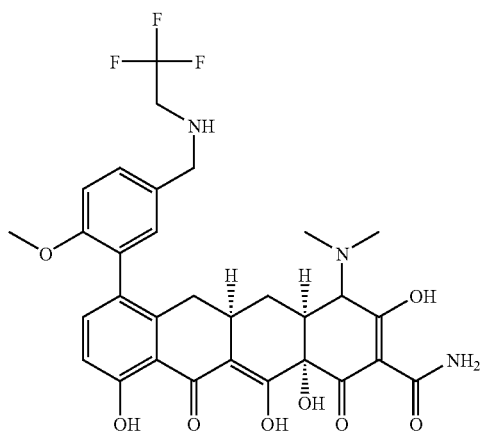

-continued
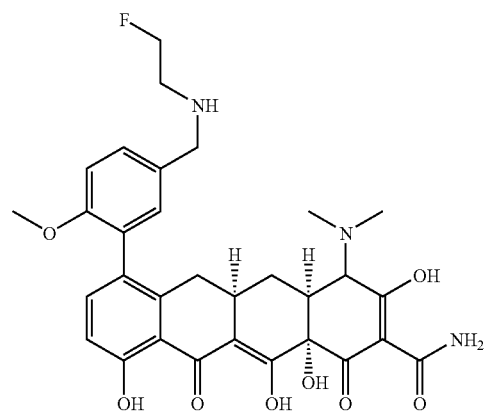
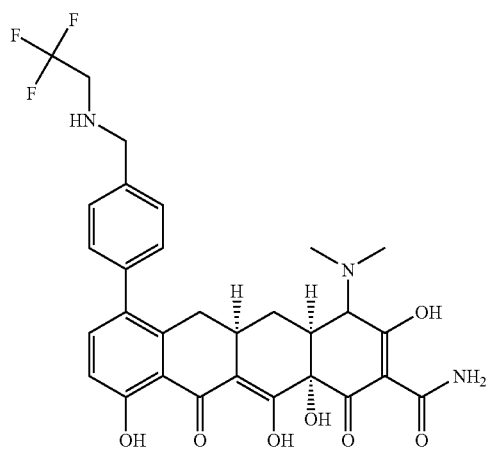
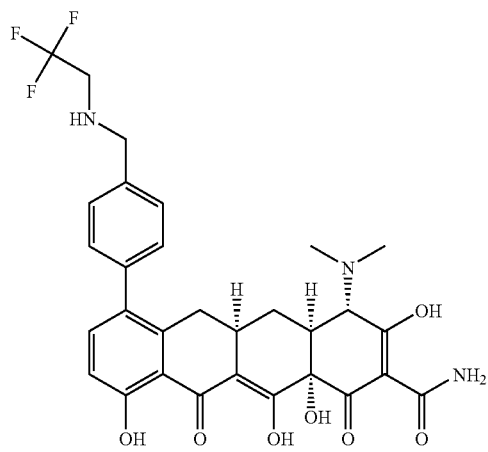
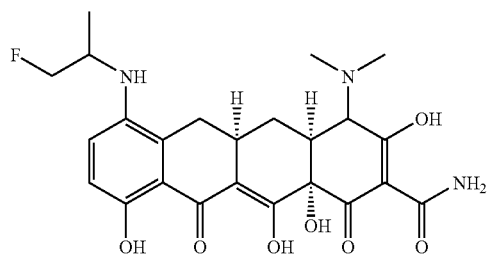
-continued
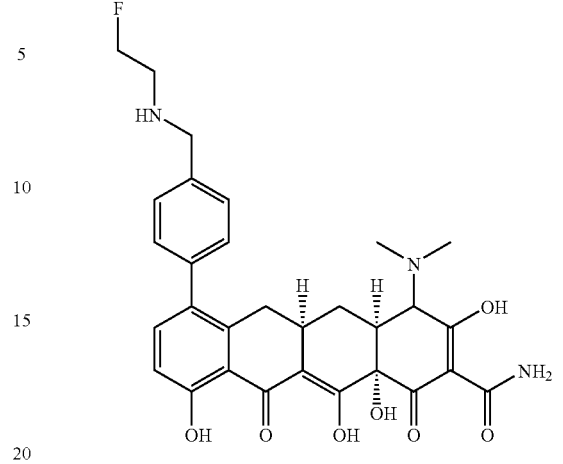
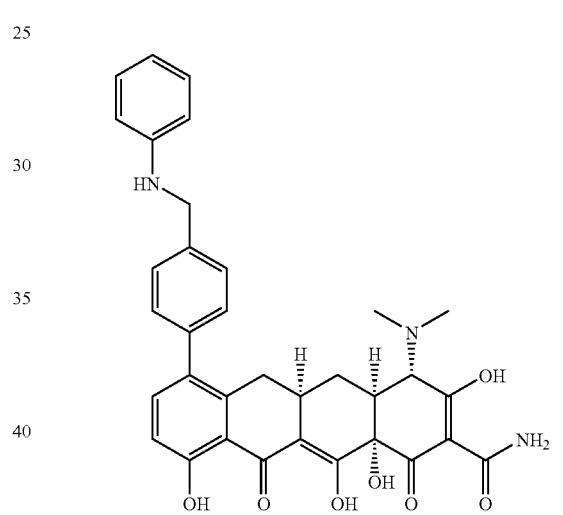
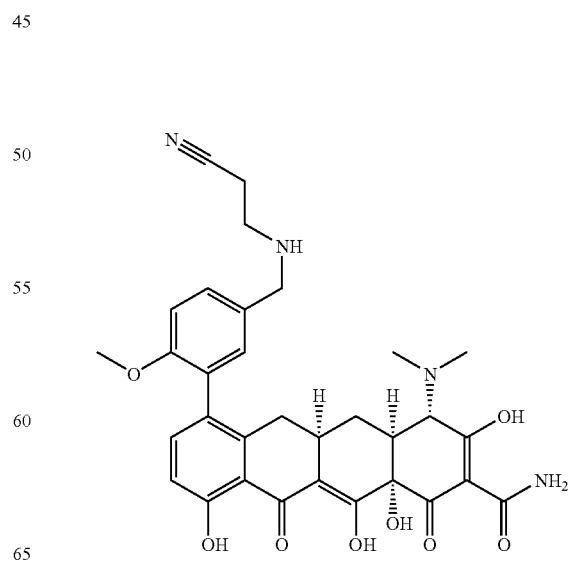

-continued
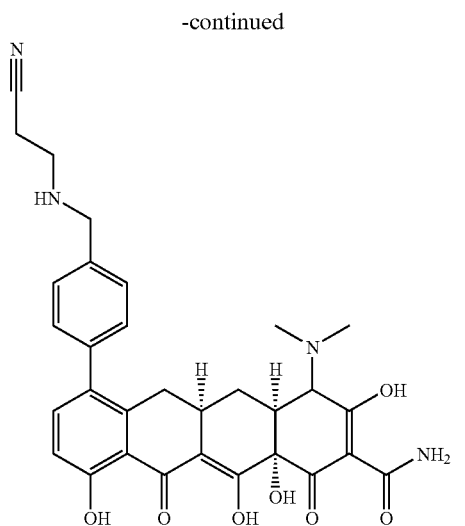
-continued
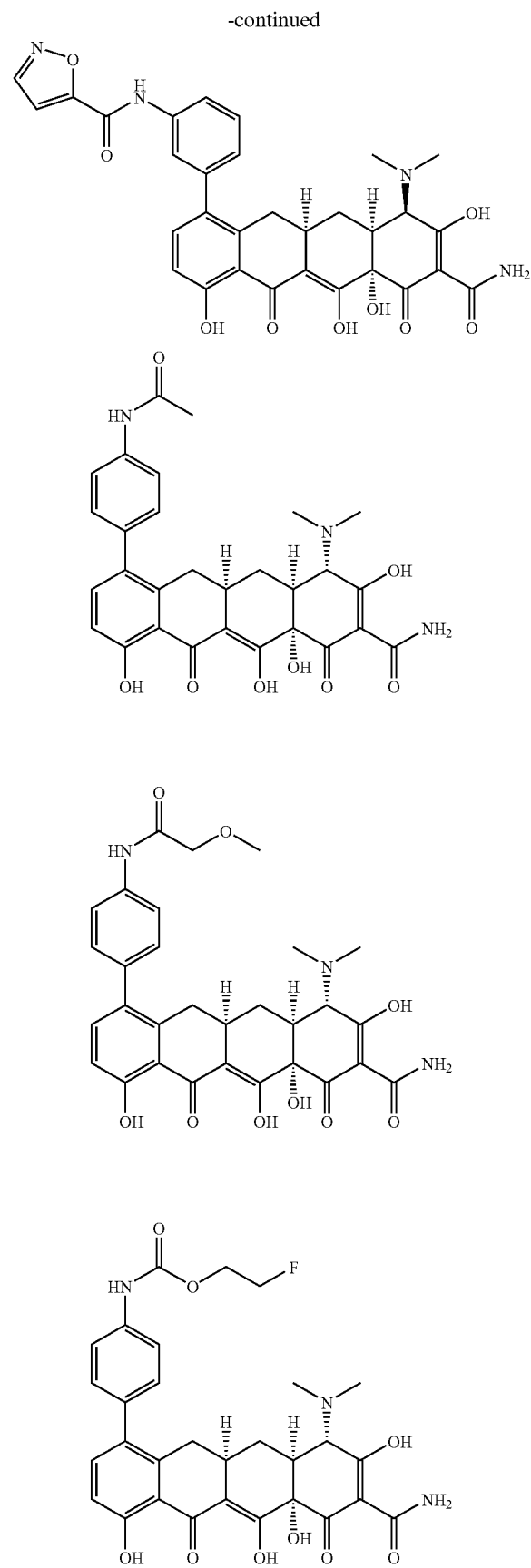

-continued
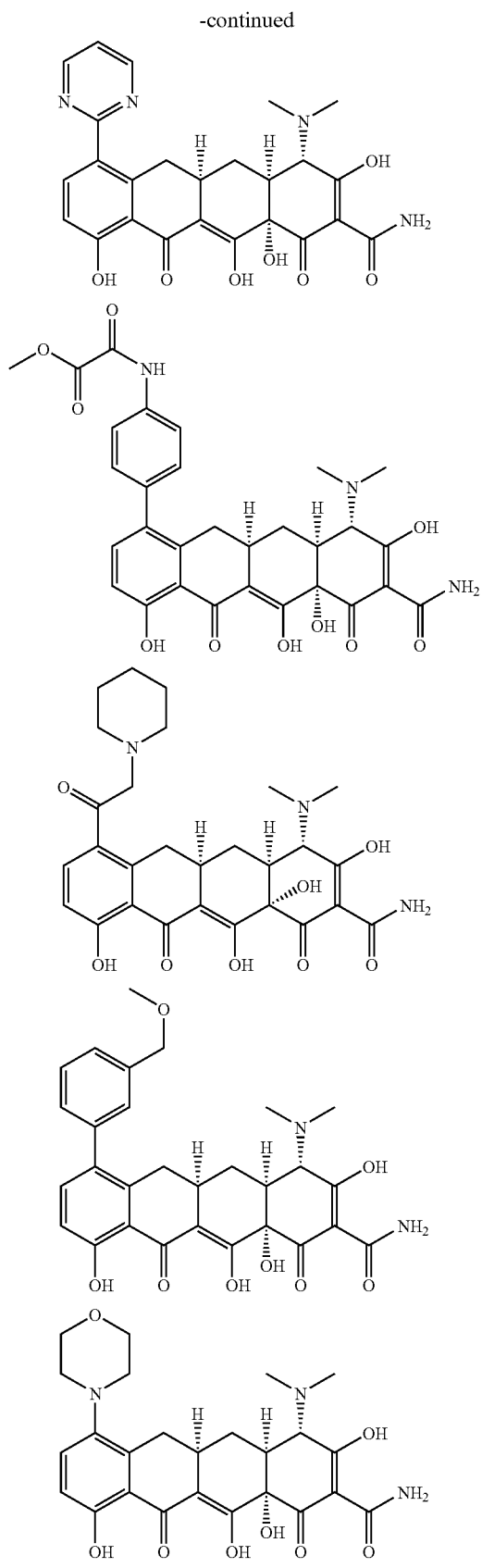
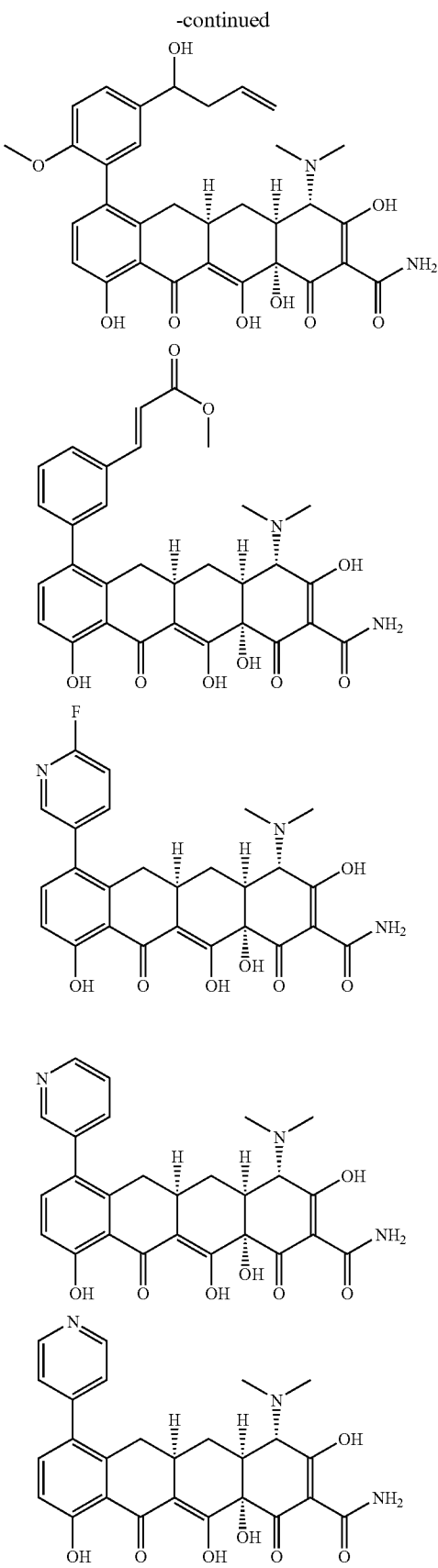

33
-continued
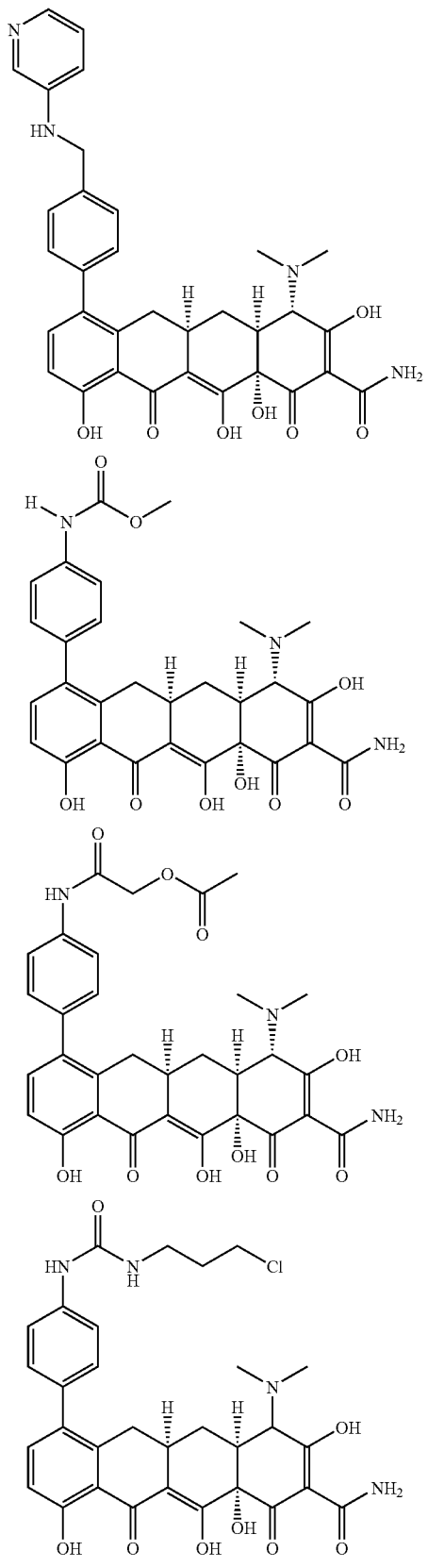
34
-continued
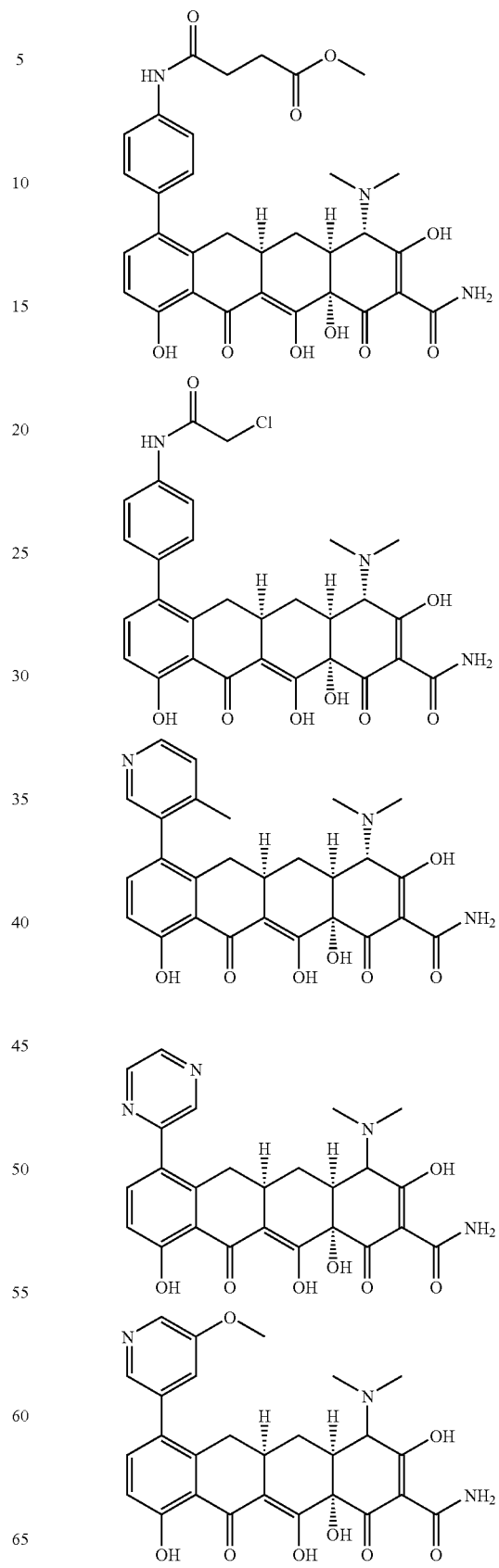

-continued
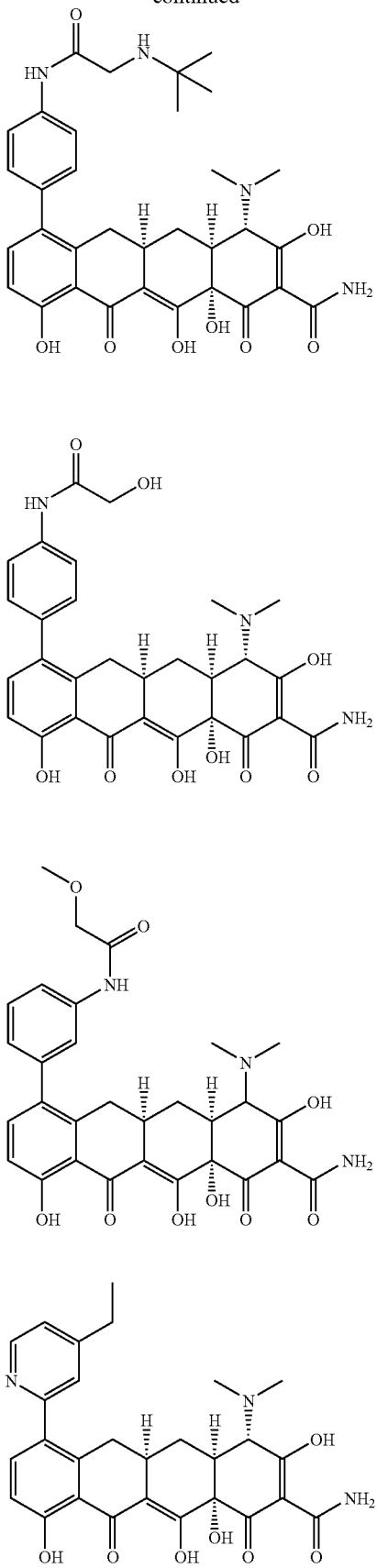
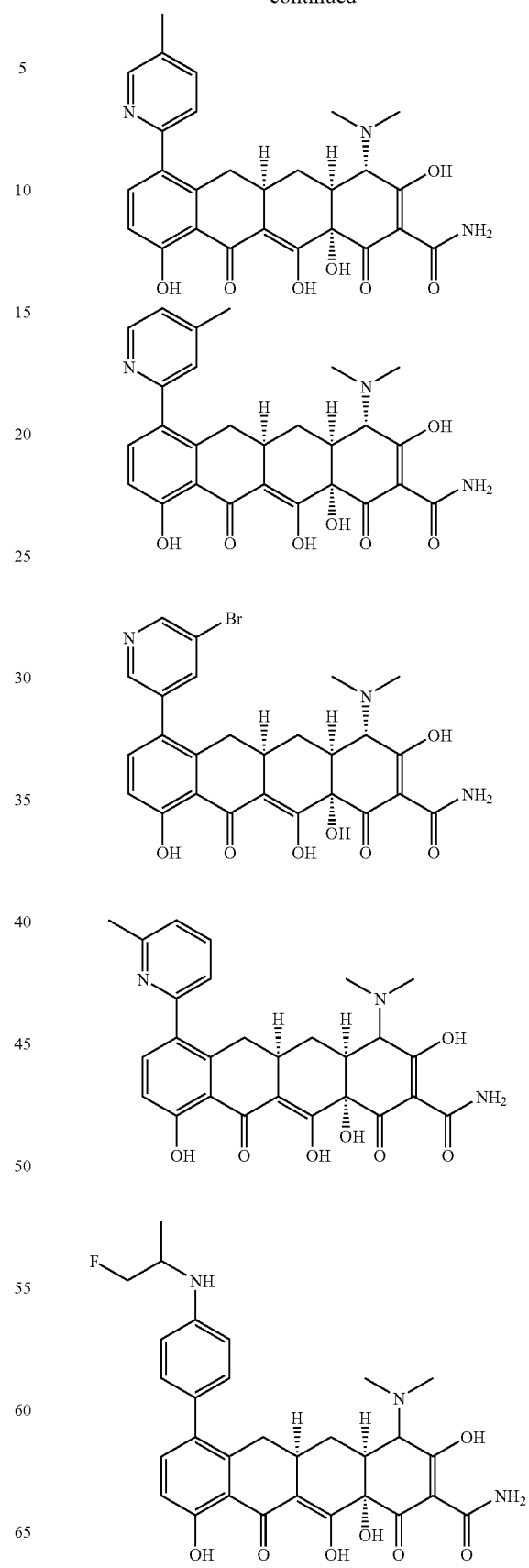

-continued
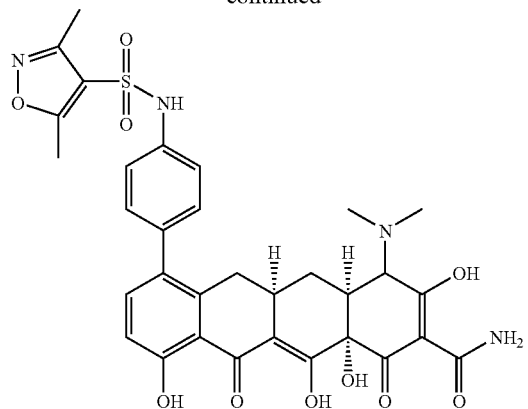
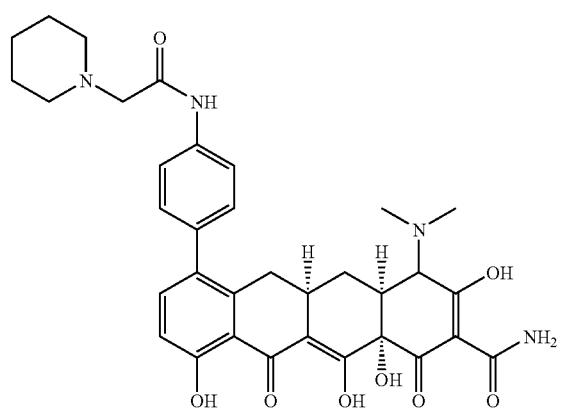
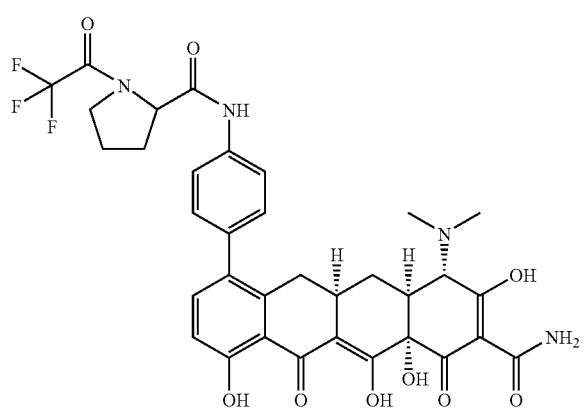
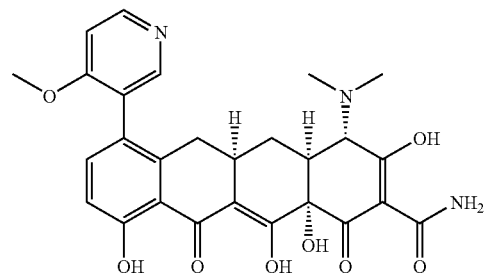
-continued
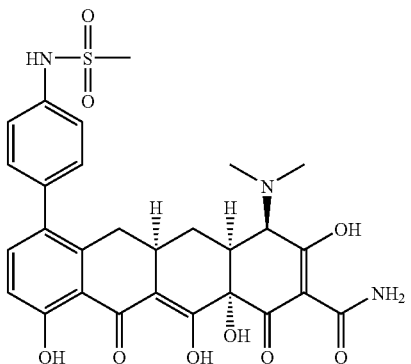
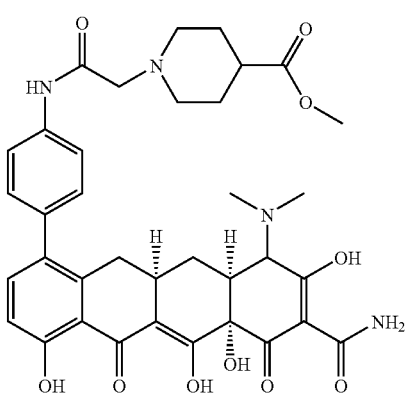
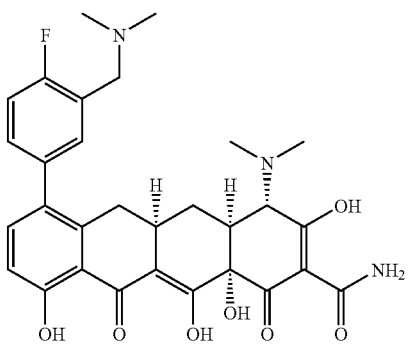
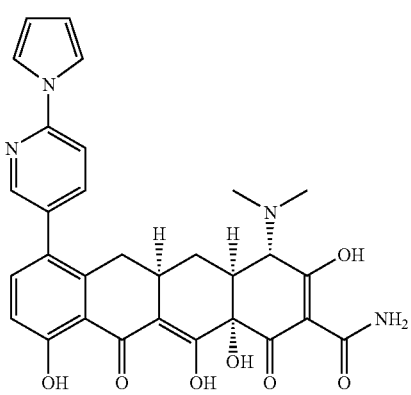

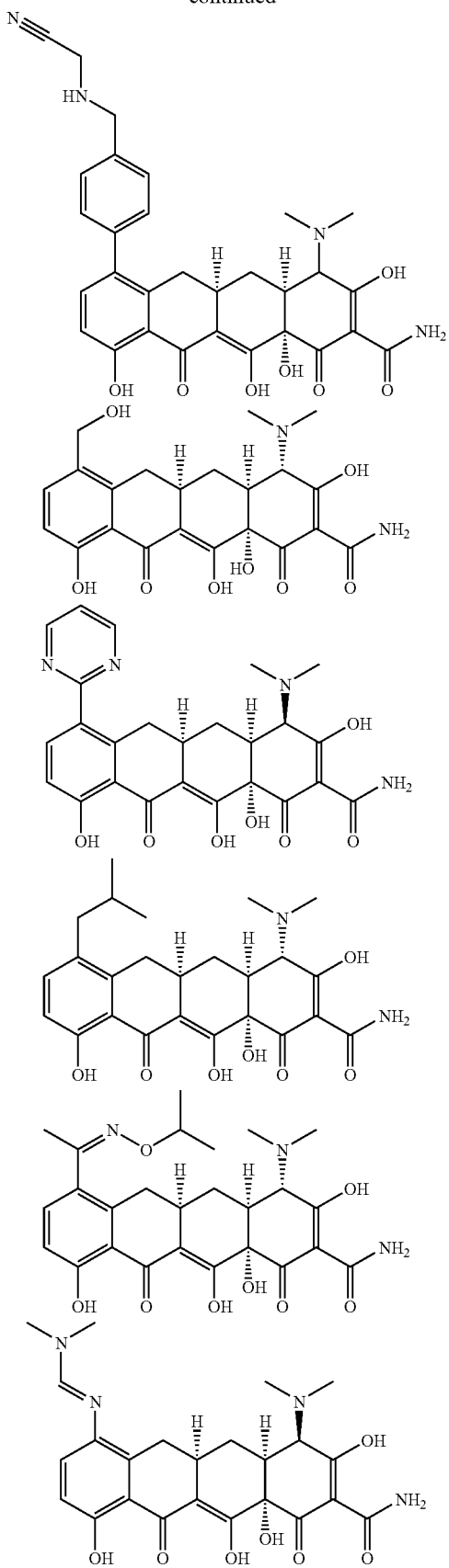
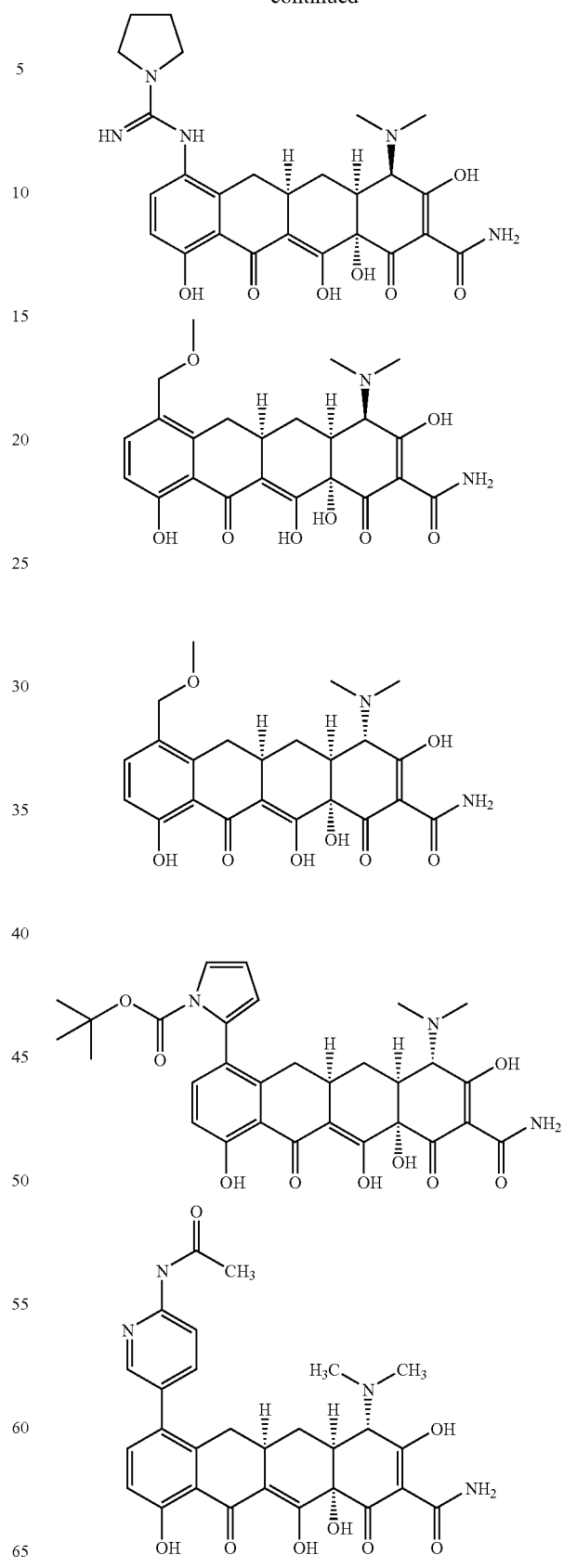

-continued
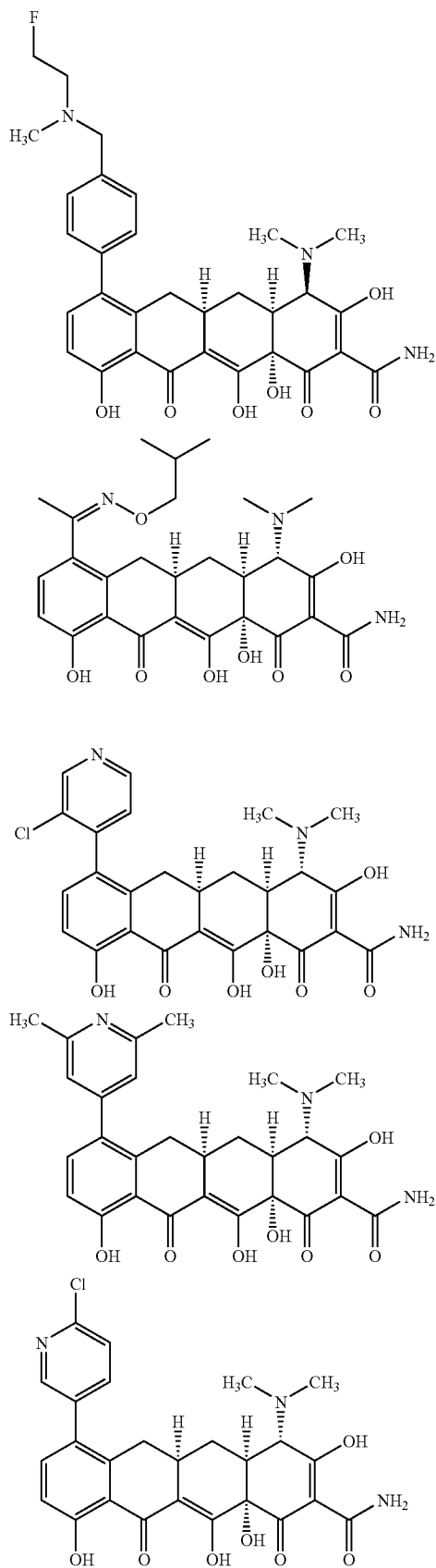
-continued
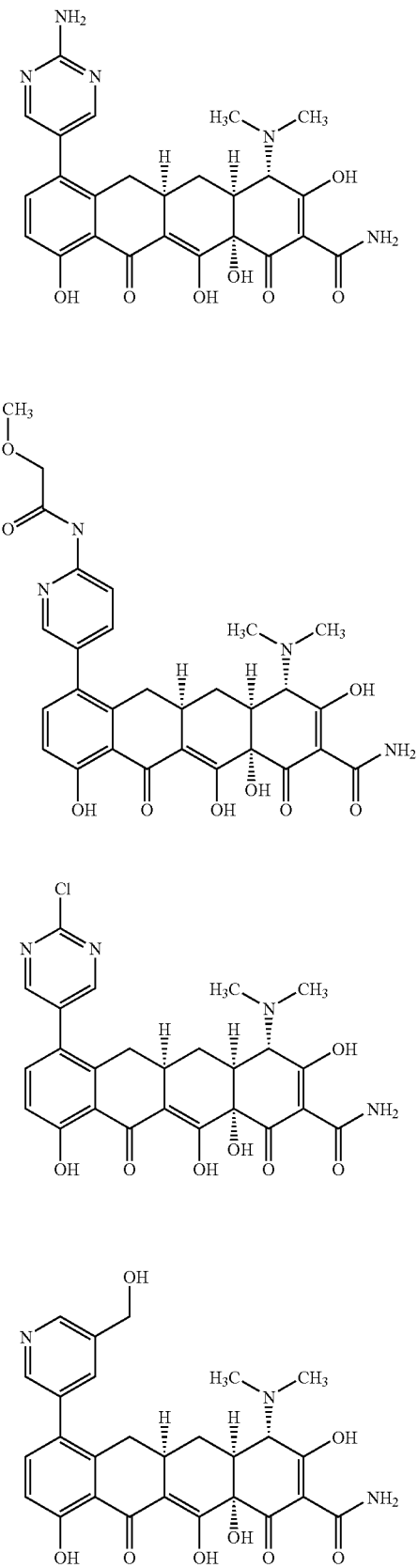

-continued
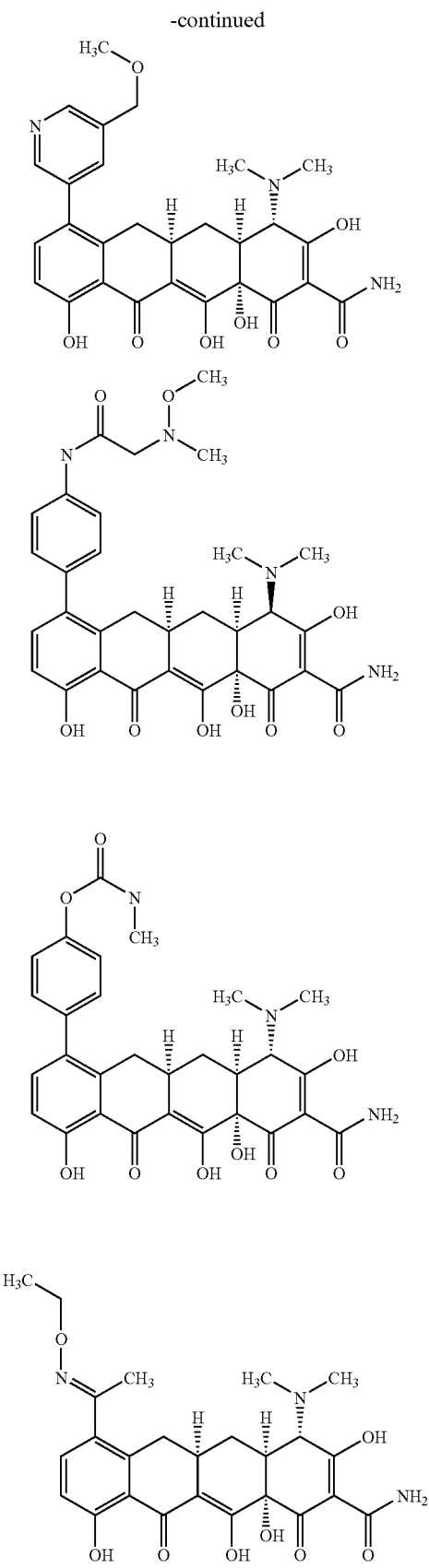
-continued
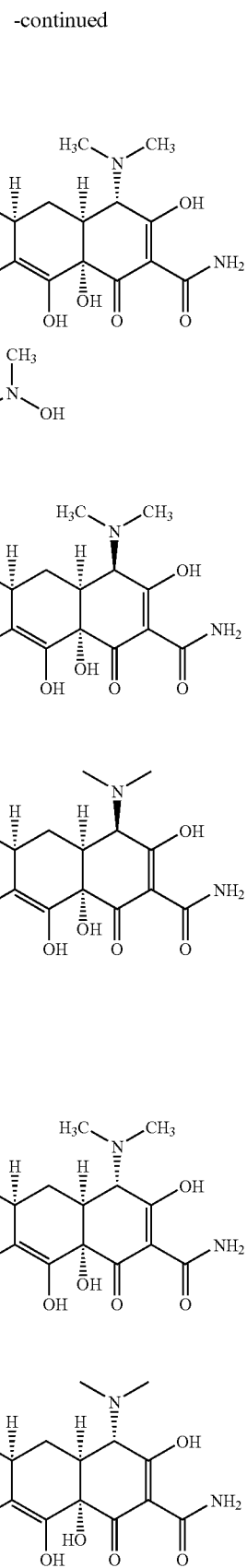

-continued
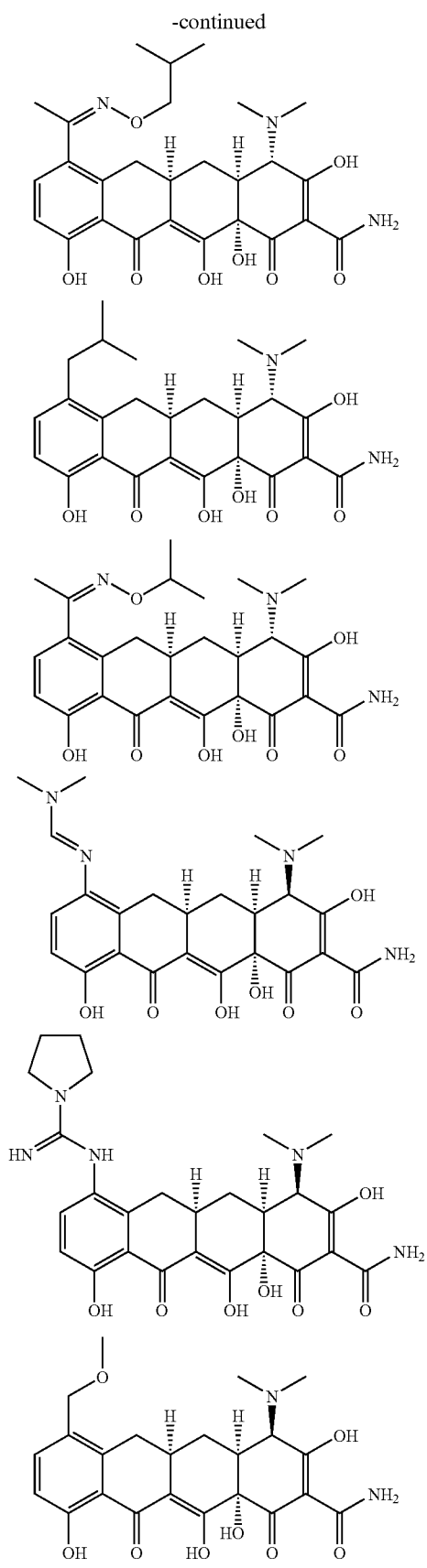
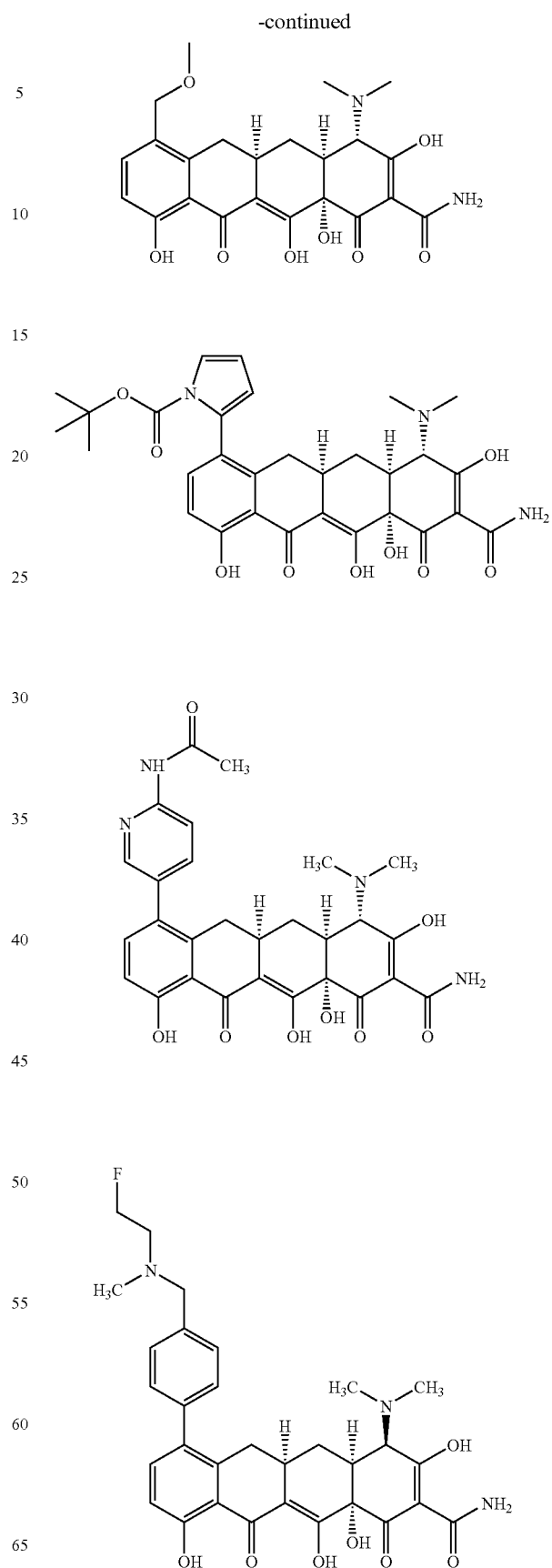

-continued
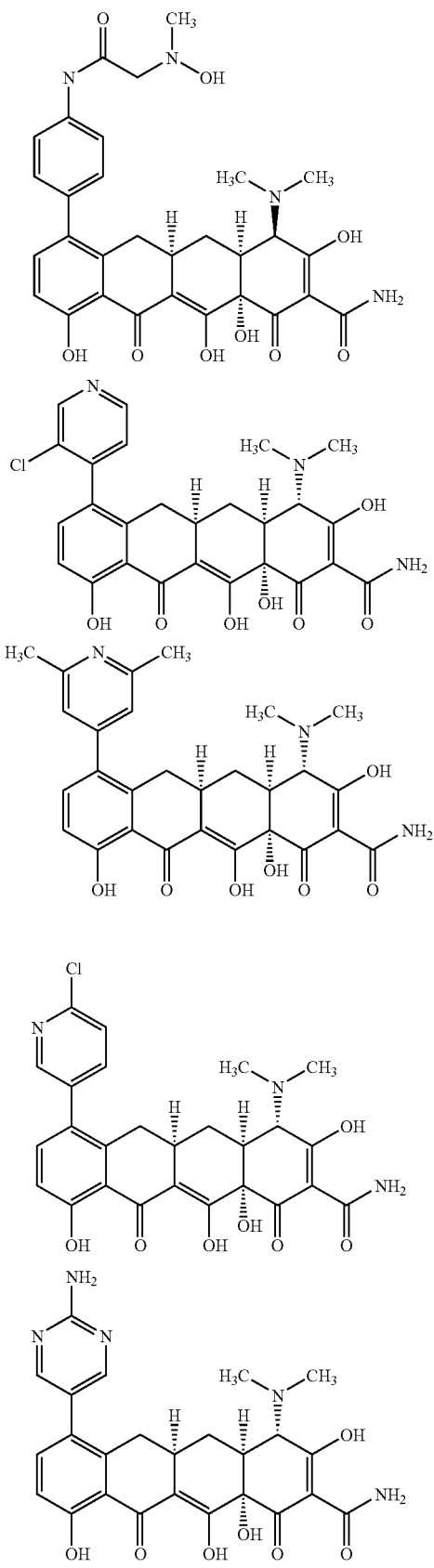
-continued
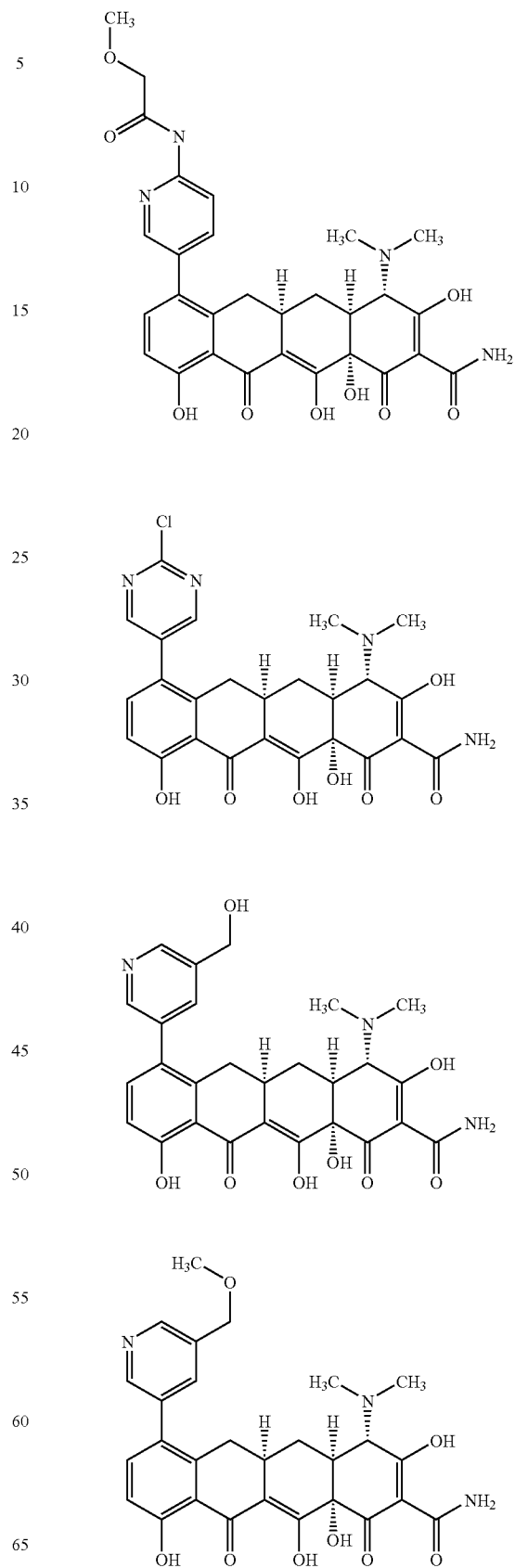

-continued
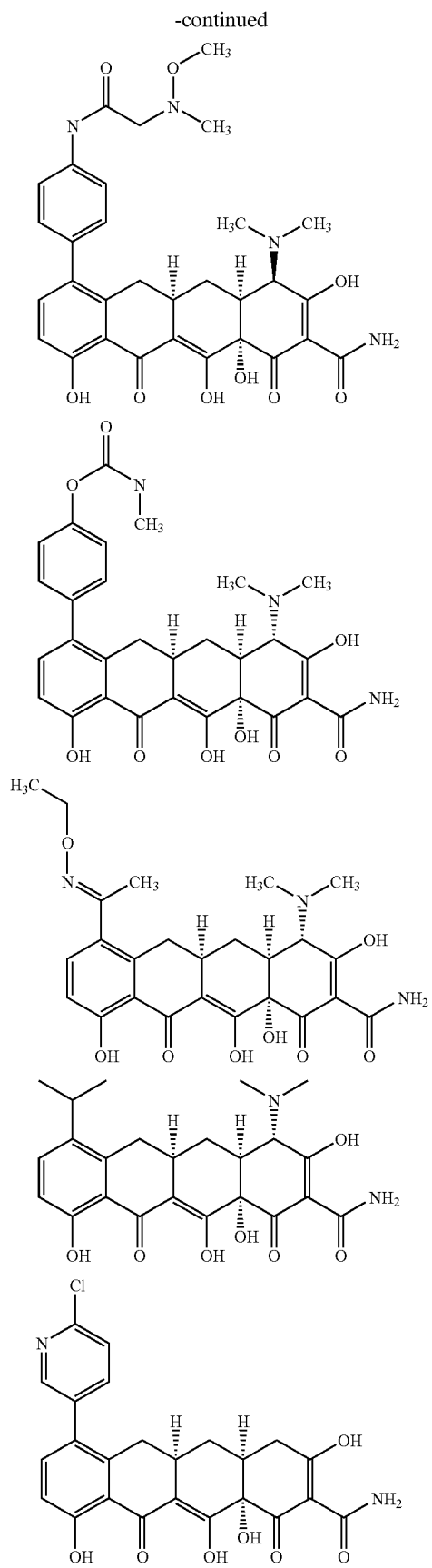
-continued
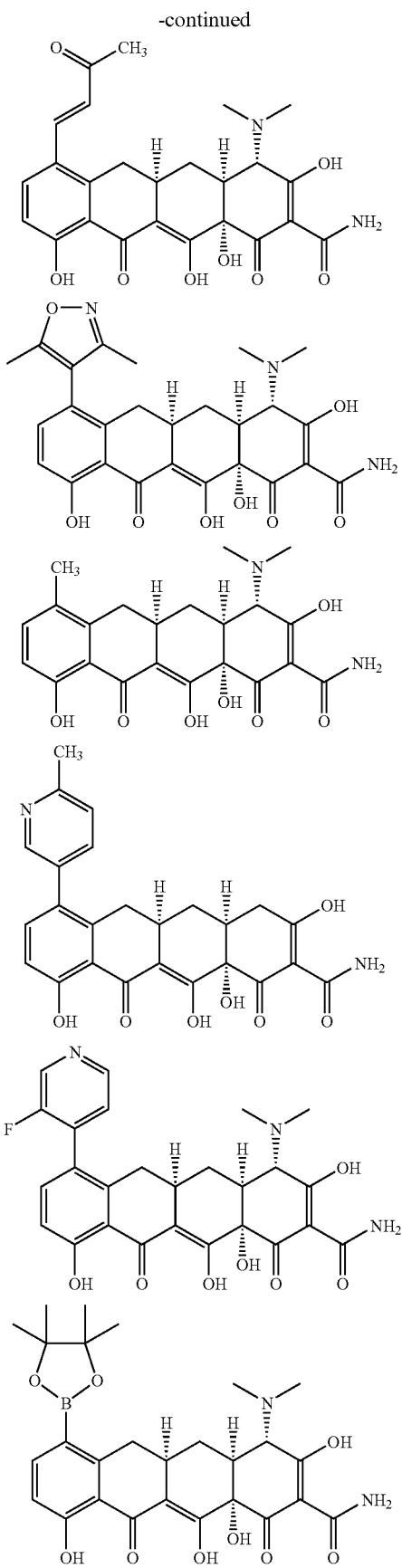

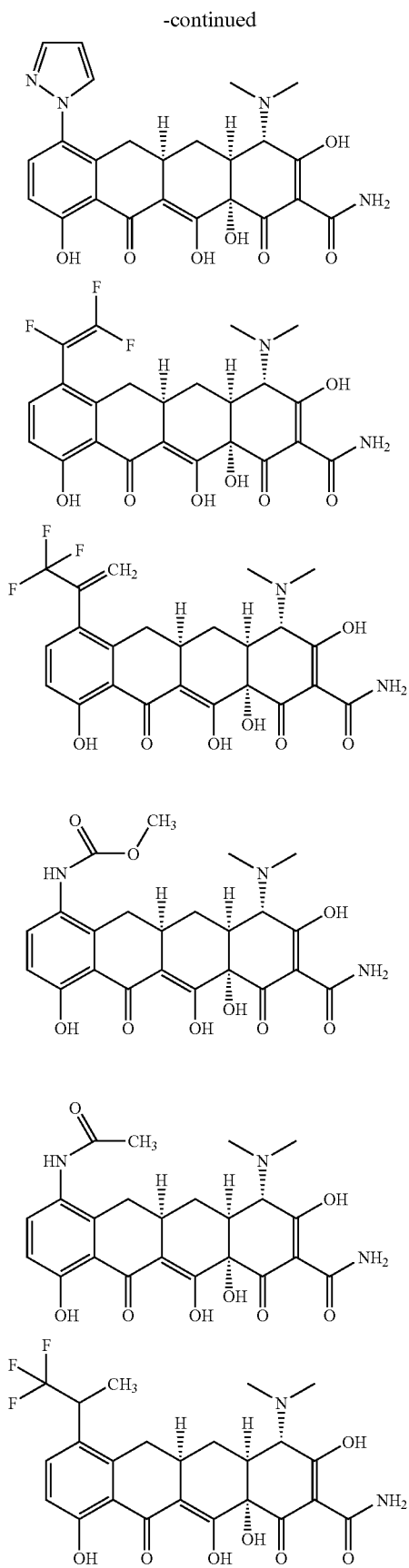

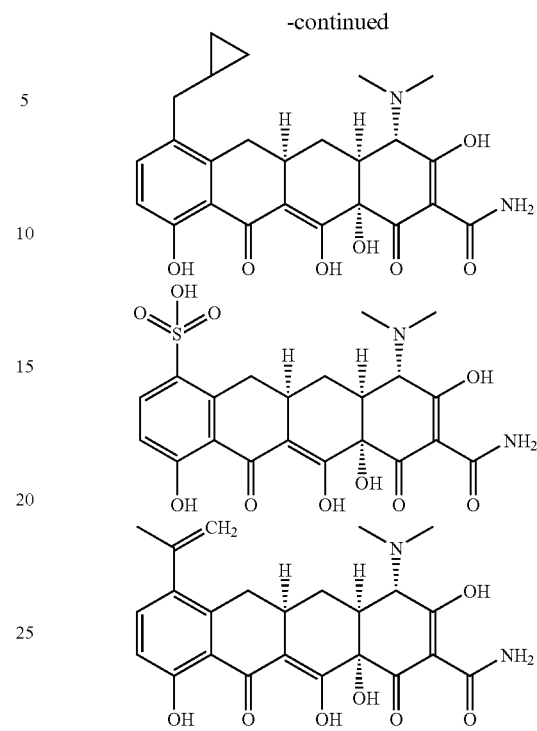

and pharmaceutically acceptable enantiomers, amides, salts, prodrugs, and esters thereof.

2. 7,9-Substituted Tetracycline Compounds

The invention also pertains, at least in part to 7,9-substituted tetracycline compounds.

The term "7,9-substituted tetracycline compounds" includes tetracycline compounds with substitution at the 7 and 9-positions. In one embodiment, the substitution at the 7- and 9-positions enhances the ability of the tetracycline compound to perform its intended function, e.g., treat tetracycline responsive states. In an embodiment, the 7,9-substituted tetracycline compound is 7,9-substituted tetracycline (e.g., wherein $R^4$ is $NR^{4'}R^{4''}$; $R^{4'}$ and $R^{4''}$ are methyl, $R^5$ is hydrogen and X is $CR^6R^{6'}$, wherein $R^6$ is methyl and $R^{6'}$ is hydroxy); 7,9-substituted doxycycline (e.g., wherein $R^4$ is $NR^{4'}R^{4''}$; $R^{4'}$ and $R^{4''}$ are methyl, $R^5$ is hydroxyl and X is $CR^6R^{6'}$, wherein $R^6$ is methyl and $R^{6'}$ is hydrogen); or 7,9-substituted sancycline (wherein $R^4$ is $NR^{4'}R^{4''}$; $R^{4'}$ and $R^{4''}$ are methyl; $R^5$ is hydrogen and X is $CR^6R^{6'}$ wherein $R^6$ and $R^{6'}$ are hydrogen atoms. In an embodiment, the substitution at the 7 position of the 7,9-substituted tetracycline compound is not chlorine or trimethylamino. In one embodiment, $R^4$ is hydrogen.

The 7,9-substituted tetracycline compounds of the invention include compounds of Formula II:

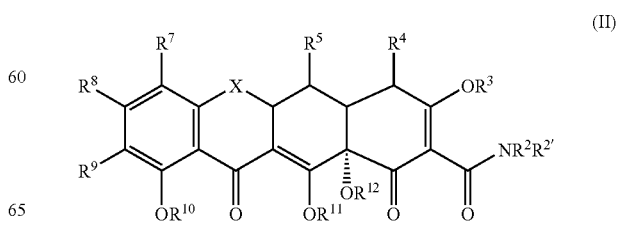

(II)

wherein:

X is $CHC(R^{13}Y'Y)$, $CR^{6'}R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is $-CH_2NR^{7a}R^{7b}$, halogen, $-CH_2OR^{7a}$, substituted alkenylfuranyl, pyrazinyl, pyridinyl, alkyl, acyl, alkyl, alkenyl, alkynyl, aryl, alkoxy, alkylthio, alkylsulfinyl, alkylsulfonyl, arylalkyl, amino, arylalkenyl, arylalkynyl, or $-(CH_2)_{0-3}NR^{7c}C(=W')WR^{7a}$;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is $-CH_2SR^{9a}$, $-CH_2S(=O)R^{9a}$, $-CH_2S(=O)_2R^{9a}$, $-CH_2NR^{9a}R^{9b}$, $SO_3H$, aminoalkyl, furanyl, substituted alkyl, $-(CH_2)_{0-3}(NR^{9c})_{0-1}C(=Z')(Z)_{0-1}R^{9a}$, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}(NR^{9c})_{0-1}C(=Z')(Z)_{0-1}R^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$ S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof, provided that $R^7$ and $R^9$ are not both unsubstituted phenyl.

The tetracycline compounds of the invention include, for example, compounds wherein X is $CR^6R^{6'}$; $R^4$ is $NR^{4'}R^{4''}$; $R^2$, $R^{2'}$, $R^6$, $R^{6'}$, $R^8$, $R^{10}$, $R^{11}$, and $R^{12}$ are each hydrogen; $R^{4'}$ and $R^{4''}$ are lower alkyl; and $R^5$ is hydroxy or hydrogen. In an embodiment, $R^{4'}$ and $R^{4''}$ are each methyl and $R^5$ is hydrogen. The tetracycline compounds of the invention include each possible combination of $R^7$ and $R^9$ substituents discussed below.

In an embodiment, $R^7$ is alkylamino, e.g., $CH_2-NR^{7g}R^{7f}$. In a further embodiment, $R^{7f}$ is hydrogen, alkyl, alkenyl, alkynyl, aryl, heterocyclic, or aralkyl. $R^{7f}$ may be substituted with any substituent which allows the tetracycline compound to perform its intended function. In a further embodiment, $R^{7g}$ is alkyl, alkenyl, alkynyl, aryl, heterocyclic, or hydrogen.

In another embodiment, $R^7$ may be substituted or unsubstituted aryl, e.g., heteroaryl, e.g., furanyl. In another embodiment, $R^7$ may be alkyl, e.g., methyl, ethyl, propyl, etc.

In an embodiment, $R^7$ is aryl (e.g., heteroaryl or substituted or unsubstituted phenyl). The phenyl $R^7$ group may be substituted with one or more substituents. Examples of substituents of phenyl $R^7$ groups include alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, the substituent is substituted or unsubstituted alkyl (e.g., methyl, ethyl, propyl, butyl, etc.), nitro, halogen (e.g., fluorine, bromine, chlorine, iodine, etc.), amino (e.g., unsubstituted amino, alkyl amino, dialkylamino (e.g., dimethylamino), or alkoxy (methylenedioxy or methoxy).

$R^7$ also may be substituted or unsubstituted alkyl (e.g., methyl, ethyl, i-propyl, n-propyl, t-butyl, i-butyl, n-butyl, pentyl, n-pentyl, n-hexyl, or hexyl). The alkyl may be branched or straight chain and may comprise a ring, e.g., a cycloalkyl ring, e.g., cyclohexyl ring.

The alkyl $R^7$ group may be substituted with any substituent which allows the tetracycline compound to perform its intended function. Examples of substituents include, but are not limited to, alkenyl, halogen (e.g., fluorine, chlorine, bromine, iodine, etc.), hydroxyl, alkoxy (e.g., methoxy, ethoxy, perchloromethoxy, perfluoromethoxy, etc.), alkylcarbonyloxy, alkyloxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

Examples of heterocyclic substituents include N-isoindole-[1,3]-dione (e.g., phthalimide). In an embodiment, the substituent is arylcarbonylamino, e.g., heteroaryl carbonyl amino. The heteroaryl group may be, for example, pyridinyl. Other examples of substituents include amino or carboxylate.

In another embodiment, $R^7$ is acyl, e.g., acetyl.

In yet another embodiment, $R^7$ is substituted or unsubstituted alkynyl. Examples of substituents include those which allow the tetracycline compound to perform its intended function. Examples of substituents include, but are not limited to, alkyl (e.g., methyl, ethyl, propyl, butyl, etc.), alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl substituent is substituted or unsubstituted phenyl. The phenyl also may be further substituted with one or more substituents which allow the compound to perform its intended function. Examples of phenyl substituents include, but are not limited to, alkoxy (e.g., methoxy).

Any of the above described $R^7$ groups may be combined with any of the groups described below as $R^9$ groups. In an embodiment, the invention pertains to tetracycline compounds wherein $R^9$ is aminoalkyl. Examples of aminoalkyl $R^9$ groups include groups of the formula: $-CH_2-NR^{9g}R^{9f}$.

Examples of $R^{9f}$ groups include substituted and unsubstituted alkyl, alkenyl, alkynyl, aryl, heterocyclic, aralkyl, and hydrogen. In a further embodiment, $R^{9f}$ may be further substituted with any substituent which allows the tetracycline compound to perform its intended function, for example, treat tetracycline associated states. Examples of $R^{9g}$ groups include substituted and unsubstituted alkyl, alkenyl, alkynyl, aryl, heterocyclic, aralkyl, and hydrogen. In a further embodiment, $R^{9g}$ may be further substituted with any substituent which allows the tetracycline compound to perform its intended function, for example, treat tetracycline associated states.

In a further embodiment, $R^9$ is thioalkyl, e.g., —$CH_2$—S—$R^{9h}$. In a further embodiment, $R^{9h}$ is hydrogen, alkyl, alkenyl, alkynyl, heterocyclic, or aralkyl. In one embodiment, $R^{9h}$ is alkyl.

The tetracycline compounds of the invention include compounds wherein $R^9$ is substituted or unsubstituted aryl (e.g., carbocyclic or heteroaryl). In an embodiment, $R^9$ is substituted or unsubstituted phenyl. The substituted phenyl group can be substituted with any substituent or combination of substituents which allows the compound to perform its intended function. Examples of substituents include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the phenyl $R^9$ substituent is substituted or unsubstituted alkyl, nitro, halogen, amino, or alkoxy (e.g., methylenedioxy).

The invention also includes compounds wherein $R^9$ is substituted or unsubstituted alkyl (e.g., methyl, ethyl, i-propyl, n-propyl, i-butyl, t-butyl, n-butyl, pentyl, hexyl, etc.). The alkyl group may be substituted with any substituent that allows the compound to perform its intended function. Examples of the substituents include, but are not limited to, alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, alkylcarbonylamino, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In an embodiment, wherein said substituent is unsubstituted amino. In a further embodiment, the $R^9$ group is aminomethyl. In another, the alkyl $R^9$ group is substituted with arylcarbonylamino (e.g., heteroarylcarbonylamino, e.g., pyridinylcarbonylamino) or alkylcarbonylamino.

In another further embodiment, the $R^9$ alkyl group is substituted with a heterocyclic substituent, such as isoindole-[1,3]-dione (e.g., phthalimide).

In an embodiment, $R^7$ is acyl, e.g., acetyl.

In yet another embodiment, $R^9$ is substituted or unsubstituted alkynyl. The alkynyl $R^9$ group can be substituted with any substituent which allows the tetracycline compound of the invention to perform its intended function. Examples of substituents include, but are not limited to, alkyl (e.g., methyl, ethyl, propyl, butyl, pentyl, hexyl, heptyl, etc.), alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl substituted alkynyl $R^9$ moiety is, for example, substituted or unsubstituted phenyl. The phenyl may be substituted with, for example, alkoxy, e.g., methoxy. Examples of alkenyl substituents include cycloalkenes such as, cyclohexene.

In one embodiment, $R^9$ is not unsubstituted phenyl when $R^7$ is unsubstituted phenyl.

In one embodiment, $R^7$ is pyridinyl and $R^9$ is alkyl substituted with piperidine or alkylamino. In a further embodiment, $R^9$ is —$CH_2$—S(=O)$_2$-alkyl, —$SO_3H$, iodo, $NO_2$—$CH_2$S-alkyl, —$CH_2$—S(=O)-alkyl, amino, nitro, or —$CH_2O$-alkyl.

In another embodiment, $R^7$ is furanyl, and $R^9$ is substituted or unsubstituted aminoalkyl, or alkyl substituted with substituted or unsubstituted morpholine or piperidine.

In yet another embodiment $R^7$ is —C(=W')W $R^{7a}$, wherein W' is $NR^{7f}$, W is $CR^{7d}R^{7e}$, and $R^{7a}$ is hydrogen and $R^9$ is aminoalkyl. Examples of $R^{7f}$ include alkoxy and examples of $R^9$ include alkylaminoalkyl. Each of these substituents may be further substituted.

In another embodiment, $R^7$ is iodo or chloro. In a further embodiment, $R^9$ is.

In another embodiment, $R^7$ is —$CH_2O$-alkyl and $R^9$ is alkyl.

Examples of 7,9-substituted tetracycline compounds of the invention include those listed below:

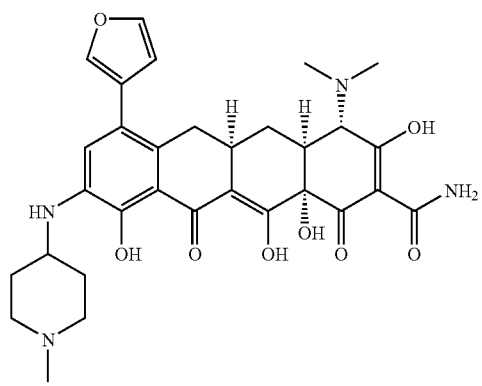

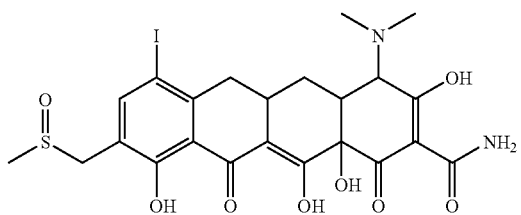

-continued

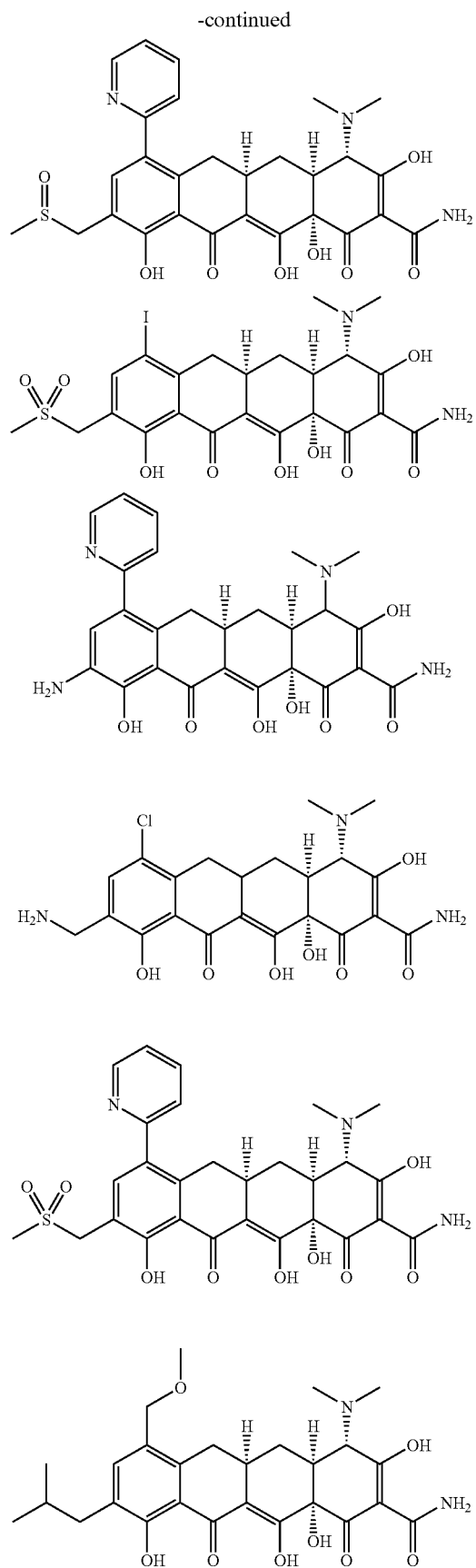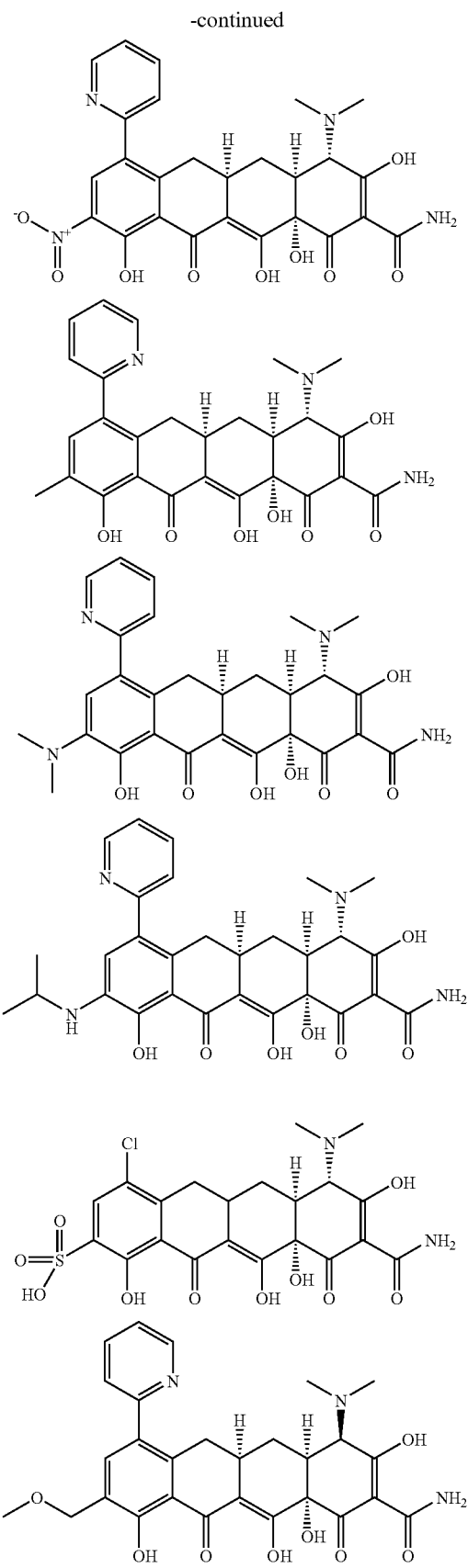

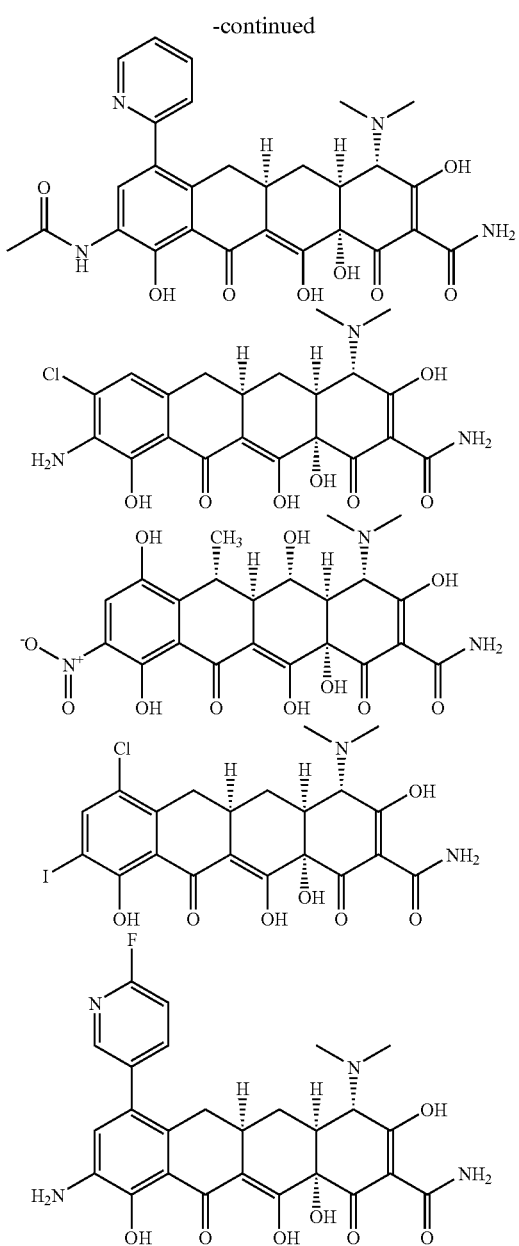

and pharmaceutically acceptable salts, esters, enantiomers, prodrugs, and amides thereof.

3. 9-Substituted Tetracycline Compounds

In another embodiment, the invention pertains to 9-substituted tetracycline compounds.

The term "9-substituted tetracycline compounds" includes tetracycline compounds with substitution at the 9 position. In one embodiment, the substitution at the 9-position enhances the ability of the tetracycline compound to perform its intended function, e.g., treat tetracycline responsive states. In an embodiment, the 9-substituted tetracycline compound is 9-substituted tetracycline (e.g., wherein $R^4$ is $NR^{4'}R^{4''}$, $R^{4'}$ and $R^{4''}$ are methyl; $R^5$ is hydrogen and X is $CR^6R^{6'}$, wherein $R^6$ is methyl and $R^{6'}$ is hydroxy, and $R^7$ is hydrogen); 9-substituted doxycycline (e.g., wherein $R^4$ is $NR^{4'}R^{4''}$, $R^{4'}$ and $R^{4''}$ are methyl, $R^5$ is hydroxyl and X is $CR^6R^{6'}$, wherein $R^6$ is methyl and $R^{6'}$ is hydrogen, and $R^7$ is hydrogen); 9-substituted minocycline (wherein $R^4$ is $NR^{4'}R^{4''}$, $R^{4'}$ and $R^{4''}$ are methyl; $R^5$ is hydrogen and X is $CR^6R^{6'}$ wherein $R^6$ and $R^{6'}$ are hydrogen atoms, and $R^7$ is dimethylamino); 9-substituted 4-dedimethylamino tetracycline compound, wherein X is $CR^6R^{6'}$, $R^4$, $R^5$, $R^{6'}$, $R^6$, and $R^7$ are hydrogen; and 9-substituted sancycline (wherein $R^4$ is $NR^{4'}R^{4''}$, $R^{4'}$ and $R^{4''}$ are methyl; $R^5$ and $R^7$ are hydrogen and X is $CR^6R^{6'}$ wherein $R^6$ and $R^{6'}$ are hydrogen atoms).

The invention also pertains, at least in part, to tetracycline compounds of Formula III:

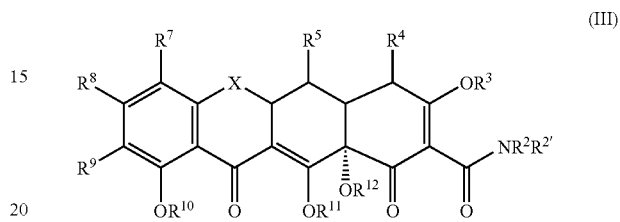

wherein:

X is $CHC(R^{13}Y'Y)$, $CR^{6'}R^6$, S, $NR^6$, or O;

$R^2$, $R^4$, $R^{4''}$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is $NR^{7'}R^{7''}$, alkyl, alkenyl, alkynyl, aryl, hydroxyl, halogen, or hydrogen;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is —$C(=Z')R^{9a}$, $CH_2S(=O)R^{9a}$, —$CH_2OR^{9a}$, alkylthio, alkylsulfinyl, alkylsulfonyl, arylalkyl, heterocyclic, arylalkenyl, arylalkynyl, thionitroso, substituted alkyl, or —$(CH_2)_{0-3}(NR^{9c})_{0-1}C(=Z')(Z)_{0-1}R^{9a}$;

Z is $CR^{9d}R^{9e}$, S, NR or O;

Z' is $NR^{9f}$, O or S;

$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

In an embodiment, the invention features compounds wherein X is $CR^6R^{6'}$; $R^2$, $R^{2'}$, $R^5$, $R^6$, $R^{6'}$, $R^8$, $R^9$, $R^{10}$, $R^{11}$, and $R^{12}$ are each hydrogen; $R^4$ is $NR^{4'}R^{4''}$; $R^7$ is $NR^{7'}R^{7''}$ and $R^{4'}$, $R^{4''}$, $R^{7'}$, and $R^{7''}$ are each lower alkyl, e.g., methyl. In certain other embodiments, $R^7$ may be hydrogen.

In one embodiment, $R^9$ is alkyl amino. For example, $R^9$ may be —$CH_2$—$NR^{9f}R^{9g}$. Examples of $R^{9f}$ include but are not limited to hydrogen, alkyl, alkenyl, alkynyl, aryl, aralkyl, etc. $R^{9f}$ may be substituted with any substituent which allows the minocycline compound of the invention to perform its intended function, e.g., treat tetracycline associated states or other functions. In a further embodiment, $R^{9f}$ is hydrogen or alkyl.

In other embodiments, $R^{9f}$ and $R^{9g}$ are linked by a chain of from 0 to 5 atoms. The atoms may be carbon, oxygen, nitrogen, sulfur, etc. In certain embodiments, the ring that is formed has 3, 4, 5, 6, or 7 members. In other embodiments, the ring that is formed is morpholinyl, piperidinyl, or pyrazinyl. The ring may be substituted or unsubstituted.

In certain embodiments, $R^{9g}$ is heterocyclic (e.g., piperidinyl, piperazinyl, morpholinyl, pyrazolyl, pyridinyl, etc.) In other embodiments, $R^{9g}$ is aralkyl. $R^{9g}$ may comprises a substituted or unsubstituted heteroaryl group, or may comprise a substituted or unsubstituted phenyl group. In other embodiments, $R^{9g}$ is substituted or unsubstituted heteroaryl or phenyl.

In other embodiments, $R^9$ is substituted amino. In certain embodiments, $R^9$ is amino substituted with a heterocyclic group, such as, but not limited to, morpholinyl, piperazinyl, or piperidinyl. In other embodiments, $R^9$ is substituted or unsubstituted aralkylamino, e.g., substituted or unsubstituted benzylamino.

In yet other embodiments, $R^9$ may also be furanyl. In further embodiments, furanyl $R^9$ groups may be substituted with one or more substituents, such as, but not limited to, heterocyclic groups and other moieties which allow the minocycline compound of the invention to perform its intended function.

Other examples of $R^9$ include substituted and unsubstituted aryl groups. The aryl groups include substituted and unsubstituted heteroaryls (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, or deazapurinyl), substituted or unsubstituted phenyl, and groups with more than one aromatic ring, such as naphthyl.

Examples of substituents of $R^9$ include, but are not limited to, alkyl, alkenyl, halogen, hydroxyl, alkoxy, alkylcarbonyloxy, alkyloxycarbonyl, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aralkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl $R^9$ group is substituted with one or more substituents such as, for example, carboxylate, alkyl, alkenyl, alkynyl, aryl, heterocyclic, cyano, amino, halogen, alkoxy, alkoxycarbonyl, amido, alkylcarbonyl, or nitro.

In another embodiment, $R^9$ is substituted or unsubstituted alkynyl. The alkynyl $R^9$ group may be substituted with a substituted or unsubstituted aryl group, such as, for example, phenyl. The possible substituents for the substituted phenyl group include, for example, those listed supra, for the aryl $R^9$ group. Furthermore, the substituted alkynyl $R^9$ group may be substituted with a heteroaryl (e.g., pyridinyl), alkyl (e.g., methyl, ethyl, propyl, butyl, pentyl, hexyl, cyclopropyl, cyclobutyl, cyclopentyl, cyclohexyl, etc.), alkenyl (e.g., ethenyl, propenyl, butenyl, pentenyl, hexenyl, etc.), carboxylate, silyl (e.g., trialkylsilyl, e.g., trimethylsilyl), aralkyl, or a alkyloxycarbonyl group.

Each of these groups may also be further substituted, with such substituents as alkyl, alkenyl, halogen, hydroxyl, alkoxy, alkylcarbonyloxy, alkyloxycarbonyl, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the alkynyl $R^9$ group is substituted with an aminoalkyl group. The aminoalkyl group may then also be substituted with, for example, an alkyl, alkenyl, alkynyl, acyl, carbonyl, or alkylsulfone group.

In another further embodiment, the alkynyl $R^9$ group is substituted with a cycloalkenyl group, such as, for example, cyclopentene.

In another embodiment, $R^9$ is alkyl. The alkyl group may be substituted or unsubstituted. Examples of alkyl groups include, for example, both straight chain, branched and cyclic alkyl groups. For example, alkyl groups include methyl, ethyl, i-propyl, n-propyl, i-butyl, n-butyl, t-butyl, pentyl, hexyl, heptyl, octyl, nonyl, decyl, etc. Cyclic alkyl groups include groups with one or more rings, such as, for example, cyclopropane, cyclobutane, cyclopentane, cyclohexane, cycloheptane, etc. In an embodiment, the alkyl $R^9$ group is 2-cyclopentylethyl.

Examples of substituents of alkyl groups include, for example, halogens (e.g., fluorine, chlorine, bromine, iodine, etc.), hydroxyl, alkoxy (e.g., methoxy, ethoxy, propoxy, butoxy, pentoxy, perfluoromethoxy, perchloromethoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, carboxy, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amido, imino, sulfhydryl, alkylthio, arylthio, thiocarboxylate, sulfate, alkylsulfinyl, alkenyl, sulfonato, sulfamoyl, sulfonamido, nitro, alkenyl, cyano, azido, heterocyclyl, alkylaryl, aryl and heteroaryl.

In another embodiment, the minocycline compound of the invention is a compound wherein $R^9$ is —$NR^{9c}C(=Z')ZR^{9a}$, —$CH_2NR^{9c}C(=Z')ZR^{9a}$, —$(CH_2)_2NR^{9c}C(=Z')ZR^{9a}$, or —$(CH_2)_3NR^{9c}C(=Z')ZR^{9a}$. In certain embodiments, $R^9$ is —$NR^{9c}C(=Z')ZR^{9a}$ or —$CH_2NR^{9c}C(=Z')ZR^{9a}$. Examples of $R^{9c}$ include hydrogen. Z' may be, for example, S, NH, or O. Examples of Z include $NR^{9b}$ (e.g., when $R^{9b}$ is hydrogen, alkyl, etc.), O or S.

Examples of $R^{9a}$ groups include aryl groups such as substituted and unsubstituted phenyl. Examples of possible substituents of aryl $R^{9a}$ groups include, but are not limited to, alkyl (e.g., methyl, ethyl, propyl, butyl, pentyl, hexyl, perfluoromethyl, perchloroethyl, etc.), alkenyl, halogen (e.g., fluorine, chlorine, bromine, iodine, etc.), hydroxyl, alkoxy (e.g., methoxy, ethoxy, propoxy, perfluoromethoxy, perchloromethoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amido, imino, sulfhydryl, alkylthio, arylthio, thiocarboxylate, sulfate, alkylsulfinyl, sulfonato, sulfamoyl, sulfonamido, nitro, acetyl, alkyl, cyano, azido, heterocyclyl, alkylaryl, aryl and heteroaryl groups.

In certain embodiments, at least one of the substituents of the substituted phenyl is nitro, alkoxy (e.g., methoxy, methylenedioxy, perfluoromethoxy) alkyl (e.g., methyl, ethyl, propyl, butyl, or pentyl), acetyl, halogen (e.g., fluorine, chlorine, bromine, or iodine), or amino (e.g., dialkylamino). In certain embodiments, the alkoxy group is perhalogenated, e.g., perfluoromethoxy.

Examples of aryl $R^{9a}$ groups include, but are not limited to, unsubstituted phenyl, para-nitrophenyl, para-methoxy phenyl, para-perfluoromethoxy phenyl, para-acetyl phenyl, 3,5-methylenedioxyphenyl, 3,5-diperfluoromethyl phenyl, para-bromo phenyl, para-chloro phenyl, and para-fluoro phenyl.

Other examples of aryl $R^{9a}$ groups include substituted and unsubstituted heterocycles (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, pyrolidinyl, oxazolyl, isooxazolyl, naphthridinyl, thiazolyl, isothiazolyl, or deazapurinyl) and substituted and unsubstituted biaryl groups, such as naphthyl and fluorene.

$R^{9a}$ also may be substituted or unsubstituted alkyl, e.g., methyl, ethyl, propyl, butyl, pentyl, etc. Examples of substituents include but are not limited to halogens (e.g., fluorine, bromine, chlorine, iodine, etc.), hydroxyl, alkoxy (e.g., methoxy, ethoxy, propoxy, butoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfate, alkylsulfinyl, sulfonato, sulfamoyl, sulfonamido, nitro, trifluoromethyl, cyano, azido, alkenyl, heterocyclyl, alkylaryl, aryl and heteroaryl.

$R^{9a}$ also can be substituted or unsubstituted alkenyl. Examples of substituents for alkenyl $R^{9a}$ groups include those listed above for alkyl $R^{9a}$ groups. Examples of alkenyl $R^{9a}$ groups include pent-1-enyl.

In an embodiment, Z' is NH, Z is NH, and $R^{9a}$ is alkyl.

In another embodiment, $R^9$ is alkyl and substituted with a heterocycle, such as 2,3-dihydro-isoindole.

In another embodiment, $R^9$ is —C(=Z')$R^{9a}$, Z' is $NR^{9f}$ and $R^{9a}$ is hydrogen. $R^{9f}$ may be alkoxy.

In a further embodiment, $R^9$ is substituted aminoalkyl. $R^9$ may be substituted, for example, with a substituted or unsubstituted alkyloxycarbonyl group, a substituted or unsubstituted alkyl group and/or a substituted or unsubstituted aralkyl group.

In another embodiment, the invention pertains to tetracycline compounds of the formulae:

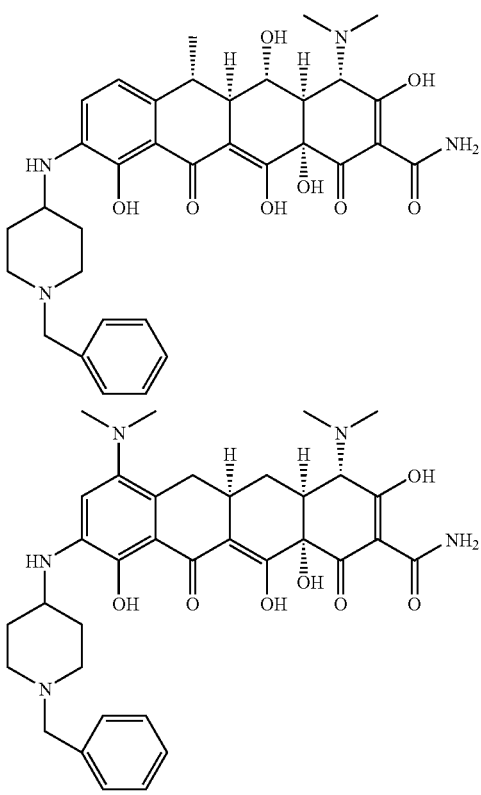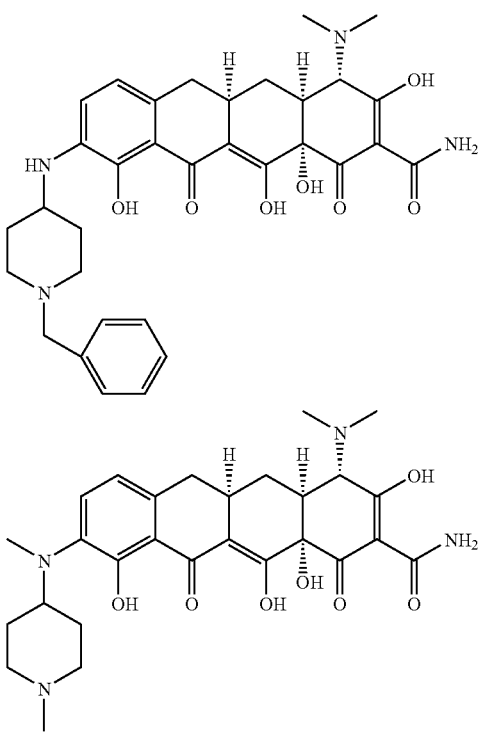

67 68
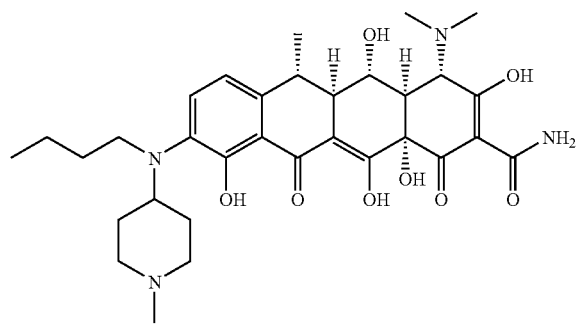
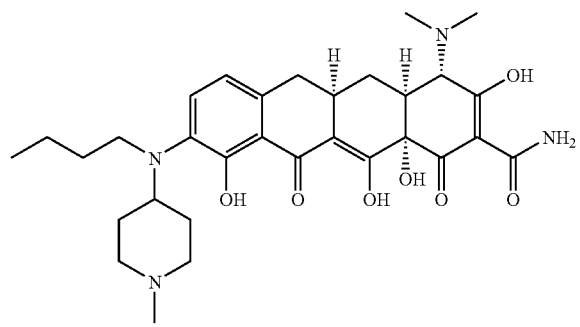
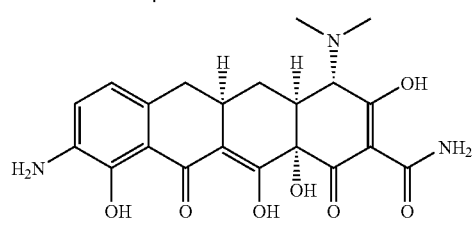
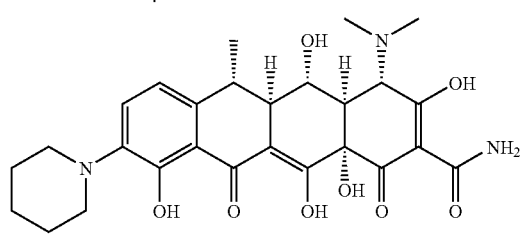
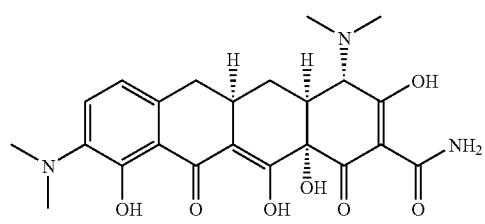
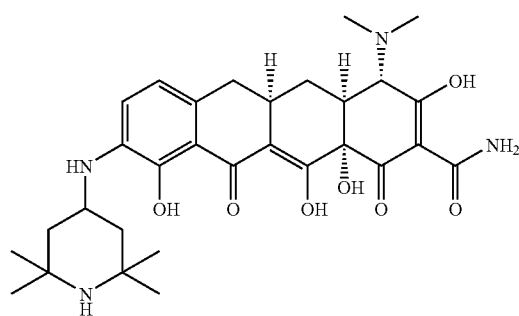
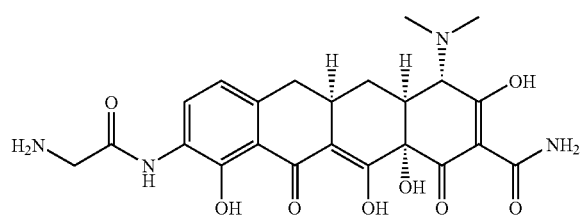
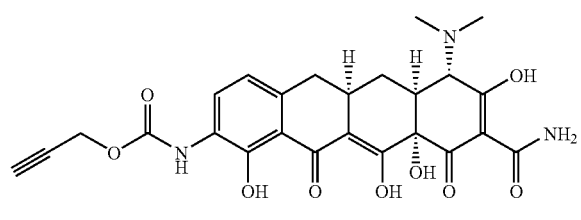
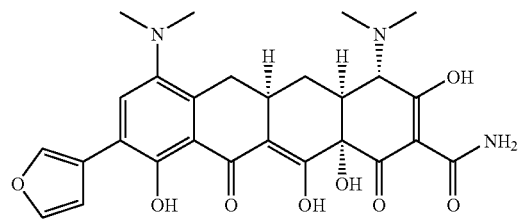
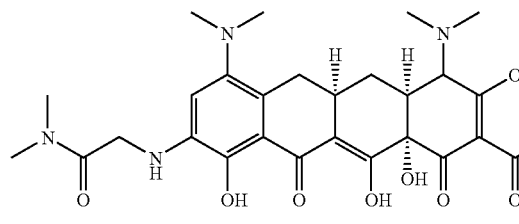
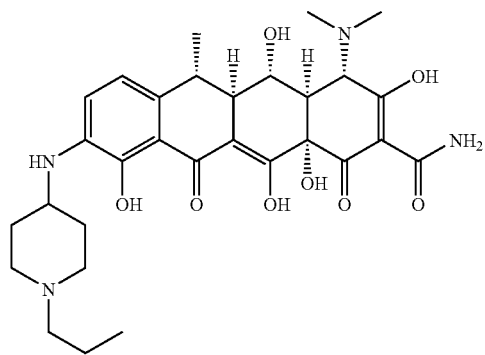
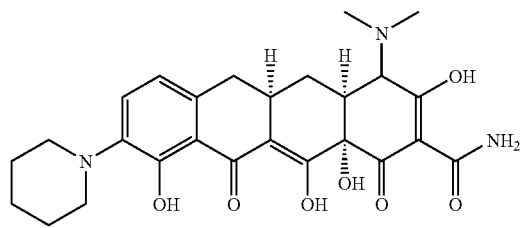

-continued
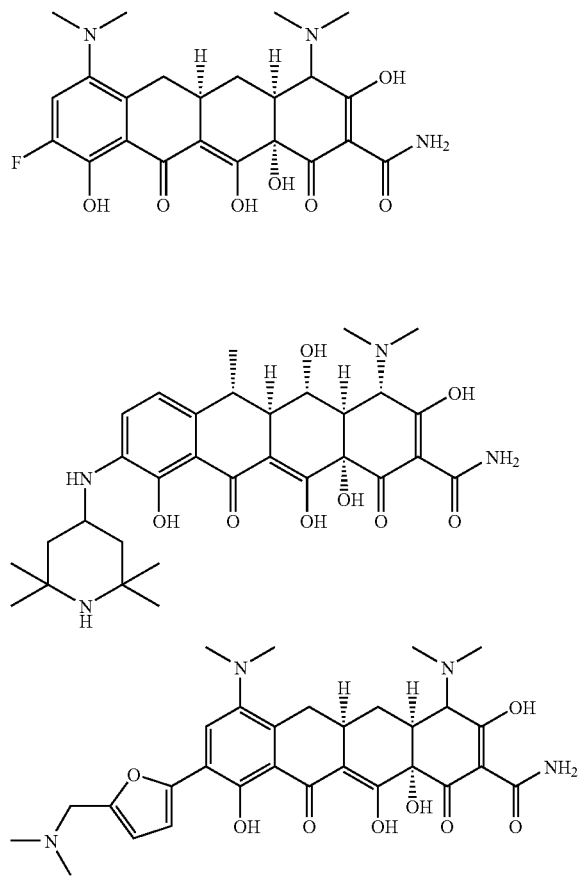
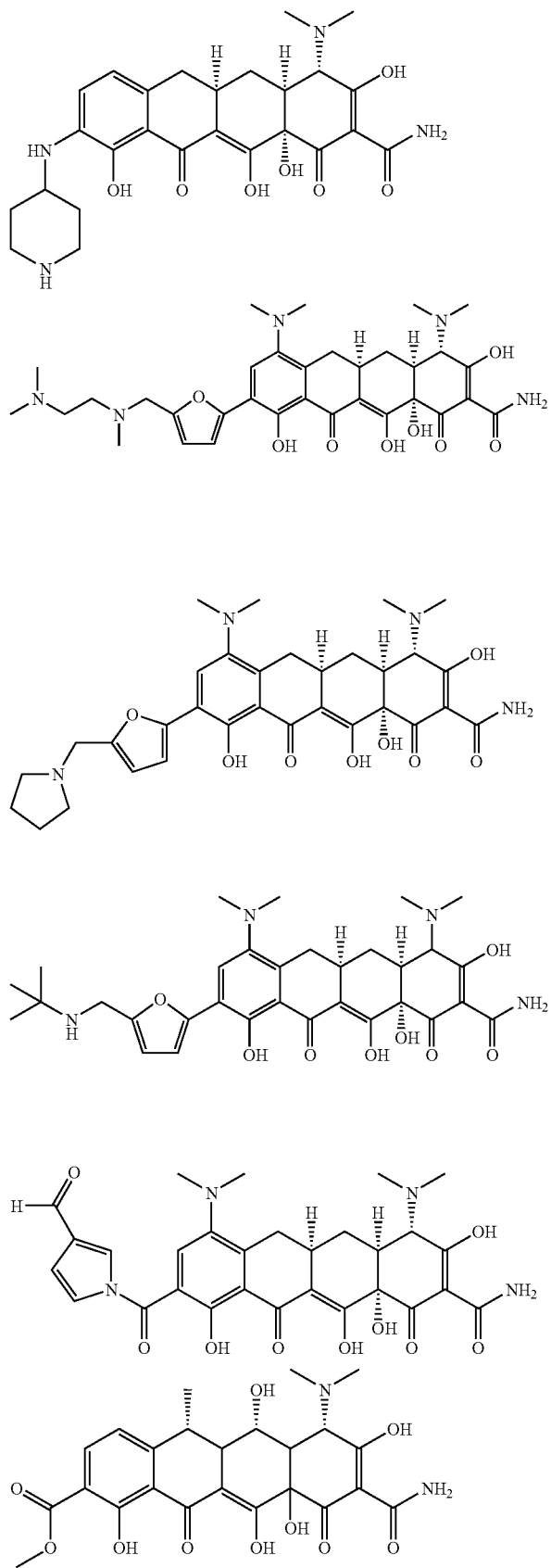

71 72
-continued
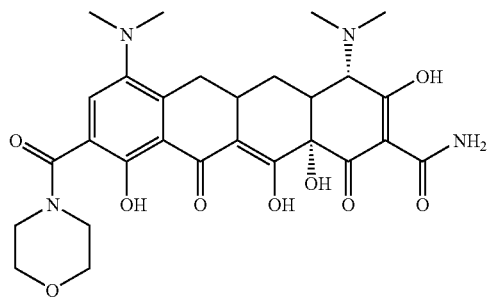
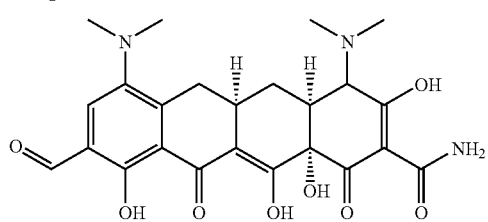
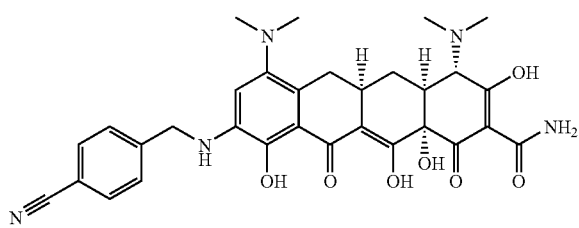
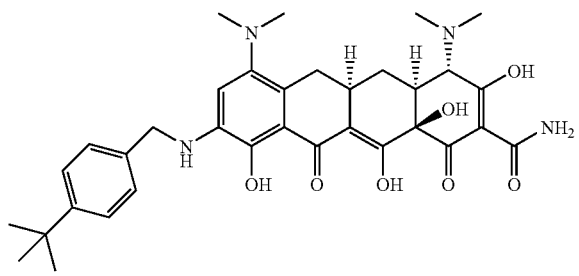
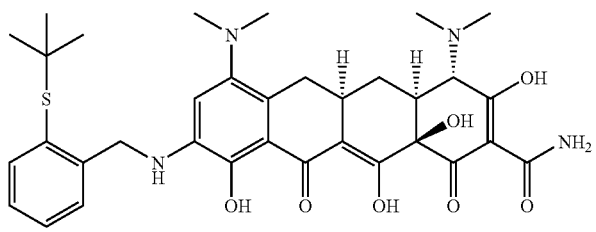
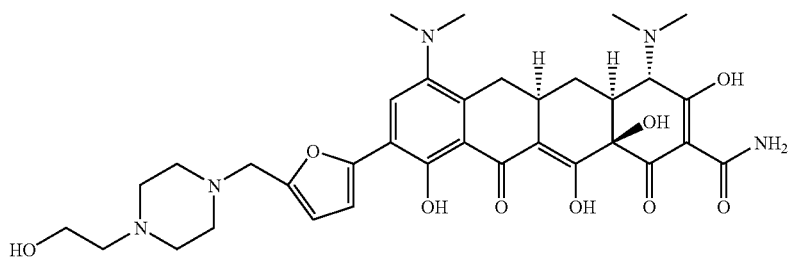

73 74
-continued
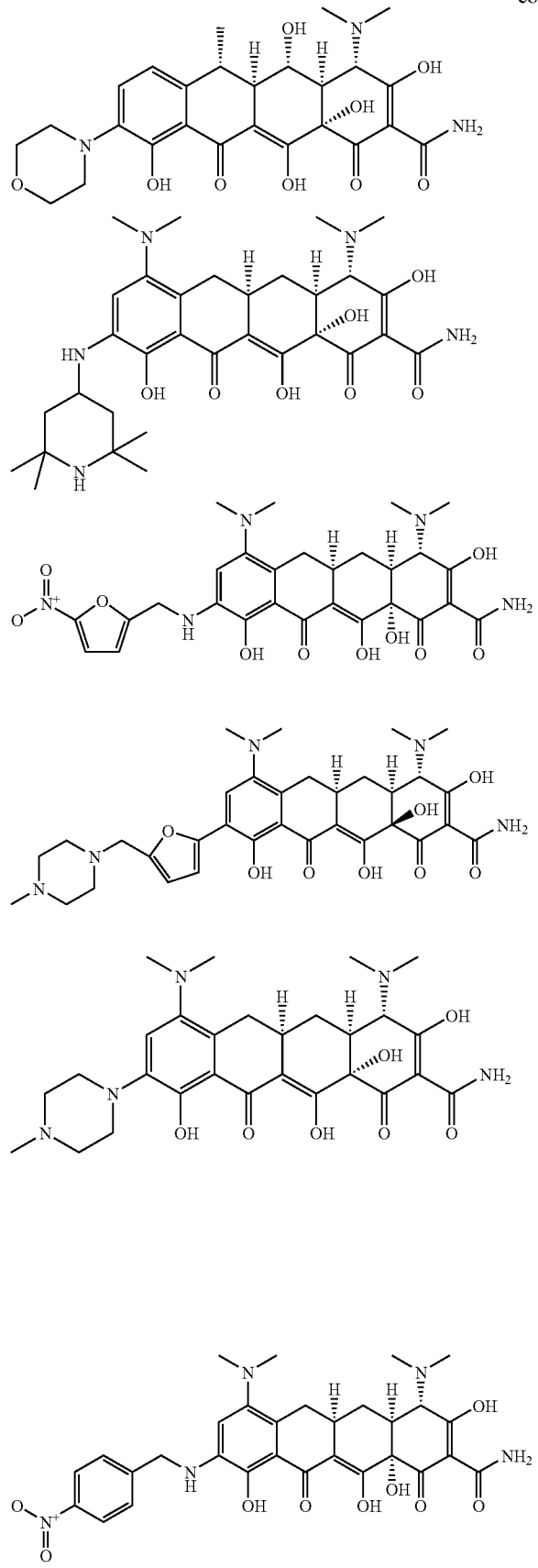
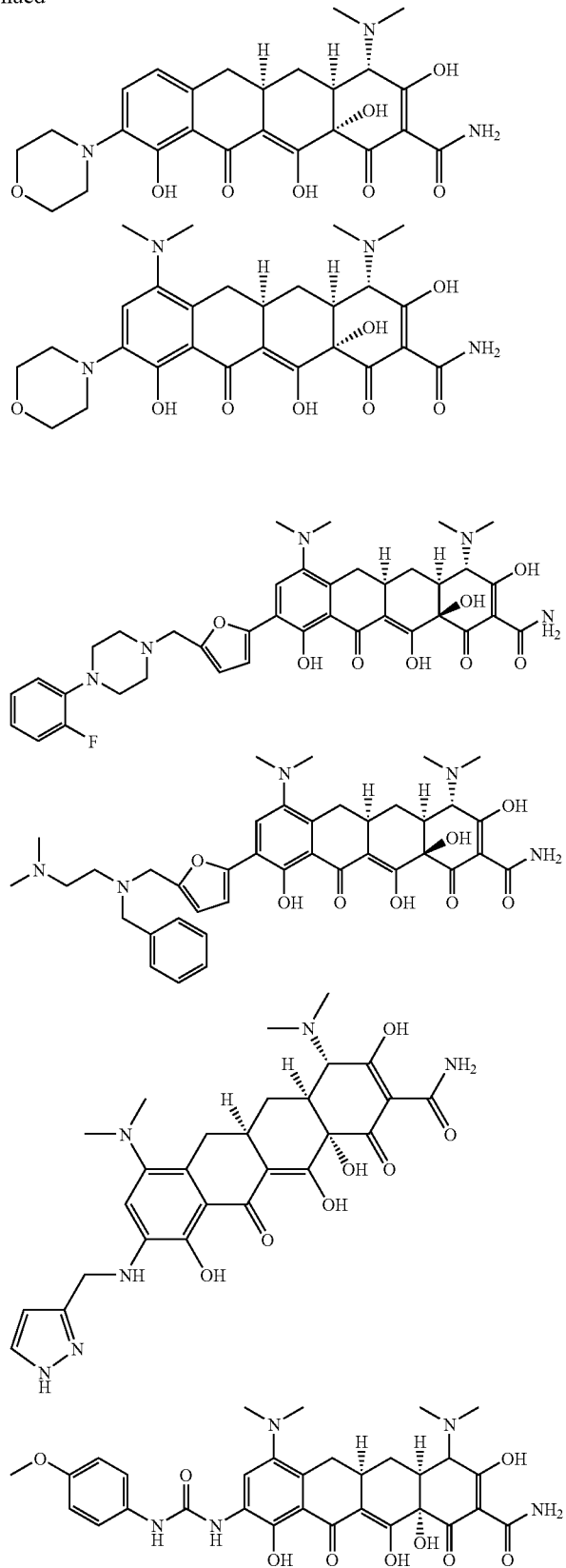

-continued
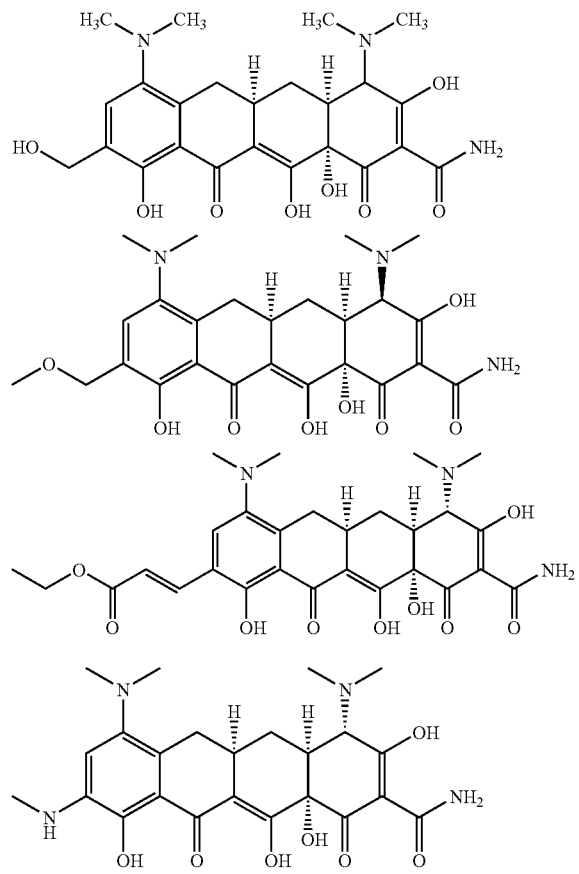
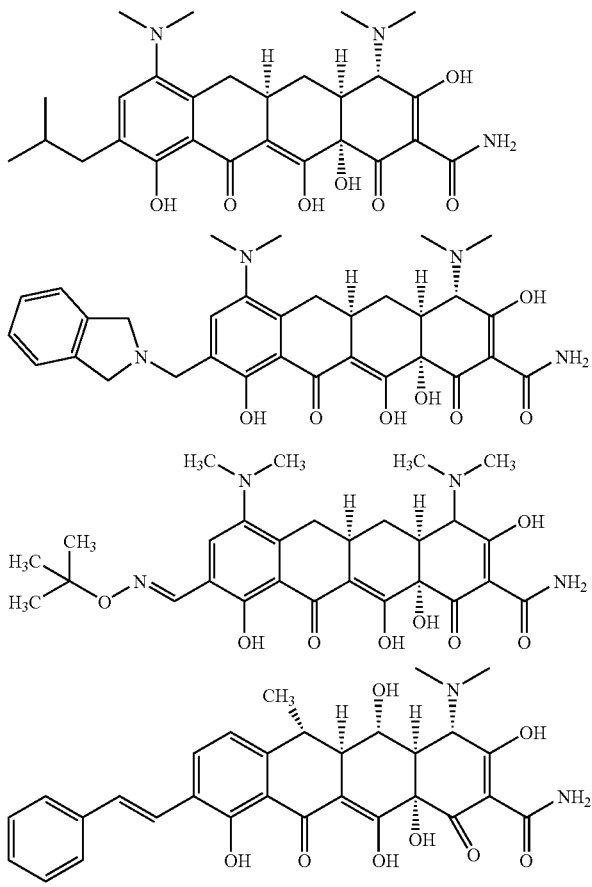
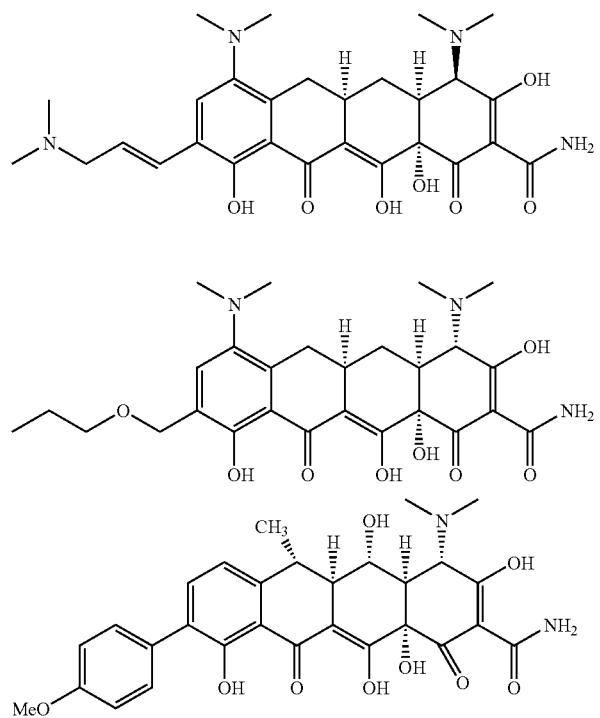
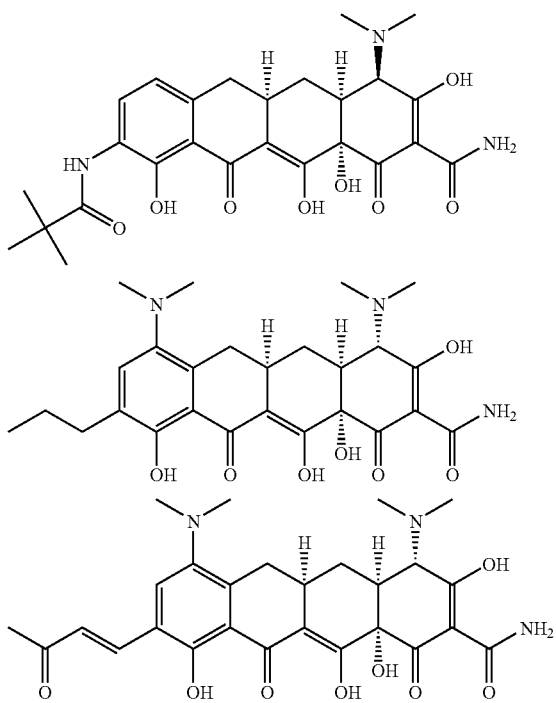

-continued

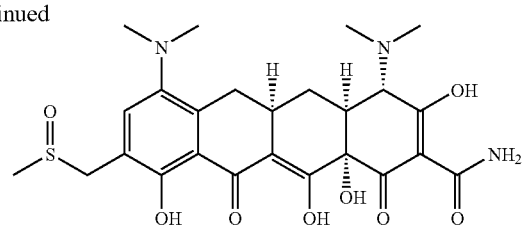
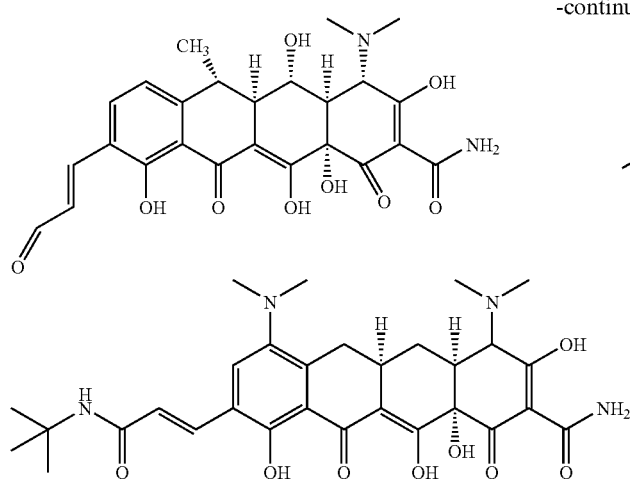
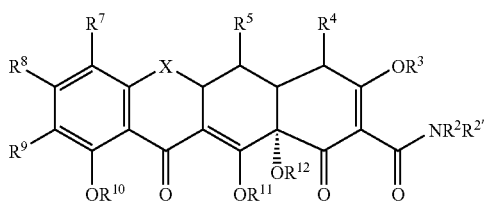

or pharmaceutically acceptable salts, amides, enantiomers, prodrugs, or esters thereof.

4. 8-Substituted Tetracycline Compounds

The invention also pertains, at least in part to 8-substituted tetracycline compounds.

The term "8-substituted tetracycline compounds" includes tetracycline compounds with substitution at the 8-position. In one embodiment, the substitution at the 8-position enhances the ability of the tetracycline compound to perform its intended function, e.g., treat tetracycline responsive states. In an embodiment, the 8-substituted tetracycline compound is 8-substituted tetracycline (e.g., wherein $R^4$ is $NR^{4'}R^{4''}$; $R^{4'}$ and $R^{4''}$ are methyl, $R^5$ is hydrogen and X is $CR^6R^{6'}$, wherein $R^6$ is methyl and $R^{6'}$ is hydroxy); 8-substituted doxycycline (e.g., wherein $R^4$ is $NR^{4'}R^{4''}$; $R^{4'}$ and $R^{4''}$ are methyl, $R^5$ is hydroxyl and X is $CR^6R^{6'}$, wherein $R^6$ is methyl and $R^{6'}$ is hydrogen); or 8-substituted sancycline (wherein $R^4$ is $NR^{4'}R^{4''}$; $R^{4'}$ and $R^{4''}$ are methyl; $R^5$ is hydrogen and X is $CR^6R^{6'}$ wherein $R^6$ and $R^{6'}$ are hydrogen atoms. In an embodiment, the substitution at the 7 position of the 8-substituted tetracycline compound is not chlorine or trimethylamino. In one embodiment, $R^4$ is hydrogen.

In one embodiment, the 8-substituted tetracycline compound is of formula IV:

(IV)

wherein:

X is $CHC(R^{13}Y'Y)$, $CR^6R^{6'}$, S, $NR^6$, or O;

$R^2$, $R^{4'}$, $R^{4''}$, $R^7$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7c})_{0-1}C(=W')WR^{7a}$;

$R^8$ is hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9e}$, and $R^{8f}$ are each independently absent, hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

E is $CR^{8d}R^{8e}$, S, $NR^{8b}$ or O;

E' is O, $NR^{8f}$, or S;

W is $CR^{7d}R^{7e}$, S, O or $NR^{7b}$;

W' is O, $NR^{7f}$, or S;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

In a further embodiment, the invention pertains to compounds wherein X is $CR^6R^{6'}$; $R^2$, $R^{2'}$, $R^6$, $R^{6'}$, $R^8$, $R^{10}$, $R^{11}$, and $R^{12}$ are each hydrogen; $R^4$ is $NR^{4'}ER^{4''}$; $R^{4'}$ and $R^{4''}$ are lower alkyl; and $R^5$ is hydroxy or hydrogen.

In another embodiment, $R^8$ is halogen, e.g., chloro or bromo.

In another embodiment, $R^8$ is unsubstituted or substituted aryl. Examples of heteroaryl group include furanyl. Examples of aryl groups include phenyl.

In a further embodiment, $R^9$ or $R^7$ is a substituted or unsubstituted amino. The amino group may be substituted, for example, with carbonyl, alkyl, or any other substituent described herein.

Examples of 8-substituted tetracycline compounds include:

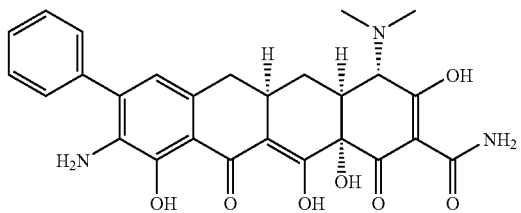

5. Methods for Synthesizing Tetracycline Compounds of the Invention

The tetracycline compounds of this invention can be synthesized using the methods described in the Schemes and/or by other techniques known to those of ordinary skill in the art.

The substituted tetracycline compounds of the invention can be synthesized using the methods described in Example 1, in the following schemes and by using art recognized techniques. All novel substituted tetracycline compounds described herein are included in the invention as compounds.

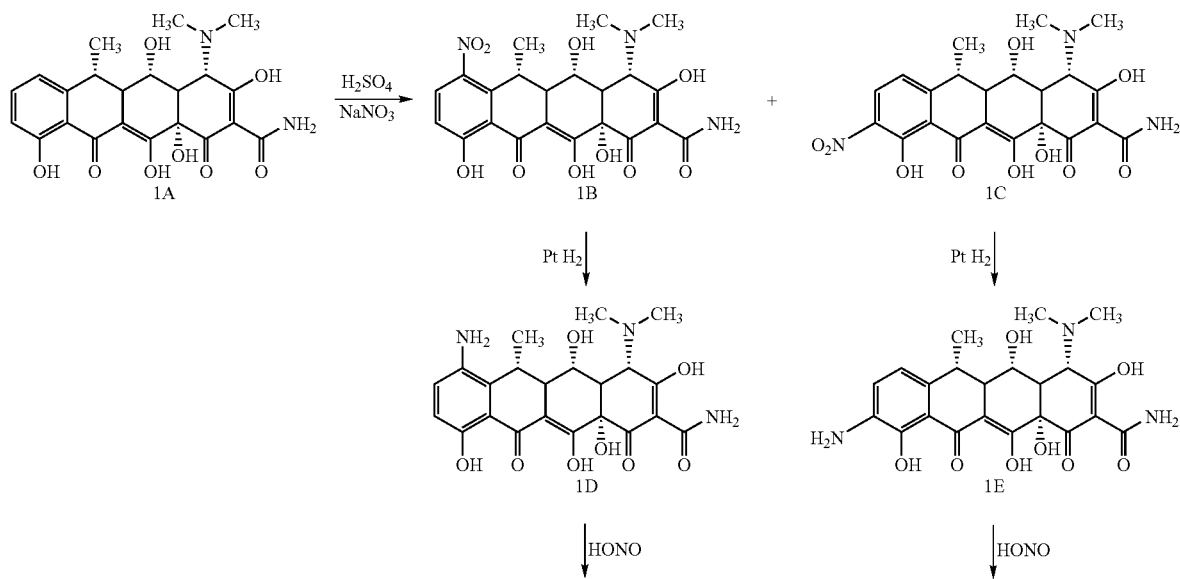

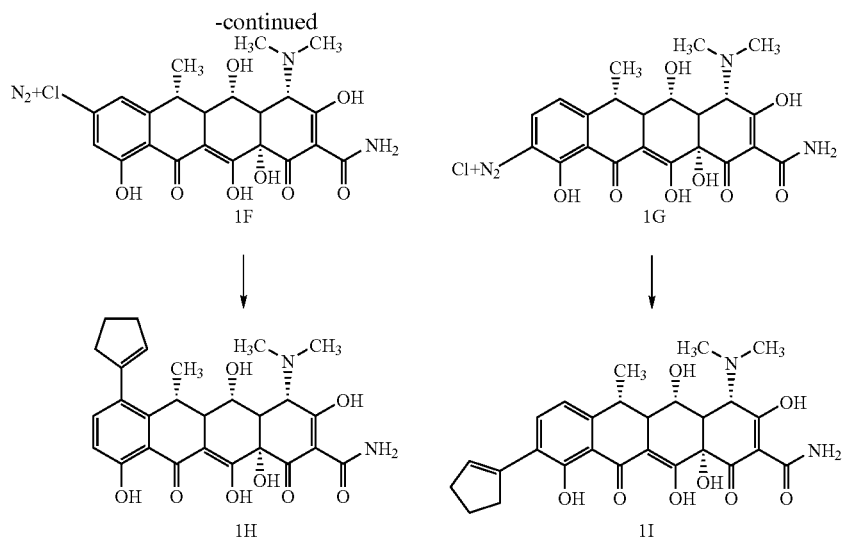

9- and 7-substituted tetracyclines can be synthesized by the method shown in Scheme 1. As shown in Scheme 1, 9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate reactive reagent to yield the desired compound (e.g., in Scheme 1, 7-cyclopent-1-enyl doxycycline (1H) and 9-cyclopent-1-enyl doxycycline (1I)).

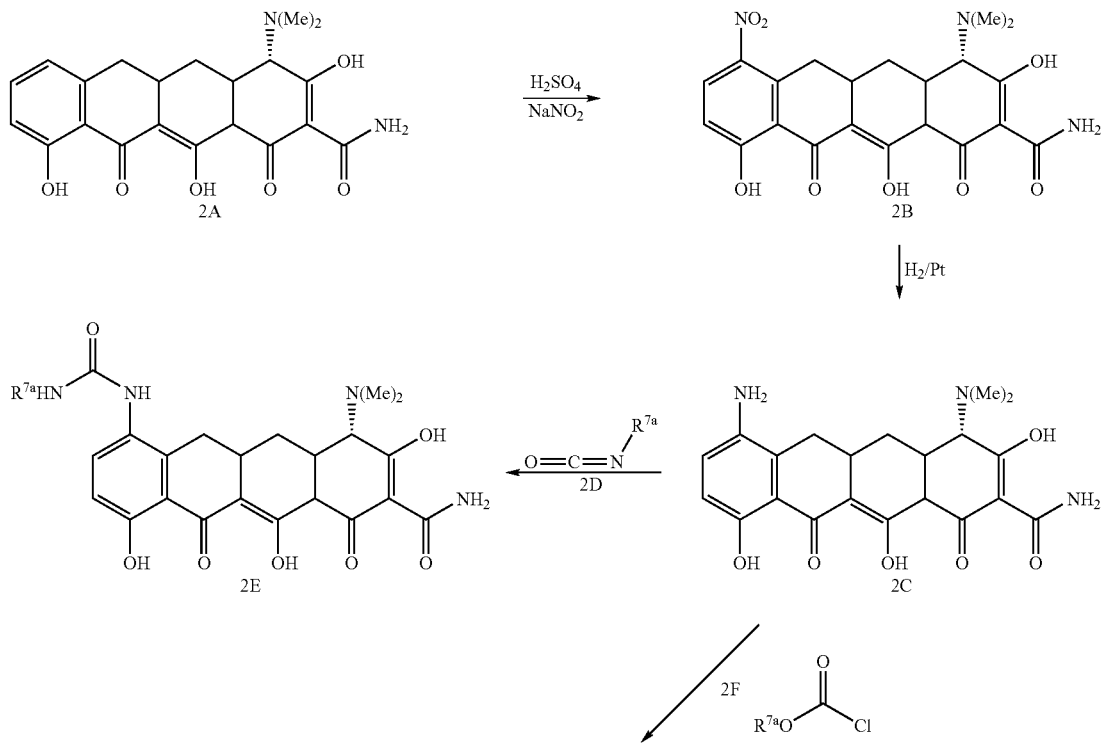

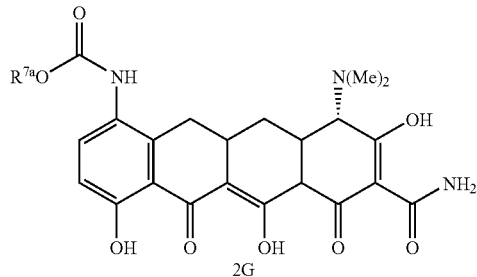

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

SCHEME 3

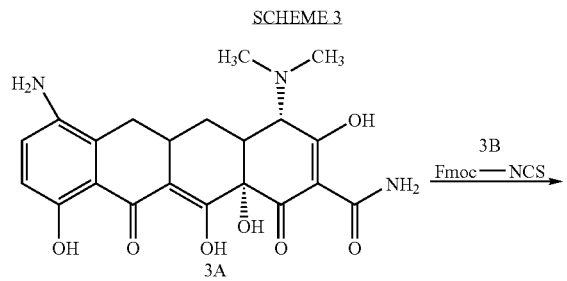

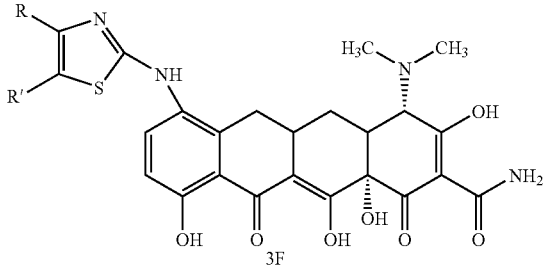

As shown in Scheme 3, tetracycline compounds of the invention, wherein $R^7$ is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

SCHEME 4

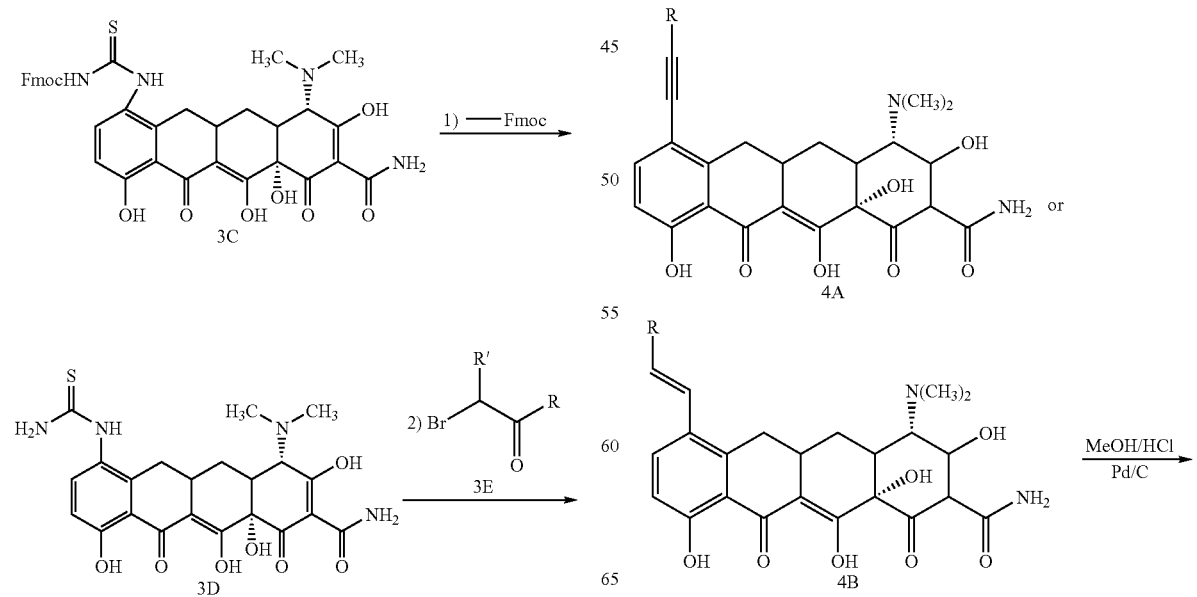

-continued

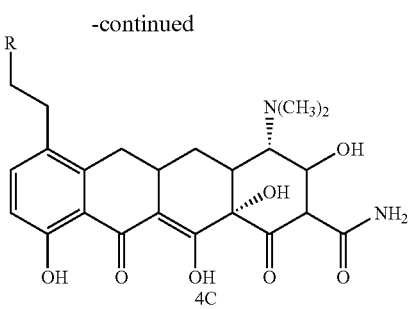
4C 7-alkenyl tetracycline compounds, such as 7-alkynyl sancycline (4A) and 7-alkenyl sancycline (4B), can be hydrogenated to form 7-alkyl substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

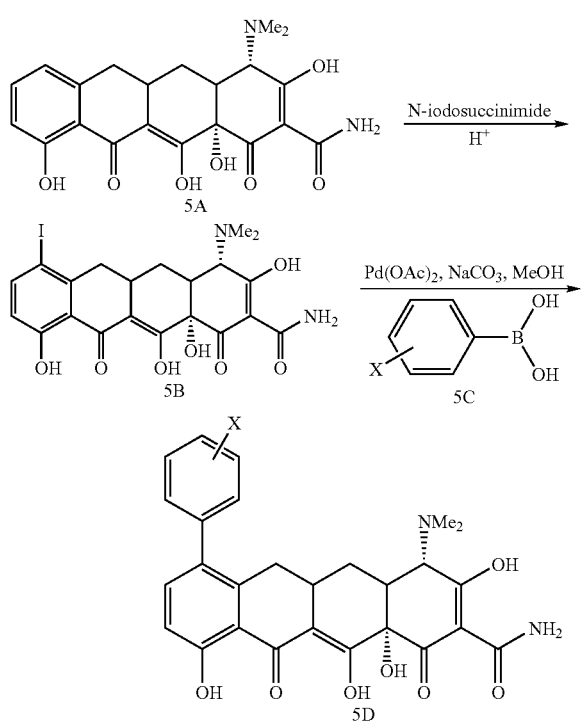

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions. The reaction is quenched, and the resulting 7-iodo sancycline (5B) can then be purified using standard techniques known in the art. To form the aryl derivative, 7-iodo sancycline (5B) is treated with an aqueous base (e.g., $Na_2CO_3$) and an appropriate boronic acid (5C) and under an inert atmosphere. The reaction is catalyzed with a palladium catalyst (e.g., $Pd(OAc)_2$). The product (5D) can be purified by methods known in the art (such as HPLC). Other 7-aryl, alkenyl, and alkynyl tetracycline compounds can be synthesized using similar protocols.

The 7-substituted tetracycline compounds of the invention can also be synthesized using Stille cross couplings. Stille cross couplings can be performed using an appropriate tin reagent (e.g., R—$SnBu_3$) and a halogenated tetracycline compound, (e.g., 7-iodosancycline). The tin reagent and the iodosancycline compound can be treated with a palladium catalyst (e.g., $Pd(PPh_3)_2Cl_2$ or $Pd(AsPh_3)_2Cl_2$) and, optionally, with an additional copper salt, e.g., CuI. The resulting compound can then be purified using techniques known in the art.

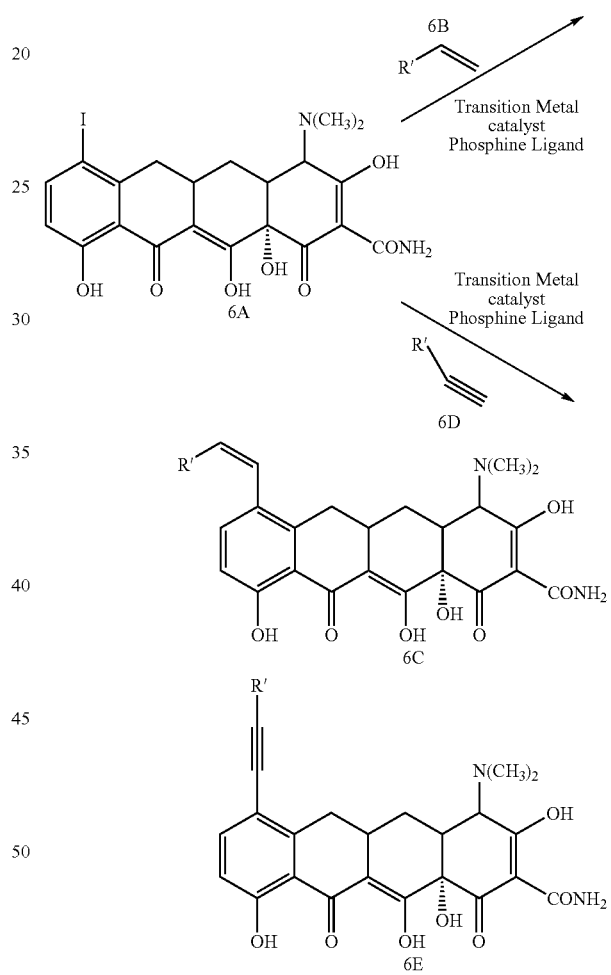

The compounds of the invention can also be synthesized using Heck-type cross coupling reactions. As shown in Scheme 6, Heck-type cross-couplings can be performed by suspending a halogenated tetracycline compound (e.g., 7-iodosancycline, 6A) and an appropriate palladium or other transition metal catalyst (e.g., $Pd(OAc)_2$ and CuI) in an appropriate solvent (e.g., degassed acetonitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E) tetracycline compound can then be purified using techniques known in the art.

SCHEME 7

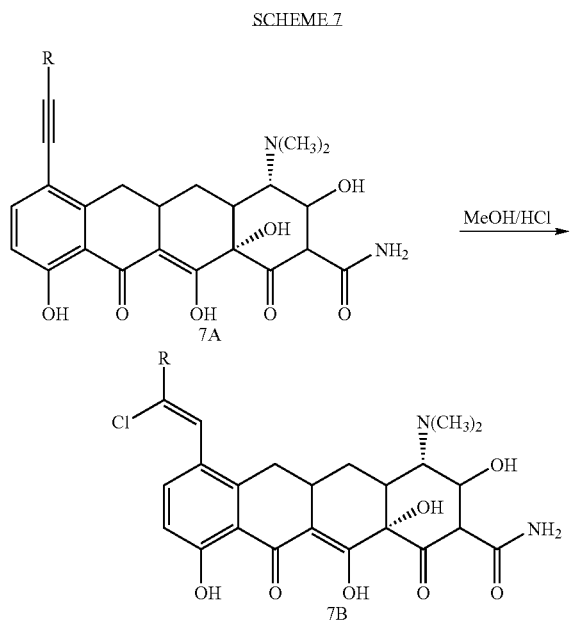

To prepare 7-(2'-Chloro-alkenyl)-tetracycline compounds, the appropriate 7-(alkynyl)-sancycline (7A) is dissolved in saturated methanol and hydrochloric acid and stirred. The solvent is then removed to yield the product (7B).

SCHEME 8

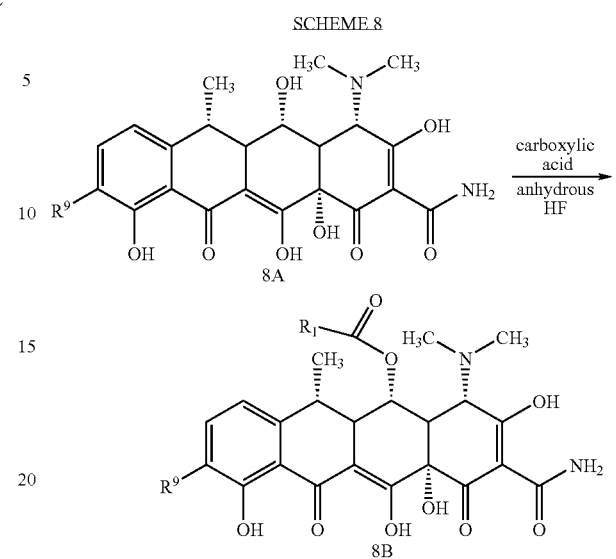

As depicted in Scheme 8, 5-esters of 9-substituted tetracycline compounds can be formed by dissolving the 9-substituted compounds (8A) in strong acid (e.g. HF, methanesulphonic acid, and trifluoromethanesulfonic acid) and adding the appropriate carboxylic acid to yield the corresponding esters (8B).

As shown in Scheme 9 below, 7 and 9 aminomethyl tetracyclines may be synthesized using reagents such as hydroxymethyl-carbamic acid benzyl ester

SCHEME 9

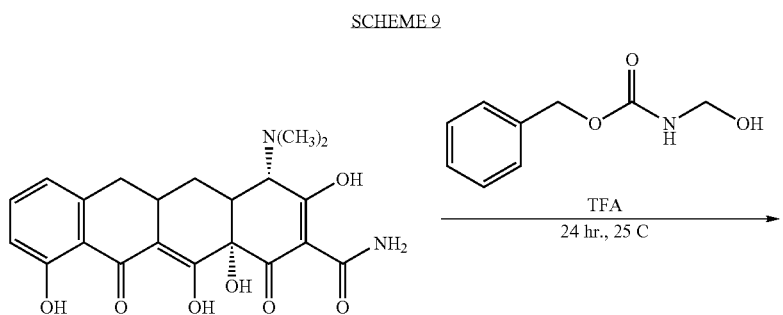

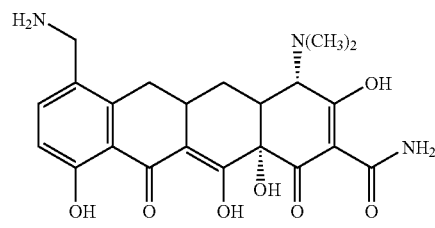

+

-continued

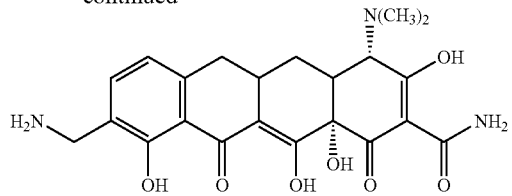

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl(benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO—$) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

6. Methods for Treating Tetracycline Responsive States

The invention also pertains to methods for treating a tetracycline responsive states in subjects, by administering to a subject an effective amount of a tetracycline compound of the invention (e.g., a compound of Formula I, II, III, IV, or otherwise described herein), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention, e.g., a 3, 10, and/or 12a substituted tetracycline compound. Tetracycline compound responsive states include bacterial, viral, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml (as measured by assays known in the art and/or the assay given in Example 2).

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention, e.g., a 3, 10, and/or 12a substituted tetracycline compound. The disorders, diseases and states described in U.S. Pat. Nos. 6,231,894; 6,015,804; 5,919,774; and 5,789, 395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention, e.g., 3, 10, and/or 12a substituted tetracycline compounds.

Examples of matrix metalloproteinase associated states ("MMPAS's") include, but are not limited to, arteriosclerosis, corneal ulceration, emphysema, osteoarthritis, multiple sclerosis (Liedtke et al., Ann. Neurol. 1998, 44:35-46; Chandler et al., J. Neuroimmunol. 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9:541-73; Tryggvason et al., Biochim. Biophys. Acta 1987, 907:191-217; Li et al., Mol. Carcinog. 1998, 22:84-89)), metastasis, acute lung injury, stroke, ischemia, diabetes, aortic or vascular aneurysms, skin tissue wounds, dry eye, bone and cartilage degradation (Greenwald et al., Bone 1998, 22:33-38; Ryan et al., Curr. Op. Rheumatol. 1996, 8; 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amylotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of an IPAS. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843,925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphysema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,839; 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, 2$^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

7. Pharmaceutical Compositions of the Invention

The invention also pertains to pharmaceutical compositions comprising a therapeutically effective amount of a tetracycline compound (e.g., a compound of Formula (I), (II), or (III), or any other compound described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmatic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)]salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays (e.g., aerosols, etc.), creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The compositions of the invention may be formulated such that the tetracycline compositions are released over a period of time after administration.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolaurate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule. It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, II, III, IV, or any other compound described herein, for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Compounds of the invention may be made as described below, with modifications to the procedure below within the skill of those of ordinary skill in the art.

Example 1

Synthesis of Substituted Tetracycline Compounds

7 Iodo Sancycline

One gram of sancycline was dissolved in 25 mL of TFA (trifluoroacetic acid) that was cooled to 0 C (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and 3 mL of MeOH was added to dissolve the residue. The methanolic solution was the added slowly to a rapidly stirring solution of diethyl ether to form a greenish brown precipitate. The 7-iodo isomer of sancycline was purified by treating the 7-iodo product with activated charcoal, filtering through Celite, and subsequent removal of the solvent in vacuo to produce the 7-isomer compound as a pure yellow solid in 75% yield.

MS(M+H) (formic acid solvent) 541.3.

\Rt: Hypersil C18 BDS Column, 11.73

$^1$H NMR (Methanol d$_4$-300 MHz) δ 7.87-7.90 (d, 1H), 6.66-6.69 (d, 1H), 4.06 (s, 1H), 2.98 (s, 6H), 2.42 (m, 1H), 2.19 (m, 1H), 1.62 (m, 4H), 0.99 (m, 2H)

7-Phenyl Sancycline 7-iodosancycline, 150 mg (0.28 mM), Pd(OAc)$_2$ and 10 mL of MeOH are added to a flask with a stir bar and the system degassed 3× using argon. Na$_2$CO$_3$ (87 mg, 0.8 mM) dissolved in water and argon degassed is added via syringe is added along with phenylboronic acid (68 mg, 0.55 mM) in MeOH that was also degassed. The reaction was followed by HPLC for 2 hours and cooled to room temperature. The solution was filtered, and dried to produce a crude mixture. The solid was dissolved in dimethylformamide and injected onto a preparative HPLC system using C18 reverse-phase silica. The fraction at 36-38 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 42% yield as a yellow solid.

Rt 21.6 min: MS (M+H, formic acid solvent): 491.3

$^1$H NMR (Methanol d$_4$-300 MHz) δ 7.87 (d, J=8.86 Hz, 1H), 7.38 (m, 5H), 6.64 (d, 8.87 Hz, 1H), 4.00 (s, 1H), 3.84 (s, 2H), 3.01 (s, 6H), 2.46 (m, 2H), 1.63 (m, 4H), 0.95 (m, 2H)

7-(4'-Iodo-1',3'-carboethoxy-1',3'-butadiene)Sancycline

7-I-Sancycline (1 gm, 1.86 mmol), was dissolved in 25 mL of acetonitrile and was degassed and purged with nitrogen (three times). To this suspension Pd(OAc)$_2$ (20 mg, 0.089 mmol), CuI (10 mg, 0.053 Mmol), (o-tolyl)$_3$P (56 mg, 0.183 mmol) were added and purged with nitrogen. Ethyl propiolate (1 mL) and triethylamine (1 mL) were added to the suspension. It turned to a brown solution upon addition of Et$_3$N. The reaction mixture was then heated to 70 degrees C for two hours. Progress of the reaction was monitored by HPLC. It was then cooled down to room temperature and was filtered through celite. Evaporation of the solvent gave a brown solid, which was then purified on preparative HPLC to give a yellow solid.

7-(2'-Chloroethenyl)-Sancycline

To a solution/suspension of 0.65 g (1 mmol) of 7-iodo sancycline, 0.05 g tetrakis triphenyl phosphinato palladate, 0.012 g palladium acetate, 0.05 g copper (I) iodide in 10 mL acetonitrile, 2 mL triethylamine and 0.5 g trimethylsilyl acetylene was added at room temperature. The reaction proceeded for two hours before being filtered through a celite bed and concentrated. The crude product was purified by preparative HPLC. The collected fractions were concentrated and the residue was taken up in about 1 mL of methanol and 2 mL of HCl saturated methanol. The product was precipitated with ether. The solids were filtered off and dried under reduced pressure. NMR spectroscopy and LC-MS showed that the compound was 7-(2-chloroethenyl)sancycline.

7-(4'-Aminophenyl)Sancycline

To a solution of 200 mg of 7-(4-nitrophenyl)sancycline in 50 mL methanol, 10 mg of 10% palladium on charcoal catalyst was added. The reaction mixture was shaken under 40 psi hydrogen pressure for 2 hours and was then filtered followed by concentration. The residue was further purified by preparative HPLC. 35 mg was isolated as the HCl salt and the structure was proved by MNR and LC-MS to be 7-(4-aminophenyl) sancycline.

7-(NN-Dimethylpropynyl)-Sancycline

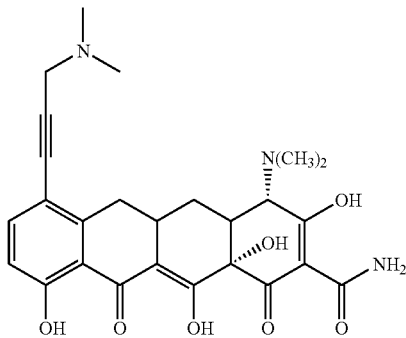

7-I-Sancycline (1 gm, 1.86 mmol), taken in 25 mL of acetonitrile was degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) were added and purged with nitrogen for few minutes. NN-Dimethylpropyne (308 mg, 3.72 mmol) and triethylamine (1 mL) were added to the suspension. It was turned into a brown solution upon addition of Et$_3$N. The reaction mixture was then heated to 70° C. for 3 hours. Progress of the reaction was monitored by HPLC. It was then cooled down to room temperature and was filtered through celite. Evaporation of the solvent gave a brown solid, which was then purified on preparative HPLC to give a yellow solid. The structure of this compound has been characterized using 1H NMR, HPLC, and MS.

7-(2'-Chloro-3-Hydroxypropenyl)-Sancycline

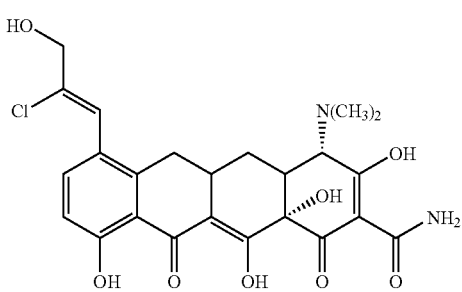

7-(alkynyl)-sancycline (100 mg) was taken in 20 ml of saturated MeOH/HCl and stirred for 20 min. The solvent was then evaporated to give a yellow powder. The structure of this compound has been characterized using 1H NMR, HPLC, and MS.

7-(3'-Methoxyphenylethyl)-Sancycline

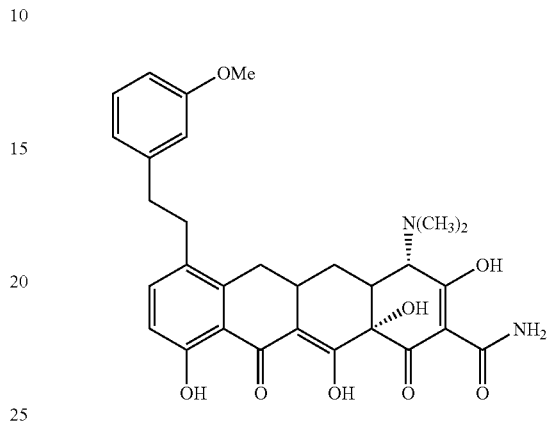

7-(3'-Methoxyphenylethynyl)-sancycline (1 mmol)/was taken in saturated solution of MeOH/HCl. To this solution 10% Pd/C was added and was subjected to hydrogenation at 50 psi for 12 hrs. It was then filtered through celite. The solvent was evaporated to give a yellow powder. Finally, it was precipitated from MeOH/diethylether. The structure of this compound has been characterized using 1H NMR, HPLC, and MS.

(2-Dimethylamino-Acetylamino)-Sancycline

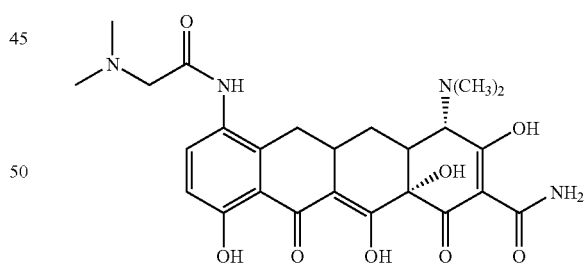

NN-Dimethylglycine (1.2 mmol) was dissolved in DMF (5 mL) and O-Benzotriazol-1-yl-N,N,N',N',-tetramethyluronium hexafluorophosphate (HBTU, 1.2 mmol) was added. The solution was then stirred for 5 minutes at room temperature. To this solution, 7-aminosancycline (1 mmol) was added, followed by the addition of diisopropylethyl amine (DIEA, 1.2 mmol). The reaction was then stirred at room temperature for 2 hours. The solvent, DMF, was removed on vacuum. The crude material was dissolved in 5 mL of MeOH and filtered using autovials and purified using preparative HPLC. The structure of the product has been characterized using 1H NMR, HPLC, and MS.

7-(N-Methylsulphonamidopropargylamine)Sancycline

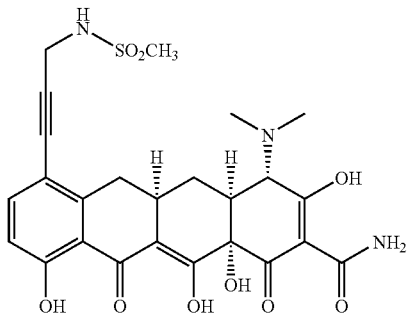

To a mixture of 7-iodosancycline mono trifluoroacetic acid salt (1 g; 1.53 mmoles), palladium II acetate (17.2 mg; 0.076 mmoles), tetrakis triphenylphosphine palladium (176.8 mg; 0.153 mmoles), and copper (I) iodide (49 mg; 0,228 mmoles) was added 15 ml of reagent grade acetonitrile in a clean dry 2 necked round bottom flask. The reaction was purged with a slow steam of argon gas, with stirring, for 5 minutes before the addition (in one portion as a solid) of N-methylsulphonamidopropargyl amine. The sulphonamide was prepared by a method known in the art (J. Med. Chem 31(3) 1988; 577-82). This was followed by one milliliter of triethylamine (1 ml; 0.726 mg; 7.175 mmoles) and the reaction was stirred, under an argon atmosphere, for approximately 1.0 hour at ambient temperature. The reaction mixture was suctioned filtered through a pad of diatomaceous earth and washed with acetonitrile. The filtrates were reduced to dryness under vacuo and the residue was treated with a dilute solution of trifluoroacetic acid in acetonitrile to adjust the pH to approximately 2. The residue was treated with more dilute trifluoroacetic acid in acetonitrile, resulting in the formation of a precipitate, which was removed via suction filtration. The crude filtrates were purified utilizing reverse phase HPLC with DVB as the solid phase; and a gradient of 1:1 methanol/acetonitrile 1% trifluoroacetic acid and 1% trifluoroacetic acid in water. The appropriate fractions were reduced to dryness under reduced pressure and solid collected. The product was characterized via $^1$H NMR, mass spectrogram and LC reverse phase.

7-(2'-methoxy-5'-formylphenyl)sancycline

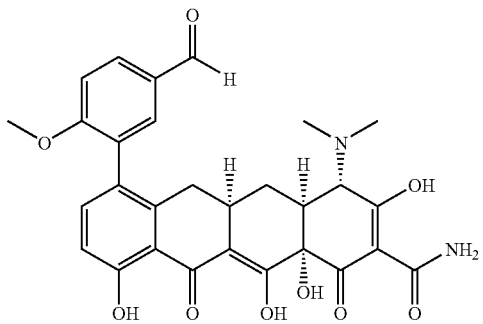

7-iodo-sancycline (1 g, 1.53 mmol), Pd(OAc)$_2$ (34 mg, 0.153 mmol), and MeOH (50 mL) were combined in a 250 mL 2 neck round bottom flask equipped with a condenser and argon line. The solution was then purged with argon (15 min) while heated in an oil bath to approximately 70° C. Sodium carbonate (482 mg, 4.58 mmol) was dissolved in water (3-5 mL) and added to reaction flask. The flask was then purged with argon for another 5 minutes. 2-Methoxy-5-formylphenyl boronic acid (333 mg, 1.83 mmol) was dissolved in MeOH (5 mL) and added to reaction flask. The flask was then purged again with argon for 10 minutes. The reaction was monitored to completion within 3 hours. The contents of the flask were filtered through filter paper and the remaining solvent was evacuated. To make the hydrochloric acid salt, the residue was dissolved in MeOH (sat. HCl) to make the HCl salt. The solution was then filtered and the solvent was evacuated. The product was then characterized by $^1$H NMR, LC-MS.

7-(2'-Methoxy-5'-N,N'-Dimethylaminomethylphenyl)Sancycline

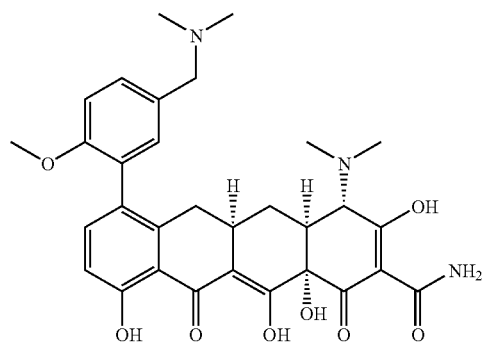

7-(2'-methoxy-5'-formylphenyl)sancycline (1 g, 1.82 mmol), dimethylamine HCl (297 mg, 3.64 mmol), triethylamine (506 µL, 3.64 mmol), and 1,2-DCE (7 mL) were combined in a 40 mL vial. The contents were dissolved within several minutes of shaking or stirring. Sodium triacetoxyborohydride (772 mg, 3.64 mmol) was then added as a solid. The reaction was monitored by HPLC and LC-MS and was complete within 3 hours. The reaction was quenched with MeOH (20 mL) and the solvent was subsequently evacuated. The residue was redissolved in 3 mL DMF and separated on a C-18 column. Fractions from the prep column dried down in-vacuo and the HCl salt was made by dissolving contents in methanol (sat. HCl). The solvent was reduced and a yellow powder formed. Characterized by $^1$H NMR, LC-MS, BPLC.

7-Furanyl Sancycline

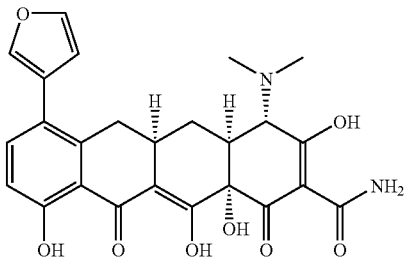

7-iodo sancycline (1.3 mg) and Pd(OAc)$_2$ were taken in 100 mL of methanol and purged with argon for five minutes at 70° C. To this solution was added a solution of sodium carbonate (44 mg) in water (previously purged with argon). A yellow precipitate was obtained and the mixture was heated for another ten minutes. 3-Furanyl boronic acid (333 mg, solution in DMF, purged with argon) was then added and the mixture was heated for another two hours at 70° C. The reaction was monitored by MPLC/MS. When the reaction was complete, the mixture was filtered through celite and the solvent was removed to give a crude material. The crude material was purified by precipitating it with ether (200 ml). The yellow precipitate was filtered and purified using preparative HPLC. The hydrochloride salt was made by dissolving the material in MeOH/HCl and evaporating to dryness. The identity of the resulting solid was confirmed using HPLC, MS, and NMR.

7-Cyano Sancycline

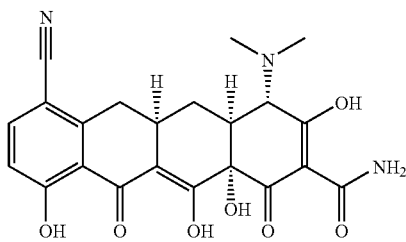

7-iodo sancycline (1.3 g) was dissolved in NMP (15 mL) and CuCN (344 mg) was added. The reaction mixture was stirred at 80° C. for 15/16 hours overnight. The reaction mixture was diluted with methanol and centrifuged to yield a grey white precipitate. The reaction mixture was then passed through Celite and washed with additional methanol. The filtrate was then concentrated and precipitated with ether. The solid obtained was then purified using preparative HPLC to yield 7-cyano sancycline in a 50/50 mixture of epimers. The structure of the product was confirmed using mass spectra and NMR.

7,9-Diiodosancyline 30.0 mL of concentrated sulfuric acid was added to 1.00 g of sancycline hydrochloride hemihydrate with stirring and the solution cooled to 0° C. 1.09 g of N-iodosuccinimide was added portionwise to the solution over one hr and the reaction mixture monitored by HPLC and TLC. The reaction mixture was poured into 250 mL of ice water, extracted three times with n-butanol, and the solvent removed under reduced pressure. The crude residue was purified by preparative HPLC yielding 787 mg (61%) of 7-iodosancycline and 291 mg (22%) of 7,9-diiodosancycline as yellow and dark yellow crystals respectively.

MS (FAB): m/z 667 (M+H)

$^1$H NMR (Methanol d-4, 300 MHz) δ 8.35 (s, 1H), 3.78 (s, 1H), 3.33 (s, 2H), 2.88 (s, 7H), 2.41 (m, 2H), 1.41 (m, 5H).

7,9-Bis(3,4-Methylenedioxyphenyl)-Sancycline

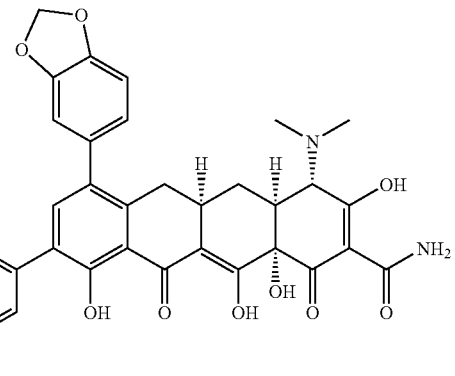

577 mg (0.74 mmol) 7,9-diiodo sancycline and 8.3 mg (0.37 mmol) palladium acetate were dissolved in 25 ml methanol, under a nitrogen atmosphere. The solution was warmed to 60° C. After stirring for ten minutes 234 mg (2.22 mmol), sodium carbonate was added followed by 246 mg (1.48 mmol) of 3,4-methylenedioxyphenyl boronic acid. The reaction was complete in 4 hours. The reaction mixture was filtered through a celite bed and concentrated under reduced pressure. This crude product was purified by preparative liquid chromatography using a C$_{18}$ stationary phase with eluent A: 0.1% TFA in water and eluent B: 0.1% TFA in acetonitrile. 60 mg pure product was isolated.

7-Tetramethylsilylethynyl-Sancycline

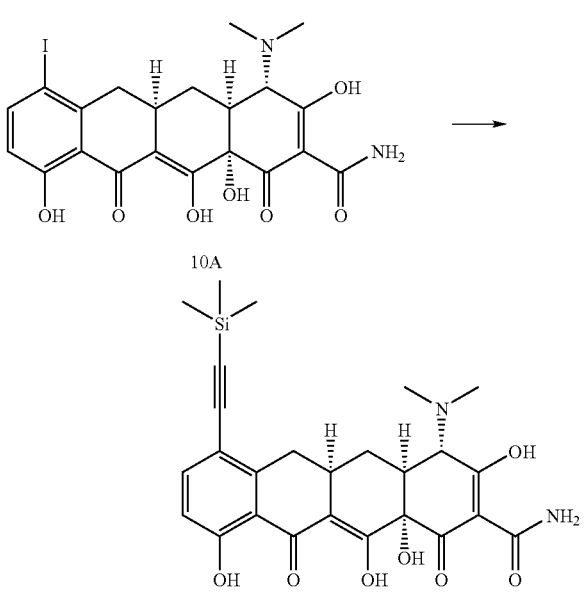

To a solution of 6.54 g (10 mmol) 7-iodo-sancycline trifluoroacetate 500 mg tetrakis-triphenylphosphino-palladate, 500 mg copper(I) iodide, 100 mg palladium acetate and 30 ml triethylamine 3 ml trimethylsilyl-acetylene was added. The reaction mixture was stirred at room temperature for two hours than filtered through a celite bed and concentrated. The dry material was picked up in methanol, the insolubles were filtered out. The solution was concentrated to recover 6.8 g of the product (10B).

7-Ethynyl-Sancycline

SCHEME 11

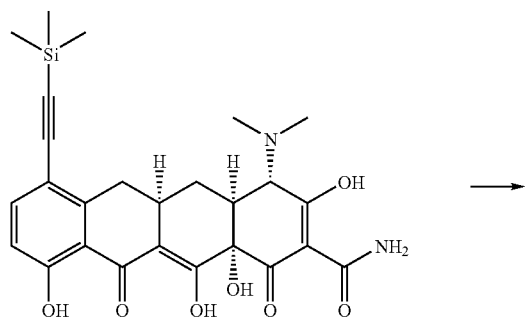

10B

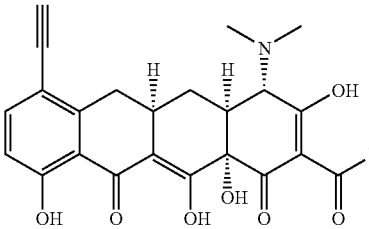

11B

7-Tetramethylsilylethynyl-sancycline (10B) is dissolved in 300 ml methanol, and stirred at 40° C. with 6.8 g potassium carbonate. When no starting material could be detected by HPLC (~3 hours), the reaction mixture was cooled in an ice/water bath and solids were removed by filtration. The structure of the alkyne (11B) was confirmed by LCMS. 11B was then used without further purification in the next step.

7-Ethyl-Sancycline

SCHEME 12

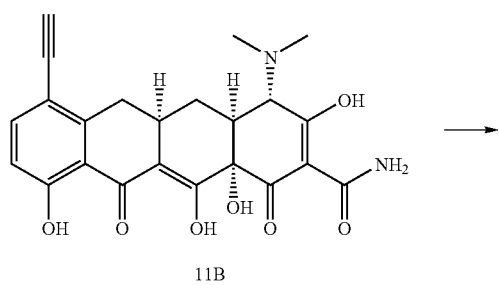

11B

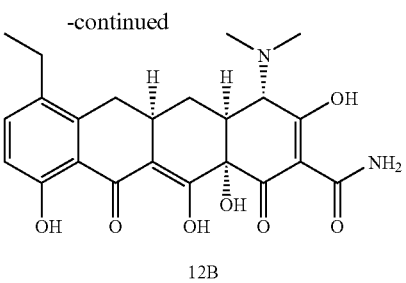

12B

10% palladium catalyst on charcoal (1 g) was added to 7-ethynyl sancycline (11B) in a saturated methanol hydrochloric acid solvent. The mixture was placed in a hydrogenator under 50 psi hydrogen pressure. The reaction was completed in ~8 hours. The catalyst was filtered off, and the resulting solution was concentrated. The crude product was purified by preparative liquid chromatography using a $C_{18}$ stationary phase with eluent A: 0.1% TFA in water and eluent B: 0.1% TFA in acetonitrile. The combined clean fractions are concentrated and hydrochloric acid saturated isopropanol added. The pure product is precipitated by addition of diethylether and filtered off. After drying under reduced pressure 3.2 g of 7-ethyl-sancycline (12B) was isolated.

7-Ethyl-9-Iodo-Sancycline

SCHEME 13

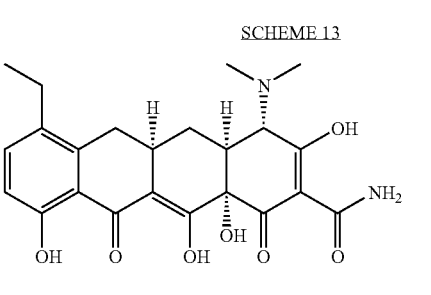

7-Ethyl-Sancycline (12B, 6.7 mmol, 3.2 g) was dissolved in 75 ml methanesulfonic acid at room temperature. N-iodo succinimide (13B, 13.5 mmol, 3.05 g) was added over two hours in 6 portions. After two hours diethyl ether was added, and the precipitate was filtered off and dried. The crude product was purified by preparative liquid chromatography using

7-Ethyl-9-Cyclohexenylethynyl-Sancycline

SCHEME 14

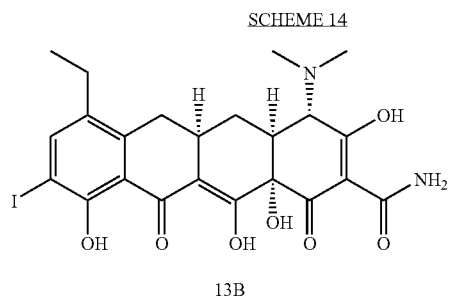

13B

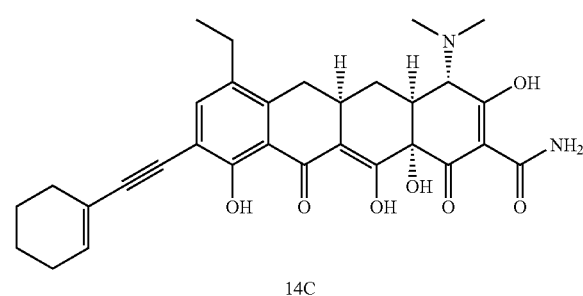

14C

To a solution of 7-ethyl-sancycline (500 mg, 1.13 mmol), 50 mg tetrakis-triphenylphosphino-palladate, 50 mg copper (I) iodide, 10 mg palladium acetate and 3 ml triethylamine 0.1 ml cyclohexenyl-acetylene was added. The reaction mixture was stirred at 60° C. for one hour, filtered through a celite bed and concentrated. The dry material was dissolved in methanol and filtered. The solution was then concentrated and purified using preparative liquid chromatography. The preparative liquid chromatography used a $C_{18}$ stationary phase with eluent A: 0.1% TFA in water and eluent B: 0.1% TFA in acetonitrile. 100 mg of the product was isolated.

SCHEME 15

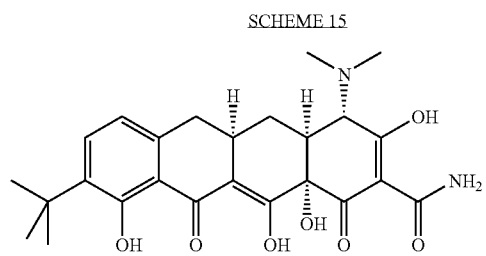

15A

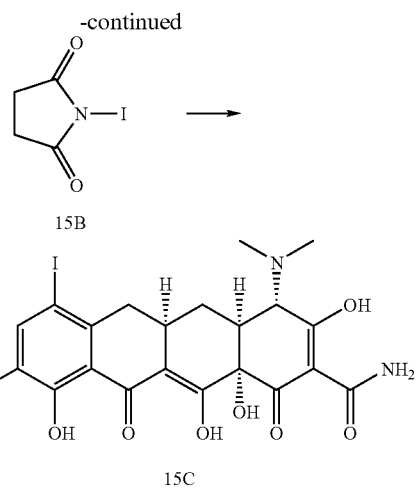

15C 9-tbutyl-sancycline (15A, 1.13 g, 2 mmol) was dissolved in 5 ml methanesulfonic acid (0.448, 2 mmol). N-iodosuccinimide (15B) was added at room temperature over one hour in four portions. The product (15C) was precipitated with diethyl ether, filtered off and used in other reaction without further purification.

SCHEME 16

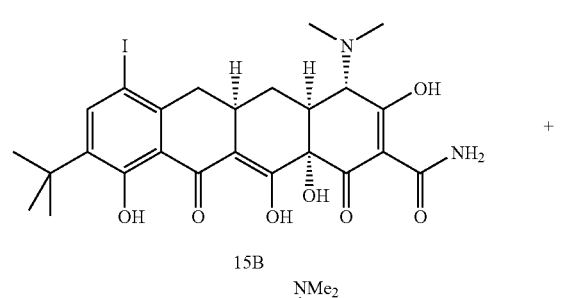

15B

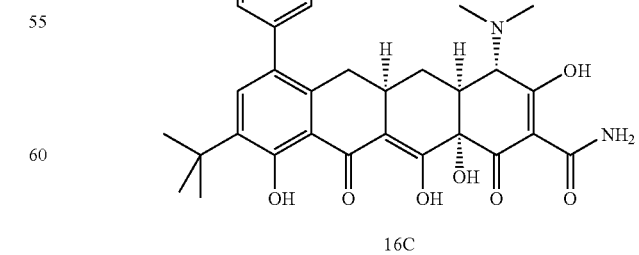

16C

7-Iodo-9-t-butyl-sancycline (15B, 710 mg, 1.0 mmol) and palladium acetate (22.4 mg, 0.1 mmol) were dissolved in 25 ml of methanol under a nitrogen atmosphere. Cesium carbonate (3.25 g, 10 mmol) and 2-methoxy-5-dimethylaminomethylphenyl-boronic acid (16B, 0.435 g, 0.15 mmol) were added. The reaction mixture was stirred at 60° C. for two hours and then filtered through a celite bed and concentrated under reduced pressure. The crude product was purified by preparative liquid chromatography using a $C_{18}$ stationary phase with eluent A: 0.1% TFA in water and eluent B: 0.1% TFA in acetonitrile. 210 mg of the product (16C) was isolated.

7-(para-tert-butyl phenyl)-9-aminomethyl sancycline

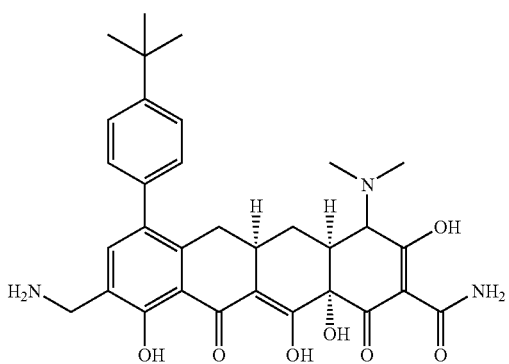

7-para-tert-butyl phenyl sancycline (5.0 g) was dissolved in trifluoroacetic acid (300 mL). Three equivalents of HMBC was added and the reaction was stirred at room temperature. After 72 hours, HPLC indicated that the reaction was complete. The reaction mixture was filtered to give a brown liquid which was subsequently dissolved in methanol and precipitated in diethyl ether. The solid was then purified using HPLC and the product was identified using NMR and mass spectra.

7-Furanyl-9-nitro-Sancycline

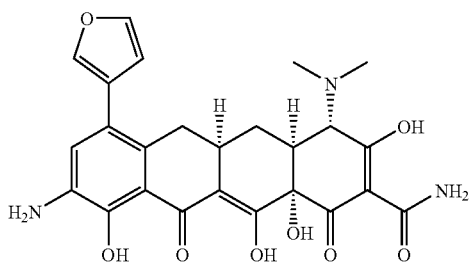

500 milligrams of 9-$NO_2$ sancycline was taken in 20 mL of TFA and cooled down in an ice bath. To this solution, NIS (300 mg) was added in portions and stirred at room temperature for three hours. Once the reaction was completed, 7-iodo-9-$NO_2$ sancycline was precipitated in diethyl ether. The yellow powder was then filtered and dried in vacuo.

7-Iodo-9-nitro-sancycline (585 mg) and PD(OAc)$_2$ (22 mg) were taken in 20 mL of methanol and purged with argon for five minutes. To this solution, Na$_2$CO$_3$ (420 mg, solution in 5 mL H$_2$O, purged with argon), was added and a yellow precipitate was obtained. The solution was stirred at 55-60° C. for five minutes. To this solution, 3-furanyl boronic acid (160 mg in 5 mL of DMF, purged with argon) was added and the reaction mixture was heated at 70° C. for three hours. The reaction mixture was then passed through celite. Evaporation of the solvent gave a brown solid, which was then recrystallized using a mixture of methanol and ether to yield 7-furanyl 9-nitro sancycline.

7-Furanyl 9-nitro sancycline (500 mg) was taken in 30 ml of methanol. To this solution, PtO$_2$ (15 mg) was added and hydrogenated at 40 psi for three hours. It was then filtered through celite. The crude material was purified using preparative HPLC to yield 7-furanyl 9-amino sancycline.

Preparation of 9-Iodominocycline

To 200 ml of 97% methanesulfonic acid was slowly added, at ambient temperature, portionwise [30 g; 56.56 mM] of minocycline-bis-hydrochloride salt. The dark yellow brown solution was then stirred at ambient temperature while [38 g; 169.7 mM] of N-iodosuccinimide was added, in six equal portions, over 3.0 hours time. The reaction was monitored via analytical LC, noting the disappearance of the starting material.

The reaction was slowly quenched into 2 L of ice cold water containing [17.88 g; 1134.1 mM] of sodium thiosulfate with rapid stirring. This quench was stirred for approximately 30 minutes at ambient temperature. The aqueous layer was then extracted with 6×200 ml of ethyl acetate before the aqueous was poured onto [259.8 g; 3.08M] of sodium hydrogen carbonate containing 300 ml of n-butanol. The phases were split and the aqueous extracted with 4×250 ml of n-butanol. The organic fractions were combined and washed with 3×250 ml of water and once with 250 ml of saturated brine. The resulting organic phase was reduced to dryness under reduced pressure. The residue was suspended in methanol (~600 ml) and anhydrous HCl gas was bubbled into this mixture until solution occurred This solution was reduced to dryness under reduced pressure. The filtrates were reduced to dryness under reduced pressure. The resulting material was triturated with 300 ml of methyl t-butyl ether and isolated via filtration. This material was redissolved in 300 ml of methanol and treated with 0.5 g of wood carbon, filtered and filtrates reduced to dryness under reduced pressure. The material was again powdered under methyl t-butyl ether, isolated via suction filtration and washed with more ether, and finally hexanes. The material was vacuum dried to give 22.6 g of a light yellow brown powder.

General Procedure For Preparation of 9-Alkynyl Minocycline Compounds 1 mmol 9-iodo minocycline, 50 mg tetrakis triphenylphosphinato palladate, 12 mg palladium acetate, 32 mg copper (I) iodide are dissolved/suspended in 10 ml acetonitrile. 2 to 5 ml triethylamine and 3 to 5 mmol alkynyl derivative is added. The reaction mixture is vigorously stirred between ambient temperature to 70° C. The reaction time is 2-24 hours. When the reaction is completed the dark suspension is filtered through a celite bed and concentrated. The crude product is purified by prep HPLC. The combined fractions are concentrated and taken up in ~1 ml methanol. ~3 ml HCl saturated methanol is added, and the product is precipitated with ether.

General Procedure For Preparation of 9-Aryl Minocycline Compounds 0.15 mmol of 9-iodominocycline, PdOAc (3.2 mg), 229 µl 2M Na$_2$CO$_3$ and 2 equivalents of phenyl boronic acid were dissolved/suspended in 10 ml methanol. The reaction flask was purged with argon and the reaction run for a minimum of four hours or until HPLC monitoring shows consumption of starting material and/or the appearance of products. The suspension was filtered through celite, and subject to purification by prep HPLC on a divinylbenzene column.

9-(4-Trifluoromethoxyphenylureido)-Methyl Minocycline

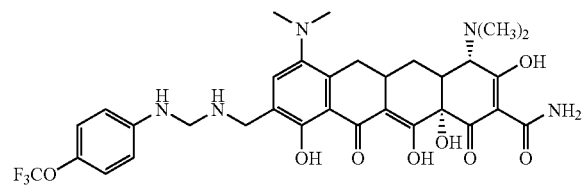

To 3 mL of dimethylformamide was added 150 mg (0.25 mmol) of 9-methyl aminominocyline trihydrochloride and 67 mL (0.50 mmol) of triethylamine at 25° C. With stirring, 75 mL (0.50 mmol) of 4-trifluoromethoxyphenylisocyanate was added and the resulting reaction mixture was stirred at 25° C. for two hours. The reaction was monitored by analytical HPLC (4.6×50 mm reversed phase Luna C18 column, 5 minute linear gradient 1-100% B buffer, A buffer was water with 0.1% trifluoroacetic acid, B buffer was acetonitrile with 0.1% trifluoroacetic acid). Upon completion, the reaction was quenched with 1 mL of water and the pH adjusted to approximately 2.0 with concentrated HCl. The solution was filtered and the compound purified by preparative HPLC. The yield of the product was 64 mg (37% yield). The purity of the product was 95% determined by LCMS (M+1=690).

9-(4' Carboxy phenyl)Minocycline

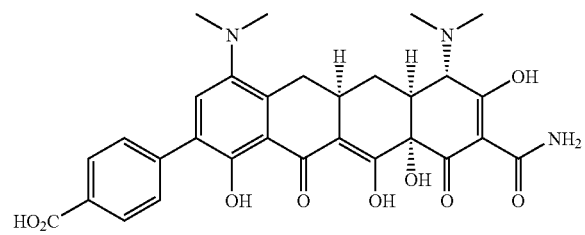

In a clean, dry reaction vessel, was placed 9-iodominocycline [500 mg; 0.762 mmoles] bis HCl salt, palladium (II) acetate [17.2 mg; 0.076 mmoles] along with 10 ml of reagent grade methanol. The solution was immediately purged, with stirring, with a stream of argon gas for approximately 5 minutes. The reaction vessel was brought to reflux and to it was sequentially added via syringe 2M potassium carbonate solution [1.91 ml; 3.8 mmoles], followed by a solution of p-carboxyphenyl boronic acid [238.3 mg; 1.53 mmoles] in 5 ml of reagent DMF. Both of these solutions were previously degassed with argon gas for approximately 5 minutes. The reaction was heated for 45 minutes, the progress was monitored via reverse phase HPLC. The reaction was suctioned filtered through a pad of diatomaceous earth and washed the pad with DMF. The filtrates were reduced to an oil under vacuum and residue treated with t-butylmethyl ether. Crude material was purified via reverse phase HPLC on DVB utilizing a gradient of water and methanol/acetonitrile containing 1.0% trifluoroacetic acid. The product confirmed by mass spectrum: found M+1 578.58; the structure corroborated with 1H NMR.

9-(4'-Acetyl phenyl)Minocycline

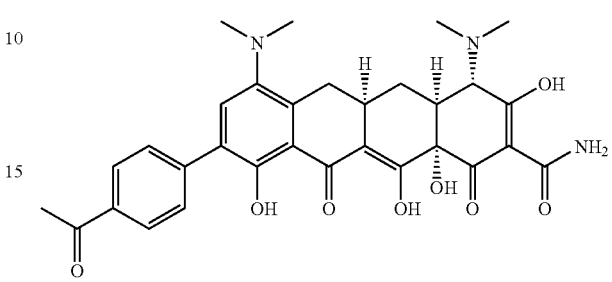

In a clean, dry reaction vessel, was placed 9-iodominocycline (0.762 mmoles) bis HCl salt, palladium (II) acetate (0.076 mmoles) along with 10 ml of reagent grade methanol. The solution was immediately purged, with stirring, with a stream of argon gas for approximately 5 minutes. The reaction vessel was brought to reflux and to it was sequentially added via syringe 2M potassium carbonate solution, followed by a solution of p-acetylphenyl boronic acid (1.53 mmoles) in 5 ml of reagent DMF. Both of these solutions were previously degassed with argon gas for approximately 5 minutes. The reaction was heated for 45 minutes, the progress was monitored via reverse phase HPLC. The reaction was suctioned filtered through a pad of diatomaceous earth and washed the pad with DMF. The filtrates were reduced to an oil under vacuum and residue treated with t-butylmethyl ether. Crude material was purified via reverse phase HPLC on DVB utilizing a gradient of water and methanol/acetonitrile containing 1.0% trifluoroacetic acid.

N-Benzyl-9'-minocyclinyl guanidine

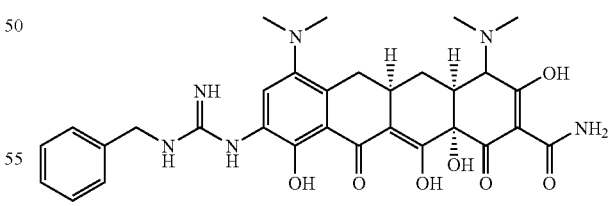

To a stirred solution of 9-aminominocycline (1.6 mmol) in 30 mL of acetonitrile, benzylcyanimide (6.0 mmol) was added in one portion. The reaction mixture was first heated to refluxed at 60° C. for several hours, and continued at room temperature for 4-5 days. The guanidino product was subsequently isolated, and identified using MS, NMR and HPLC.

9-Minocycline methyl ester

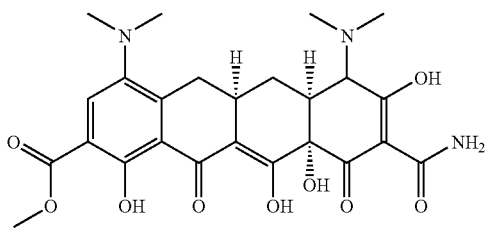

In the Parr apparatus were placed: 9-iodosancycline trifluoroacetic acid salt (0.8 g, 1.17 mmol), NaOAc (0.64 g, 4 eq.), Pd(dppf)$_2$Cl$_2$, and CH$_2$Cl$_2$ (48 mg, 5%). The apparatus was closed, purged with CO, and then filled with CO under 450 psi. The reaction mixture was stirred for four hours at 80° C. It was then acidified with TFA and concentrated in vacuo. The product was purified by HPLC. A mixture of 3:1 epimers was obtained. The yield was 188 mg of product.

9-N-piperdinyl-minocycline

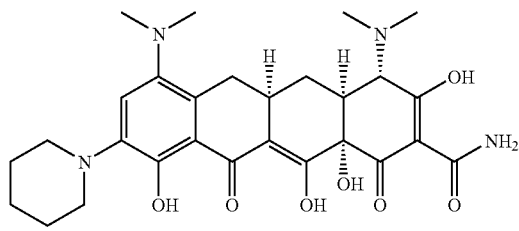

Concentrated H$_2$SO$_4$ (2 mL) was added slowly to a stirred solution of gluteraldehyde (1 mL). Water (0.8 g) was added and stirred at room temperature for eighteen hours and heater to 70° C. for two hours. The mixture was then cooled to room temperature. The solution was then transferred to a solution of 9-amino minocycline in DMF (5 ml) and stirred at room temperature for two days until all starting material was consumed, as indicated by HPLC. The product was isolated and purified using standard techniques. The structure of the product was confirmed by NMR and mass spec.

2-[4-(5-Minocyclin-9-yl-furan-2-ylmethyl)-piperazin-1-yl]-ethanol

Na$_2$CO$_3$ (0.64 g) in water (5 mL) was added to a degassed solution of 9-iodo-minocycline hydrochloride (1 g) and Pd(OAc)$_2$ (100 mg) in methanol (10 mL). The reaction was stirred for five minutes at 60° C. 2-Formyl furan-5-boronic acid (0.3 g) in methanol (10 mL) was then added, and the reaction was allowed to proceed for four hours. The mixture was then filtered and concentrated to give a brown solid (9-(2'formyl furanyl)-minocycline).

The brown solid (9-(2'formyl furanyl)-minocycline, 1 g) was dissolved in 20 mL of methanol and acetic acid (2 mL) and hydroxyethyl piperazine (1 mL) was added and stirred for ten minutes at room temperature. The reaction was quenched with ether (200 mL), and the organic layer was then washed and concentrated to yield a brown oil. The brown oil was the dissolved in methanol (10 mL) and water. The mixture was the chromatographed using a CH$_3$CN gradient to yield the product, 2-[4-(9-Minocyclin-2-yl-furan-2-ylmethyl)-piperazin-1-yl]-ethanol. The product was confirmed using MS, NMR, and HPLC.

9-N-morpholinyl minocycline

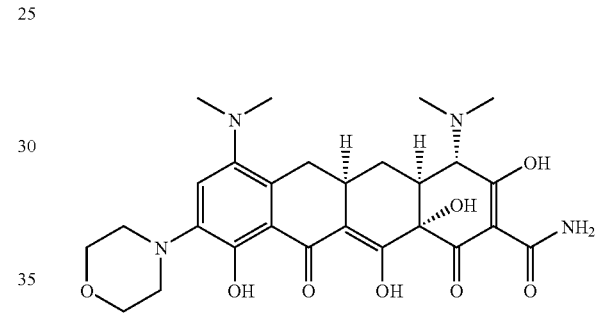

NaCNBH$_3$ (200 mg) was added to a stirred solution of 9-amino minocycline H$_2$SO$_4$ (1 g) in methanol (4.9 mL) and acetic acid 91 mL) and stirred for five minutes at room temperature. (2-Oxo-ethoxy)-acetaldehyde (10 mL) was added dropwise and stirred for fifteen minutes at room temperature. The reaction mixture was concentrated with out heat and the residue was dissolved in 20 mL of methanol and TFA (0.5 mL). The product was obtained using preparative HPLC and converted to the HCl salt. The product was confirmed using mass spectra and NMR.

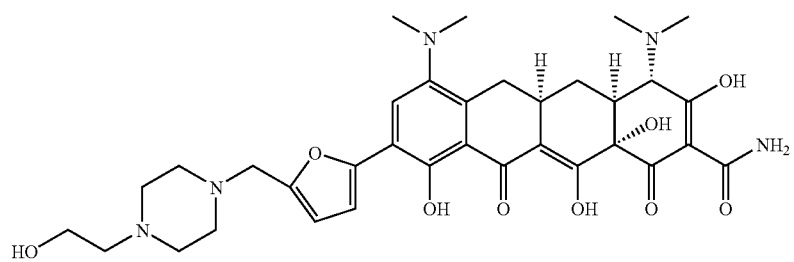

N-Benzyl-N',N'-dimethyl-N-(5-minocyclin-9-yl-furan-2-ylmethyl)-ethane-1,2-diamine

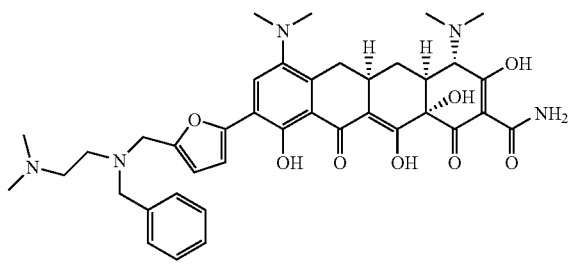

Na$_2$CO$_3$ (0.64 g) in water (5 mL) was added to a degassed solution of 9-iodo-minocycline hydrochloride (1 g) and Pd(OAc)$_2$ (100 mg) in methanol (10 mL). The reaction was stirred for five minutes at 60° C. 2-Formyl furan-5-boronic acid (0.3 g) in methanol (10 mL) was then added, and the reaction was allowed to proceed for four hours. The mixture was then filtered and concentrated to give a brown solid (9-(2'formyl furanyl)-minocycline).

The brown solid (9-(2'formyl furanyl)-minocycline, 1 g) was dissolved in 20 mL of methanol and acetic acid (2 mL) and N'-benzyl-N,N-dimethyl ethylenediamine (1 mL) was added and stirred for ten minutes at room temperature. The reaction was quenched with ether (200 mL), and the organic layer was then washed and concentrated to yield a brown oil. The brown oil was the dissolved in methanol (10 mL) and water. The mixture was the chromatographed using a CH$_3$CN gradient to yield the product, N-Benzyl-N',N'-dimethyl-N-(5-minocyclin-9-yl-furan-2-ylmethyl)-ethane-1,2-diamine. The product was confirmed using MS, NMR, and HPLC.

[4S-(4α,12aα)]-9-Amino-4-dimethylamino-3,5,10,12,12a-pentahydroxy-6-methyl-1,11-dioxo-1,4,4a,5,5a,6,11,12a-octahydro-naphthacene-2-carboxamide 9-Nitro doxycycline hydrochloride was synthesized as previously described. 1.0 g was hydrogenated in 40 mL MeOH, 1 mL conc. HCl and 100 mg of 10% Pd/C for 3 hr under 30 psi of H$_2$. The solution was filtered through Celite and the filtrate evaporated in vacuo to obtain 0.9 g of the dihydrochloride salt as a yellow solid. Yield=82%. $^1$H NMR (CD$_3$OD, 300 MHz): δ 7.62 (d, 1H, J=8.08 Hz); 7.14 (d, 1H, J=8.08); 4.42 (s, 1H); 3.6 (dd, 1H); 2.98, 2.90 (each s, 3H); 2.84 (d, 1H); 2.72 (m, 1H); 2.59 (dd, 1H); 1.56 (d, 3H). HRMS calcd (C$_{22}$H$_{26}$N$_3$O$_8$+H) 460.1720, found 460.1739.

[4S-(4α,12aα)]-9-(Diazonium)-4-dimethylamino-3,5,10,12,12a-pentahydroxy-6-methyl-1,11-dioxo-1,4,4a,5,5a,6111,12a-octahydro-naphthacene-2-carboxamide A flask was charged with 100 mg of compound 10 and dissolved with 4 mL of 0.1 N HCl. The solution was cooled to 0° C. and 35 μL of butyl nitrite was added with stirring. After 1 h, the bright red mixture was added dropwise to 100 mL of cold anhydrous Et$_2$O. The product was collected by filtration under ether as an orange solid. Analytical R$_t$=1.90 Method A. LC/MS(ESI): 472 (M+H).

General Diazonium Reaction Procedure 0.1 g of 9-diazonium salt generated in situ (HCl salt) or tetrafluoroborate salt was dissolved in MeOH and 0.05 equiv. of Pd(OAc)$_2$ added and up to 10% acetic acid. The reaction mixture was stirred for 5 minutes at room temperature, and 2 or more equiv. of the desired reactant was added. The reaction was typically continued for 18 hours. The catalyst was removed and the filtrate treated with activated charcoal and dried to give the crude product.

[4S-(4α,12aα)]-9-(3-Oxo-propenyl)-4-dimethylamino-3,5,10,12,12a-pentahydroxy-6-methyl-1,11-dioxo-1,4,4a,5,5a,6,11,12a-octahydro-naphthacene-2-carboxamide Preparative C18 reverse-phase HPLC. R$_t$=17.3. Analytical R$_t$=9.42. $^1$H NMR (CD$_3$OD, 300 MHz): δ 7.69 (d, 1H, J=18.0 Hz); 7.70 (d, 1H, J=7.8 Hz); 7.32 (d, 1H, J=7.8); 6.65 (d, 1H, J=18.0 Hz); 4.05 (s, 1H); 3.57 (dd, 1H); 6H); 2.85 (d, 1H); 2.71 (m, 1H); 2.60 (dd, 1H); 1.55 (d, 3H). MS(FAB): 499 (M+H).

[4S-(4α,12aα)]-9-[1'(E)-(2'-Phenyl)ethenyl]-4-dimethylamino-3,5,10,12,12a-pentahydroxy-6-methyl-1,11-dioxo-1,4,4a,5,5a,6,11,12a-octahydro-naphthacene-2-carboxamide Preparative C18 reverse-phase HPLC R$_t$=27-30. Analytical R$_t$=19.42. $^1$H NMR (CD$_3$OD, 300 MHz): δ 7.69 (d, 1H, J=8.0 Hz); 7.37 (d, 1H, J=24.0 Hz); 7.14 (m, 6H); 6.74 (d, 1H, J=8.0); 4.04 (s, 1H); 3.49 (d, 1H); 2.91 (s, 6H); 2.8 (d, 1H); 2.70 (m, 1H); 2.55 (d, 1H); 1.36 (m, 3H). MS(FAB): 547.1. HRMS calcd (C$_{30}$H$_{30}$N$_2$O$_8$+H) 547.2082, found 547.2080.

General Aryl or Heteroaryl Boronic Acids Reaction Procedure

A solution of diazonium salt (HCl or HBF$_4$) 14 in MeOH (approx. 10 mg/mL) was cooled to 0° C. and 0.1 equiv. of Pd(OAc)$_2$ was added. The mixture was stirred for 5 min, and 1 or more equiv. of phenylboronic acid or heteroaryl boronic was added and stirred for 6 h, warming to room temperature during the reaction. The catalyst was filtered away through Celite, and the filtrate dried down to yield the crude reaction product which was further purified by C18 reverse-phase preparative chromatography.

[4S-(4α,12aα)]-9-(4-Methoxy-phenyl)-4-dimethylamino-3,5,10,12,12a-pentahydroxy-6-methyl-1,11-dioxo-1,4,4a,5,5a,6,11,12a-octahydro-naphthacene-2-carboxamide The purified product was obtained by preparative C18 reverse-phase HPLC, R$_t$=33.97. Analytical R$_t$=18.2. $^1$H NMR (CD$_3$OD, 300 MHz): δ=7.50 (m, 3H); 6.94 (m, 3H); 4.16 (m, 1H); 3.82 (d, 1H); 3.30 (s, 3H); 2.79 (s, 6H); 2.74 (m, 1H); 2.56 (m, 1H); 1.53 (d, 3H); MS(FAB): 551 (M+H).

9-Carbamoyl-4-chloro-7-dimethylamino-1,8,10a,11-tetrahydroxy-10,12-dioxo-6,6a,7,10,10a, 12-hexahydro-naphthacene-2-sulfonic acid

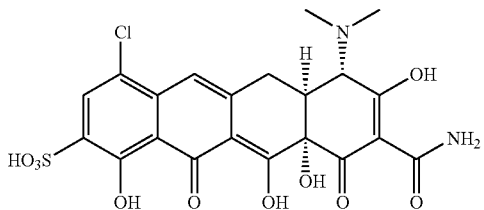

Trifluoroacetic Acid (30 mL), and 3 ml of sulfuric acid were taken in a 100 ml flask and stirred for five minutes. 7-chloro sancycline (4.3 mmol) was added to the acid mixture and stirred for 2-12 h at room temperature to 50 degree. After completion (monitored by LC/MS), the mixture was precipitated in 300 ml ether, filtered and dried. The product was then purified using preparative HPLC.

$^1$H NMR δ 7.95 (1H, s), 7.15 (1H, s), 4.22 (1H, s), 3.65-3.59 (2H, m), 3.15 (6H, s), 3.09 (1H, m), 2.99 (1H, s), 2.86 (1H, s). M+1 527.18. CHN Analysis: Calc. C, 43.10; H, 3.15; N, 4.37; S, 5.00. found C, 42.26; H, 3.73; N, 4.50; S, 5.31.

Example 2

In Vitro Minimum Inhibitory Concentration (MIC) Assay

The following assay is used to determine the efficacy of the tetracycline compounds against common bacteria. 2 mg of each compound is dissolved in 100 μl of DMSO. The solution is then added to cation-adjusted Mueller Hinton broth (CAMHB), which results in a final compound concentration of 200 μg per ml. The tetracycline compound solutions are diluted to 50 μL volumes, with a test compound concentration of 0.098 μg/ml. Optical density (OD) determinations are made from fresh log-phase broth cultures of the test strains. Dilutions are made to achieve a final cell density of $1×10^6$ CFU/ml. At OD=1, cell densities for different genera should be approximately:

| | |
|---|---|
| E. coli | $1 × 10^9$ CFU/ml |
| S. aureus | $5 × 10^8$ CFU/ml |
| Enterococcus sp. | $2.5 × 10^9$ CFU/ml |

50 μl of the cell suspensions are added to each well of microtiter plates. The final cell density should be approximately $5×10^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

This application is related to U.S. patent application Ser. No. 09/895,812, entitled "7-Substituted Tetracycline Compounds," filed Jun. 29, 2001; U.S. Provisional Patent Application Ser. No. 60/275,576, entitled "7-Substituted Tetracycline Compounds" filed Mar. 13, 2001; and U.S. Provisional Patent Application Ser. No. 60/216,760, entitled "7-Substituted Sancycline Compounds" filed on Jul. 7, 2000; the entire contents of each of these applications are hereby incorporated herein by reference.

This application is related to U.S. patent application Ser. No. 09/895,797, entitled "7,9-Substituted Tetracycline Compounds," filed on Jun. 29, 2001; and U.S. Provisional Patent Application Ser. No. 60/275,620, entitled "7,9-Substituted Tetracycline Compounds," filed on Mar. 13, 2001. The entire contents of each of these applications are incorporated herein by reference.

This application is related to U.S. patent application Ser. No. 09/895,857, entitled "9 Substituted Minocycline Compounds," filed on Jun. 29, 2001; U.S. Provisional Patent Application Ser. No. 60/275,621, entitled "9-Substituted Minocycline Compounds," filed on Mar. 13, 2001; and U.S. Provisional Patent Application Ser. No. 60/216,659, entitled "9-Substituted Minocycline Compounds," filed on Jul. 7, 2000; each of these applications are hereby incorporated herein by reference.

The invention claimed is:

1. A compound selected from the group consisting of:

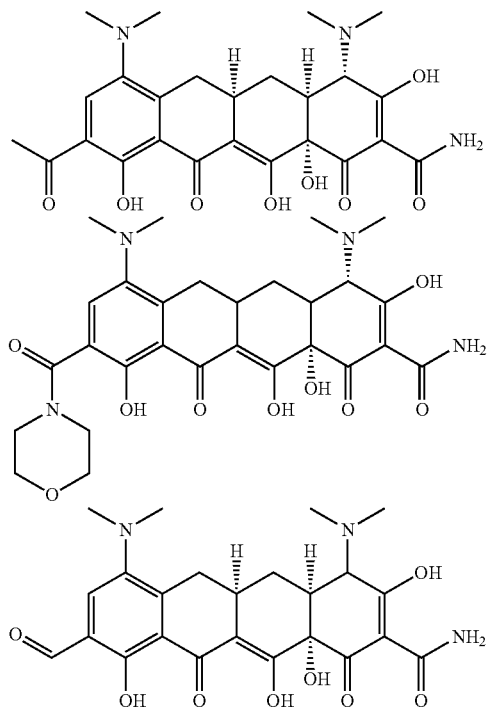

and pharmaceutically acceptable salts thereof.

2. A compound selected from the group consisting of:

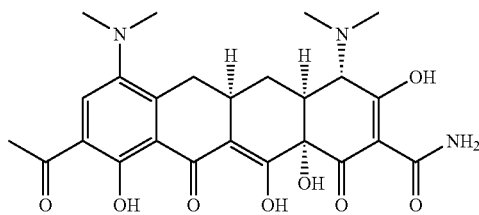

and pharmaceutically acceptable salts thereof.

3. A compound selected from the group consisting of:

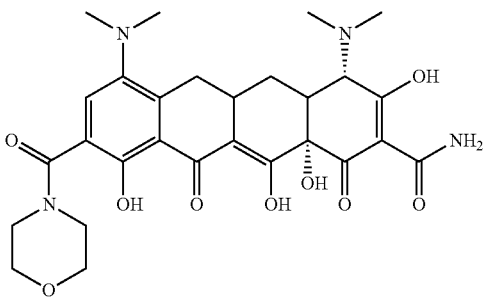

and pharmaceutically acceptable salts thereof.

4. A compound selected from the group consisting of:

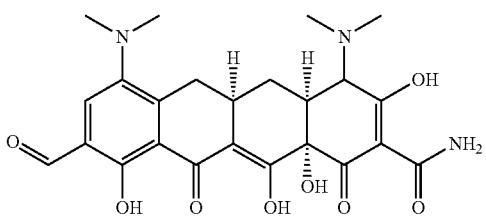

and pharmaceutically acceptable salts thereof.

5. A pharmaceutical composition comprising a therapeutically effective amount of a compound of claim 1 and a pharmaceutically acceptable carrier.

6. A pharmaceutical composition comprising a therapeutically effective amount of a compound of claim 2 and a pharmaceutically acceptable carrier.

7. A pharmaceutical composition comprising a therapeutically effective amount of a compound of claim 3 and a pharmaceutically acceptable carrier.

8. A pharmaceutical composition comprising a therapeutically effective amount of a compound of claim 4 and a pharmaceutically acceptable carrier.

9. The compound of claim 2, wherein said compound is:

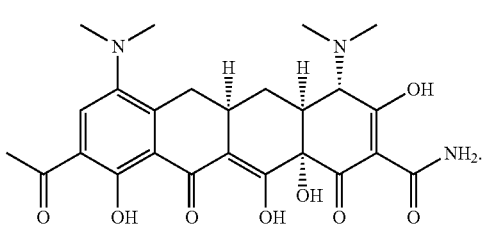

10. The compound of claim 3, wherein said compound is:

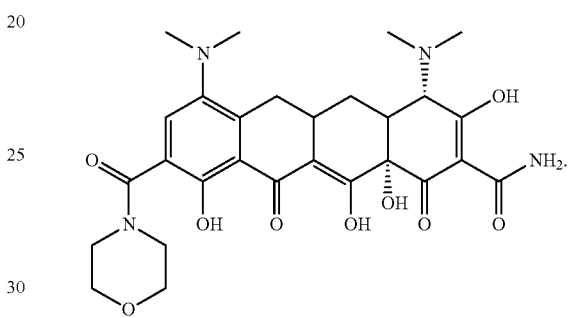

11. The compound of claim 4, wherein said compound is:

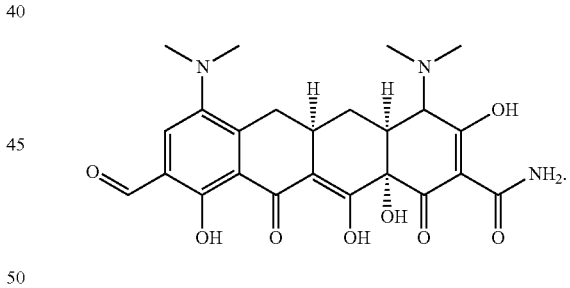

12. The pharmaceutical composition of claim 6, wherein said compound is:

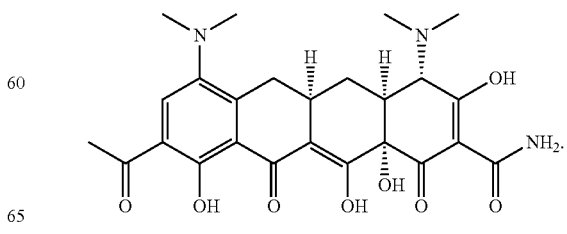

13. The pharmaceutical composition of claim 7, wherein said compound is:
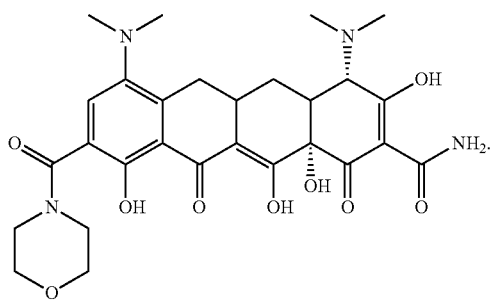
14. The pharmaceutical composition of claim 8, wherein said compound is:
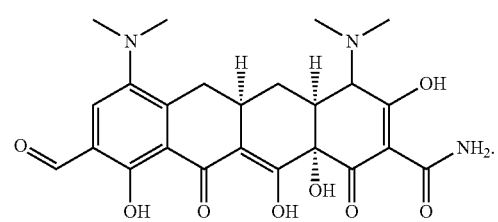
* * * * *